US010695495B2

(12) United States Patent
Blondino et al.

(10) Patent No.: US 10,695,495 B2
(45) Date of Patent: Jun. 30, 2020

(54) DEVICES AND METHODS FOR DELIVERING A LYOPHILIZED MEDICAMENT

(71) Applicant: kaleo, Inc., Richmond, VA (US)

(72) Inventors: Frank E. Blondino, Henrico, VA (US); Eric S. Edwards, Moseley, VA (US); Evan T. Edwards, Charlottesville, VA (US); Paul F. Meyers, Fishers, IN (US)

(73) Assignee: kaleo, Inc., Richmond, VA (US)

( * ) Notice: Subject to any disclaimer, the term of this patent is extended or adjusted under 35 U.S.C. 154(b) by 325 days.

(21) Appl. No.: 15/559,977

(22) PCT Filed: Mar. 24, 2016

(86) PCT No.: PCT/US2016/023995
§ 371 (c)(1),
(2) Date: Sep. 20, 2017

(87) PCT Pub. No.: WO2016/154427
PCT Pub. Date: Sep. 29, 2016

(65) Prior Publication Data
US 2018/0304018 A1    Oct. 25, 2018

Related U.S. Application Data

(60) Provisional application No. 62/137,606, filed on Mar. 24, 2015.

(51) Int. Cl.
A61M 5/28        (2006.01)
A61M 5/20        (2006.01)
(Continued)

(52) U.S. Cl.
CPC ............ *A61M 5/28* (2013.01); *A61M 5/2053* (2013.01); *A61M 5/2066* (2013.01);
(Continued)

(58) Field of Classification Search
CPC .............. A61M 5/31501; A61M 5/002; A61M 5/3202; A61M 5/3204; A61M 5/155;
(Continued)

(56) References Cited

U.S. PATENT DOCUMENTS 2,607,344 A    8/1952 Brown
2,960,087 A    11/1960 Uytenbogaart
(Continued)

FOREIGN PATENT DOCUMENTS

DE    20 2009 003 009    7/2009
EP         1287840 A1    3/2003
(Continued)

OTHER PUBLICATIONS

Office Action for Canadian Patent Application No. 2,825,637, dated Jan. 24, 2018.
(Continued)

*Primary Examiner* — Kami A Bosworth
*Assistant Examiner* — Leah J Swanson
(74) *Attorney, Agent, or Firm* — ReavesColey PLLC

(57) ABSTRACT

An apparatus includes a housing, an actuator, a lock mechanism, and a medicament container. The lock mechanism selectively engages a portion of the housing such that (1) the lock mechanism is maintained in a substantially fixed position when the housing is in a first orientation and (2) the lock mechanism is removable from the housing when the housing is in a second orientation. The medicament container is moved in a proximal direction when the lock mechanism is removed from the housing to mix a first medicament portion contained within the medicament container with a second medicament portion contained within the medicament container. The actuator can be moved from a first position to a second position when the lock mechanism is removed from the housing to release energy stored within an energy storage (Continued)

member such that the medicament container is moved in a distal direction.

23 Claims, 48 Drawing Sheets

(51) Int. Cl.
G16H 20/17 (2018.01)
G16H 40/63 (2018.01)
A61M 5/32 (2006.01)
A61M 5/24 (2006.01)
A61M 5/315 (2006.01)
A61M 5/31 (2006.01)
G09B 23/28 (2006.01)

(52) U.S. Cl.
CPC .......... *G09B 23/285* (2013.01); *G16H 20/17* (2018.01); *G16H 40/63* (2018.01); *A61M 5/24* (2013.01); *A61M 5/2425* (2013.01); *A61M 5/31501* (2013.01); *A61M 5/3204* (2013.01); *A61M 2005/206* (2013.01); *A61M 2005/2013* (2013.01); *A61M 2005/2073* (2013.01); *A61M 2005/2093* (2013.01); *A61M 2005/3123* (2013.01); *A61M 2205/50* (2013.01); *A61M 2205/505* (2013.01); *A61M 2205/581* (2013.01); *A61M 2205/583* (2013.01); *A61M 2205/80* (2013.01); *A61M 2205/8206* (2013.01)

(58) Field of Classification Search
CPC ........ A61M 5/3146; A61M 2005/2073; A61M 2005/314; A61M 11/00; A61M 11/02; A61M 11/006; A61M 11/007; A61M 11/08; A61M 2205/215; A61M 2205/276
See application file for complete search history.

(56) References Cited

U.S. PATENT DOCUMENTS

| | | | |
|---|---|---|---|
| 3,055,362 A | 9/1962 | Uytenbogaart | |
| 3,115,133 A | 12/1963 | Morando | |
| 3,426,448 A | 2/1969 | Sarnoff | |
| 3,563,373 A | 2/1971 | Paulson | |
| 3,565,070 A * | 2/1971 | Hanson .............. A61M 15/0091 | |
| | | | 128/200.23 |
| 3,688,765 A | 9/1972 | Gasaway | |
| 3,768,472 A | 10/1973 | Hodosh et al. | |
| 3,795,061 A | 3/1974 | Sarnoff et al. | |
| 3,797,489 A | 3/1974 | Sarnoff | |
| 3,945,379 A | 3/1976 | Pritz et al. | |
| 4,108,177 A | 8/1978 | Pistor | |
| 4,124,024 A | 11/1978 | Schwebel et al. | |
| 4,226,235 A | 10/1980 | Sarnoff et al. | |
| 4,258,713 A | 3/1981 | Wardlaw | |
| 4,360,019 A | 11/1982 | Portner et al. | |
| 4,394,863 A | 7/1983 | Bartner | |
| 4,424,057 A | 1/1984 | House | |
| 4,441,629 A | 4/1984 | Mackal | |
| 4,484,910 A | 11/1984 | Sarnoff | |
| 4,573,976 A | 3/1986 | Sampson et al. | |
| 4,596,556 A | 6/1986 | Morrow et al. | |
| 4,610,666 A | 9/1986 | Pizzino | |
| 4,617,557 A | 10/1986 | Gordon | |
| 4,624,660 A | 11/1986 | Mijers et al. | |
| 4,640,686 A | 2/1987 | Dalling et al. | |
| 4,643,721 A | 2/1987 | Brunet | |
| 4,664,653 A | 5/1987 | Sagstetter et al. | |
| 4,666,430 A | 5/1987 | Brown et al. | |
| 4,673,657 A | 6/1987 | Christian | |
| 4,689,042 A | 8/1987 | Sarnoff et al. | |
| 4,693,708 A | 9/1987 | Wanderer et al. | |
| 4,755,169 A | 7/1988 | Sarnoff et al. |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,820,286 A | 4/1989 | van der Wal |
| 4,822,340 A | 4/1989 | Kamstra |
| 4,826,489 A | 5/1989 | Haber et al. |
| 4,853,521 A | 8/1989 | Claeys et al. |
| 4,874,381 A | 10/1989 | Vetter |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,042,977 A | 8/1991 | Bechtold et al. |
| 5,062,603 A | 11/1991 | Smith et al. |
| 5,064,413 A | 11/1991 | McKinnon et al. |
| 5,071,353 A | 12/1991 | van der Wal |
| 5,080,649 A | 1/1992 | Vetter |
| 5,085,642 A | 2/1992 | Sarnoff et al. |
| 5,092,842 A | 3/1992 | Bechtold et al. |
| 5,092,843 A | 3/1992 | Monroe et al. |
| 5,104,380 A | 4/1992 | Holman et al. |
| 5,125,898 A | 6/1992 | Kaufhold, Jr. et al. |
| 5,139,490 A | 8/1992 | Vetter et al. |
| 5,147,311 A | 9/1992 | Pickhard |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,244,465 A | 9/1993 | Michel |
| 5,271,527 A | 12/1993 | Haber et al. |
| 5,281,198 A | 1/1994 | Haber et al. |
| 5,286,258 A | 2/1994 | Haber et al. |
| 5,295,965 A | 3/1994 | Wilmot |
| 5,298,023 A | 3/1994 | Haber et al. |
| 5,298,024 A | 3/1994 | Richmond |
| 5,312,326 A | 5/1994 | Myers et al. |
| 5,314,412 A | 5/1994 | Rex |
| 5,320,603 A | 6/1994 | Vetter et al. |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,383,864 A | 1/1995 | van den Heuvel |
| 5,394,866 A | 3/1995 | Ritson et al. |
| 5,395,345 A | 3/1995 | Gross |
| 5,399,163 A | 3/1995 | Peterson et al. |
| 5,417,660 A | 5/1995 | Martin |
| 5,466,217 A | 11/1995 | Myers et al. |
| 5,514,097 A | 5/1996 | Knauer |
| 5,514,135 A | 5/1996 | Earle |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,615,771 A | 4/1997 | Hollister |
| 5,616,132 A | 4/1997 | Newman |
| 5,645,534 A | 7/1997 | Chanoch |
| 5,662,612 A | 9/1997 | Niehoff |
| 5,681,291 A | 10/1997 | Galli |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |
| 5,728,074 A | 3/1998 | Castellano et al. |

(56) References Cited

U.S. PATENT DOCUMENTS

| | | |
|---|---|---|
| 5,743,886 A | 4/1998 | Lynn et al. |
| 5,772,635 A | 6/1998 | Dastur et al. |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,397 A | 9/1998 | Goodman et al. |
| 5,814,020 A | 9/1998 | Gross |
| 5,823,346 A | 10/1998 | Weiner |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,848,990 A | 12/1998 | Cirelli et al. |
| 5,852,590 A | 12/1998 | de la Huerga |
| 5,853,292 A | 12/1998 | Eggert et al. |
| 5,858,001 A | 1/1999 | Tsals et al. |
| 5,865,795 A | 2/1999 | Schiff et al. |
| 5,868,711 A | 2/1999 | Kramer et al. |
| 5,868,713 A | 2/1999 | Klippenstein |
| 5,868,721 A | 2/1999 | Marinacci |
| D407,487 S | 3/1999 | Greubel et al. |
| 5,876,380 A | 3/1999 | Manganini et al. |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |
| 5,970,457 A | 10/1999 | Brant et al. |
| 5,971,953 A | 10/1999 | Bachynsky |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,056,728 A | 5/2000 | von Schuckmann |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,083,199 A | 7/2000 | Thorley et al. |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,120,786 A | 9/2000 | Cheikh |
| 6,123,685 A | 9/2000 | Reynolds |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,179,812 B1 | 1/2001 | Botich et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,258,063 B1 | 7/2001 | Haar et al. |
| 6,259,654 B1 | 7/2001 | de la Huerga |
| 6,264,629 B1 | 7/2001 | Landau |
| 6,312,412 B1 | 11/2001 | Saied et al. |
| 6,317,630 B1 | 11/2001 | Gross et al. |
| 6,334,070 B1 | 12/2001 | Nova et al. |
| 6,364,866 B1 | 4/2002 | Furr et al. |
| 6,371,939 B2 | 4/2002 | Bergens et al. |
| 6,387,078 B1 | 5/2002 | Gillespie, III |
| 6,405,912 B2 | 6/2002 | Giannou |
| 6,406,455 B1 | 6/2002 | Willis et al. |
| 6,411,567 B1 | 6/2002 | Niemiec et al. |
| 6,413,236 B1 | 7/2002 | Van Dyke |
| 6,419,656 B1 | 7/2002 | Vetter et al. |
| 6,425,897 B2 | 7/2002 | Overes et al. |
| 6,427,684 B2 * | 8/2002 | Ritsche ............ A61M 15/0081 128/200.23 |
| 6,428,517 B1 | 8/2002 | Hochman et al. |
| 6,428,528 B2 | 8/2002 | Sadowski |
| 6,454,746 B1 | 9/2002 | Bydlon et al. |
| 6,475,181 B1 | 11/2002 | Potter et al. |
| 6,478,769 B1 | 11/2002 | Parker |
| 6,478,771 B1 | 11/2002 | Lavi et al. |
| 6,482,186 B1 | 11/2002 | Douglas et al. |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,540,672 B1 | 4/2003 | Simonsen et al. |
| 6,540,675 B2 | 4/2003 | Aceti et al. |
| 6,544,233 B1 | 4/2003 | Fukui et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,560,471 B1 | 5/2003 | Heller |
| 6,565,533 B1 | 5/2003 | Smith et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,599,272 B1 | 7/2003 | Hjertman et al. |
| 6,616,627 B2 | 9/2003 | Willis et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,648,850 B2 | 11/2003 | Landau |
| 6,656,150 B2 | 12/2003 | Hill et al. |
| 6,656,163 B1 | 12/2003 | Marshall et al. |
| 6,659,980 B2 | 12/2003 | Moberg et al. |
| 6,676,630 B2 | 1/2004 | Landau et al. |
| 6,679,862 B2 | 1/2004 | Diaz et al. |
| 6,689,093 B2 | 2/2004 | Landau |
| 6,702,778 B2 | 3/2004 | Hill et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,661 B2 | 4/2004 | Munk et al. |
| 6,736,796 B2 | 5/2004 | Shekalim |
| 6,743,203 B1 | 6/2004 | Pickhard |
| 6,743,635 B2 | 6/2004 | Neel et al. |
| 6,749,437 B2 | 6/2004 | Chan |
| 6,752,781 B2 | 6/2004 | Landau et al. |
| 6,764,469 B2 | 7/2004 | Broselow |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,817,987 B2 | 11/2004 | Vetter et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |

(56) References Cited

U.S. PATENT DOCUMENTS

| | | |
|---|---|---|
| 6,893,420 B2 | 5/2005 | Arnisolle |
| 6,923,764 B2 | 8/2005 | Aceti et al. |
| 6,936,029 B2 | 8/2005 | Mann et al. |
| 6,936,032 B1 | 8/2005 | Bush, Jr. et al. |
| 6,937,150 B2 | 8/2005 | Medema et al. |
| 6,942,646 B2 | 9/2005 | Langley et al. |
| 6,946,299 B2 | 9/2005 | Neel et al. |
| 6,949,082 B2 | 9/2005 | Langley et al. |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,077,835 B2 | 7/2006 | Robinson et al. |
| 7,104,972 B2 | 9/2006 | Moller et al. |
| 7,113,101 B2 | 9/2006 | Petersen et al. |
| 7,116,233 B2 | 10/2006 | Zhurin |
| 7,118,553 B2 | 10/2006 | Scherer |
| 7,126,879 B2 | 10/2006 | Snyder |
| 7,158,011 B2 | 1/2007 | Brue |
| 7,191,916 B2 | 3/2007 | Clifford et al. |
| 7,278,983 B2 | 10/2007 | Ireland et al. |
| 7,299,981 B2 | 11/2007 | Hickle et al. |
| 7,329,241 B2 | 2/2008 | Horvath et al. |
| 7,351,223 B2 | 4/2008 | Call |
| 7,416,540 B2 | 8/2008 | Edwards et al. |
| 7,500,963 B2 | 3/2009 | Westbye et al. |
| 7,500,967 B2 | 3/2009 | Thorley et al. |
| 7,503,907 B1 | 3/2009 | Lesch, Jr. |
| 7,544,188 B2 | 6/2009 | Edwards et al. |
| 7,611,491 B2 | 11/2009 | Pickhard |
| 7,648,482 B2 | 1/2010 | Edwards et al. |
| 7,648,483 B2 | 1/2010 | Edwards et al. |
| 7,678,073 B2 | 3/2010 | Griffiths et al. |
| 7,686,788 B2 | 3/2010 | Freyman et al. |
| 7,708,719 B2 | 5/2010 | Wilmot et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,758,550 B2 | 7/2010 | Bollenbach et al. |
| 7,806,866 B2 | 10/2010 | Hommann et al. |
| 7,850,662 B2 | 12/2010 | Veasey et al. |
| 7,871,393 B2 | 1/2011 | Monroe |
| 7,918,823 B2 | 4/2011 | Edwards et al. |
| 7,918,832 B2 | 4/2011 | Veasey et al. |
| 7,931,614 B2 | 4/2011 | Gonnelli et al. |
| 7,938,802 B2 | 5/2011 | Bicknell et al. |
| 7,947,017 B2 | 5/2011 | Edwards et al. |
| 8,016,788 B2 | 9/2011 | Edwards et al. |
| 8,021,335 B2 | 9/2011 | Lesch, Jr. |
| 8,105,281 B2 | 1/2012 | Edwards et al. |
| 8,105,293 B2 | 1/2012 | Pickhard |
| 8,123,719 B2 | 2/2012 | Edwards et al. |
| 8,162,886 B2 | 4/2012 | Sadowski et al. |
| 8,172,082 B2 | 5/2012 | Edwards et al. |
| 8,177,749 B2 | 5/2012 | Slate et al. |
| 8,206,360 B2 | 6/2012 | Edwards et al. |
| 8,231,573 B2 | 7/2012 | Edwards et al. |
| 8,251,947 B2 | 8/2012 | Kramer et al. |
| 8,276,583 B2 | 10/2012 | Farieta et al. |
| 8,313,466 B2 | 11/2012 | Edwards et al. |
| 8,361,029 B2 | 1/2013 | Edwards et al. |
| 8,361,035 B2 | 1/2013 | Thorley et al. |
| 8,425,462 B2 | 4/2013 | Edwards et al. |
| 8,574,214 B2 | 11/2013 | Kühn et al. |
| 8,608,698 B2 | 12/2013 | Edwards et al. |
| 8,613,720 B2 | 12/2013 | Bendek et al. |
| 8,627,816 B2 | 1/2014 | Edwards et al. |
| 8,632,504 B2 | 1/2014 | Young |
| 8,684,968 B2 | 4/2014 | Genosar |
| 8,690,827 B2 | 4/2014 | Edwards et al. |
| 8,708,968 B2 | 4/2014 | Julian et al. |
| 8,728,042 B2 | 5/2014 | Pickhard |
| 8,734,394 B2 | 5/2014 | Adams et al. |
| 8,920,367 B2 | 12/2014 | Edwards et al. |
| 8,920,377 B2 | 12/2014 | Edwards et al. |
| 8,939,943 B2 | 1/2015 | Edwards et al. |
| 8,961,455 B2 | 2/2015 | Holmqvist et al. |
| 9,022,980 B2 | 5/2015 | Edwards et al. |
| 9,056,170 B2 | 6/2015 | Edwards et al. |
| 9,084,849 B2 | 7/2015 | Edwards et al. |
| 9,149,579 B2 | 10/2015 | Edwards et al. |
| 9,173,999 B2 | 11/2015 | Edwards et al. |
| 9,199,037 B2 | 12/2015 | Buchine et al. |
| 9,289,563 B2 | 3/2016 | Pickhard et al. |
| 9,345,831 B2 | 5/2016 | Raday et al. |
| 9,586,010 B2 | 3/2017 | Mesa et al. |
| 10,105,499 B2 | 10/2018 | Schwirtz et al. |
| 10,398,838 B2 | 9/2019 | Tremblay et al. |
| 2002/0016567 A1 | 2/2002 | Hochman et al. |
| 2002/0042596 A1 | 4/2002 | Hartlaub et al. |
| 2002/0055711 A1 | 5/2002 | Lavi et al. |
| 2002/0074345 A1 | 6/2002 | Schneider et al. |
| 2002/0076679 A1 | 6/2002 | Aman |
| 2002/0090601 A1 | 7/2002 | Strupat et al. |
| 2002/0096543 A1 | 7/2002 | Juselius |
| 2003/0015191 A1 | 1/2003 | Armstrong et al. |
| 2003/0028145 A1 | 2/2003 | Duchon et al. |
| 2003/0040717 A1 | 2/2003 | Saulenas et al. |
| 2003/0105430 A1 | 6/2003 | Lavi et al. |
| 2003/0106824 A1 | 6/2003 | Wilmot et al. |
| 2003/0120222 A1 | 6/2003 | Vaillancourt |
| 2003/0135388 A1 | 7/2003 | Martucci et al. |
| 2004/0015125 A1 | 1/2004 | Alexandre et al. |
| 2004/0019326 A1 | 1/2004 | Gilbert et al. |
| 2004/0024361 A1 | 2/2004 | Fago et al. |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0054327 A1 | 3/2004 | Gillespie, III |
| 2004/0092874 A1 | 5/2004 | Mazidji |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0210199 A1 | 10/2004 | Atterbury et al. |
| 2004/0220524 A1 | 11/2004 | Sadowski et al. |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0049561 A1 | 3/2005 | Hommann et al. |
| 2005/0062603 A1 | 3/2005 | Fuerst et al. |
| 2005/0090781 A1 | 4/2005 | Baba et al. |
| 2005/0090782 A1 | 4/2005 | Marshall et al. |
| 2005/0096588 A1 | 5/2005 | Hagmann et al. |
| 2005/0101912 A1 | 5/2005 | Faust et al. |
| 2005/0134433 A1 | 6/2005 | Sweeney, II |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0182358 A1 | 8/2005 | Veit et al. |
| 2005/0183982 A1 | 8/2005 | Giewercer |
| 2005/0186221 A1 | 8/2005 | Reynolds et al. |
| 2005/0192530 A1 | 9/2005 | Castellano |
| 2005/0197654 A1 | 9/2005 | Edman et al. |
| 2005/0203466 A1 | 9/2005 | Hommann et al. |
| 2005/0261742 A1 | 11/2005 | Nova et al. |
| 2005/0267403 A1 | 12/2005 | Landau et al. |
| 2005/0277891 A1 | 12/2005 | Sibbitt |
| 2006/0030819 A1 | 2/2006 | Young et al. |
| 2006/0053036 A1 | 3/2006 | Coffman et al. |

(56) References Cited

U.S. PATENT DOCUMENTS

| | | |
|---|---|---|
| 2006/0058848 A1 | 3/2006 | Piraino et al. |
| 2006/0069350 A1 | 3/2006 | Buenger et al. |
| 2006/0084908 A1 | 4/2006 | Bonney et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129089 A1 | 6/2006 | Stamp |
| 2006/0129090 A1 | 6/2006 | Moberg et al. |
| 2006/0189938 A1 | 8/2006 | Hommann et al. |
| 2006/0200077 A1 | 9/2006 | Righi et al. |
| 2006/0223027 A1 | 10/2006 | Smith et al. |
| 2006/0235354 A1 | 10/2006 | Kaal et al. |
| 2006/0247578 A1 | 11/2006 | Arguedas et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0074722 A1 | 4/2007 | Giroux et al. |
| 2007/0100288 A1 | 5/2007 | Bozeman et al. |
| 2007/0129686 A1 | 6/2007 | Daily et al. |
| 2007/0173772 A1 | 7/2007 | Liversidge |
| 2007/0184847 A1 | 8/2007 | Hansen et al. |
| 2007/0203247 A1 | 8/2007 | Phillips et al. |
| 2007/0210147 A1 | 9/2007 | Morrone et al. |
| 2007/0213598 A1 | 9/2007 | Howard et al. |
| 2007/0233001 A1 | 10/2007 | Burroughs et al. |
| 2008/0111685 A1 | 5/2008 | Olson et al. |
| 2008/0160492 A1 | 7/2008 | Campbell et al. |
| 2008/0171995 A1 | 7/2008 | Vitullo et al. |
| 2008/0188798 A1 | 8/2008 | Weber |
| 2008/0228143 A1 | 9/2008 | Stamp |
| 2008/0255513 A1 | 10/2008 | Kaal et al. |
| 2009/0005735 A1 | 1/2009 | Wikner et al. |
| 2009/0093759 A1 | 4/2009 | Judd et al. |
| 2009/0209939 A1 | 8/2009 | Verespej et al. |
| 2009/0221962 A1 | 9/2009 | Kaal et al. |
| 2009/0240200 A1 | 9/2009 | Heneveld et al. |
| 2010/0137808 A1 | 6/2010 | Wilmot et al. |
| 2010/0160894 A1 | 6/2010 | Julian et al. |
| 2011/0060274 A1 | 3/2011 | Kuhn |
| 2011/0201999 A1 | 8/2011 | Cronenberg |
| 2011/0270220 A1 | 11/2011 | Gencsar |
| 2012/0016296 A1 | 1/2012 | Charles |
| 2012/0046613 A1 | 2/2012 | Plumptre |
| 2012/0056019 A1 | 3/2012 | Renz et al. |
| 2012/0107783 A1 | 5/2012 | Julian et al. |
| 2012/0125951 A1 | 5/2012 | Leak et al. |
| 2012/0130318 A1 | 5/2012 | Young |
| 2012/0136298 A1 | 5/2012 | Bendix et al. |
| 2012/0136316 A1 | 5/2012 | Davies et al. |
| 2012/0143144 A1 | 6/2012 | Young |
| 2012/0172804 A1 | 7/2012 | Plumptre |
| 2012/0172817 A1 | 7/2012 | Bruggemann et al. |
| 2012/0191049 A1 | 7/2012 | Harms et al. |
| 2012/0191066 A1 | 7/2012 | Schabbach et al. |
| 2012/0197210 A1 | 8/2012 | Kuhn et al. |
| 2012/0209200 A1 | 8/2012 | Jones et al. |
| 2012/0220949 A1 | 8/2012 | Davies et al. |
| 2012/0226238 A1 | 9/2012 | Davies et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0271243 A1 | 10/2012 | Plumptre et al. |
| 2012/0283648 A1 | 11/2012 | Veasey et al. |
| 2012/0283651 A1 | 11/2012 | Veasey et al. |
| 2012/0283662 A1 | 11/2012 | MacDonald et al. |
| 2012/0289906 A1 | 11/2012 | Jones et al. |
| 2012/0289929 A1 | 11/2012 | Boyd et al. |
| 2012/0310168 A1 | 12/2012 | Plumptre et al. |
| 2012/0310206 A1 | 12/2012 | Kouyoumjian et al. |
| 2012/0323186 A1 | 12/2012 | Karlsen et al. |
| 2012/0325865 A1 | 12/2012 | Forstreuter et al. |
| 2012/0330244 A1 | 12/2012 | Helmer et al. |
| 2013/0035664 A1 | 2/2013 | Mojdehbakhsh et al. |
| 2013/0060231 A1 | 3/2013 | Adlon et al. |
| 2013/0060232 A1 | 3/2013 | Adlon et al. |
| 2013/0079718 A1 | 3/2013 | Shang et al. |
| 2013/0090604 A1 | 4/2013 | Davies et al. |
| 2013/0102973 A1 | 4/2013 | Thorley et al. |
| 2013/0110050 A1 | 5/2013 | Boyd et al. |
| 2013/0178823 A1 | 7/2013 | Buchine et al. |
| 2013/0226084 A1 | 8/2013 | Samandi et al. |
| 2013/0226134 A1 | 8/2013 | Schabbach et al. |
| 2013/0237924 A1 | 9/2013 | Leak et al. |
| 2013/0237932 A1 | 9/2013 | Thueer et al. |
| 2013/0245562 A1 | 9/2013 | Kouyoumjian et al. |
| 2013/0266919 A1 | 10/2013 | Baker et al. |
| 2013/0274707 A1 | 10/2013 | Wilmot et al. |
| 2013/0317477 A1 | 11/2013 | Edwards et al. |
| 2013/0317480 A1 | 11/2013 | Reber |
| 2014/0046259 A1 | 2/2014 | Reber et al. |
| 2014/0081234 A1 | 3/2014 | Eggert et al. |
| 2014/0114258 A1 | 4/2014 | Day |
| 2014/0188075 A1 | 7/2014 | Eggert et al. |
| 2014/0257185 A1 | 9/2014 | Bechmann et al. |
| 2014/0276385 A1 | 9/2014 | Buchine et al. |
| 2014/0336586 A1 | 11/2014 | Bengtsson et al. |
| 2014/0336610 A1 | 11/2014 | Michel et al. |
| 2015/0051538 A1 | 2/2015 | Hata et al. |
| 2015/0174323 A1 | 6/2015 | Edwards et al. |
| 2015/0174325 A1 | 6/2015 | Young et al. |
| 2015/0231334 A1 | 8/2015 | Buchine et al. |
| 2015/0283323 A1 | 10/2015 | Young et al. |
| 2015/0367072 A1 | 12/2015 | Constantineau et al. |
| 2016/0015907 A1 | 1/2016 | Edwards et al. |
| 2016/0018872 A1 | 1/2016 | Tu et al. |
| 2016/0022909 A1 | 1/2016 | Edwards et al. |
| 2016/0045670 A1 | 2/2016 | Edwards et al. |
| 2016/0074584 A1 | 3/2016 | Carmel et al. |
| 2016/0184521 A1 | 6/2016 | Edwards et al. |
| 2016/0193412 A1 | 7/2016 | Cereda et al. |
| 2016/0250414 A1 | 9/2016 | Edwards et al. |
| 2016/0256639 A1 | 9/2016 | Van Sickle et al. |
| 2016/0296716 A1 | 10/2016 | Cabiri et al. |
| 2016/0354556 A1 | 12/2016 | Zucker et al. |
| 2017/0151393 A1 | 6/2017 | Edwards et al. |
| 2017/0246393 A1 | 8/2017 | Genosar |
| 2017/0328931 A1 | 11/2017 | Zhang et al. |
| 2018/0296760 A1 | 10/2018 | Csenar et al. |
| 2019/0009025 A1 | 1/2019 | Chakrabarti et al. |
| 2019/0009027 A1 | 1/2019 | Edwards et al. |
| 2019/0151548 A1 | 5/2019 | Edwards et al. |
| 2019/0175837 A1 | 6/2019 | Edwards et al. |
| 2019/0275253 A1 | 9/2019 | Edwards et al. |
| 2019/0282763 A1 | 9/2019 | Edwards et al. |
| 2019/0328971 A1 | 10/2019 | Edwards et al. |
| 2019/0358399 A1 | 11/2019 | Edwards et al. |
| 2019/0381245 A1 | 12/2019 | Edwards et al. |

FOREIGN PATENT DOCUMENTS

| | | |
|---|---|---|
| EP | 1462134 A1 | 9/2004 |
| EP | 1518575 A1 | 3/2005 |
| EP | 1712178 A2 | 10/2006 |
| EP | 1095668 | 4/2007 |
| FR | 2506161 | 11/1982 |
| FR | 2509615 | 1/1983 |
| GB | 2490807 | 11/2012 |
| JP | 51-021295 | 2/1976 |
| JP | 55-75335 | 5/1980 |
| MX | PA04009276 | 1/2005 |
| WO | WO 86/06967 | 12/1986 |
| WO | WO 91/04760 | 4/1991 |
| WO | WO 92/18176 | 10/1992 |
| WO | WO 93/02720 | 2/1993 |
| WO | WO 94/06487 | 3/1994 |
| WO | WO 95/13838 | 5/1995 |
| WO | WO 95/26009 | 9/1995 |
| WO | WO 95/35126 | 12/1995 |
| WO | WO 98/52632 | 11/1998 |
| WO | WO 99/10031 | 3/1999 |
| WO | WO 2001/024690 | 4/2001 |
| WO | WO 2001/026020 | 4/2001 |
| WO | WO 2001/041849 | 6/2001 |
| WO | WO 2001/088828 | 11/2001 |

(56) References Cited

FOREIGN PATENT DOCUMENTS

| | | |
|---|---|---|
| WO | WO 2001/093926 | 12/2001 |
| WO | WO 2002/100469 | 12/2002 |
| WO | WO 2003/095001 | 11/2003 |
| WO | WO 2003/097133 | 11/2003 |
| WO | WO 2004/054644 | 7/2004 |
| WO | WO 2005/050526 | 6/2005 |
| WO | WO 2005/077441 | 8/2005 |
| WO | WO 2006/045525 | 5/2006 |
| WO | WO 2006/109778 | 10/2006 |
| WO | WO 2006/125692 | 11/2006 |
| WO | WO 2007/075839 | 7/2007 |
| WO | WO 2008/005315 | 1/2008 |
| WO | WO 2008/082704 | 7/2008 |
| WO | WO 2008/148864 | 12/2008 |
| WO | WO 2010/033806 | 3/2010 |
| WO | WO 2012/164402 A2 | 12/2012 |
| WO | WO 2013/034984 A2 | 3/2013 |
| WO | WO 2013/044172 | 3/2013 |
| WO | WO 2013/086292 | 6/2013 |
| WO | WO 2013/119591 A1 | 8/2013 |
| WO | WO 2014/085118 A1 | 6/2014 |
| WO | WO 2014/145959 A1 | 9/2014 |
| WO | WO 2016/160341 A1 | 10/2016 |
| WO | WO 2017/034618 A1 | 3/2017 |
| WO | WO 2018/078121 | 5/2018 |

OTHER PUBLICATIONS

Extended European Search Report for European Patent Application No. 16769685.5, dated Nov. 21, 2018.
"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8>, 3 pages.
Office Action for U.S. Appl. No. 13/053,451, dated Nov. 15, 2012.
Office Action for Japanese Patent Application No. JP2007-553358 dated Feb. 24, 2010.
International Search Report and Written Opinion for International Patent Application No. PCT/US06/03415, dated Jul. 13, 2006, 10 pages.
International Search Report and Written Opinion for International Patent Application No. PCT/US07/007626, dated Sep. 29, 2008.
Office Action for U.S. Appl. No. 11/692,359, dated Jul. 18, 2011.
Office Action for U.S. Appl. No. 13/827,582, dated Oct. 16, 2015.
International Search Report and Written Opinion for International Application No. PCT/US2016/023995 dated Sep. 22, 2016.
Office Action for U.S. Appl. No. 14/579,298, dated Dec. 7, 2016.
Office Action for AU Application No. 2016235054, dated Nov. 1, 2019.

* cited by examiner

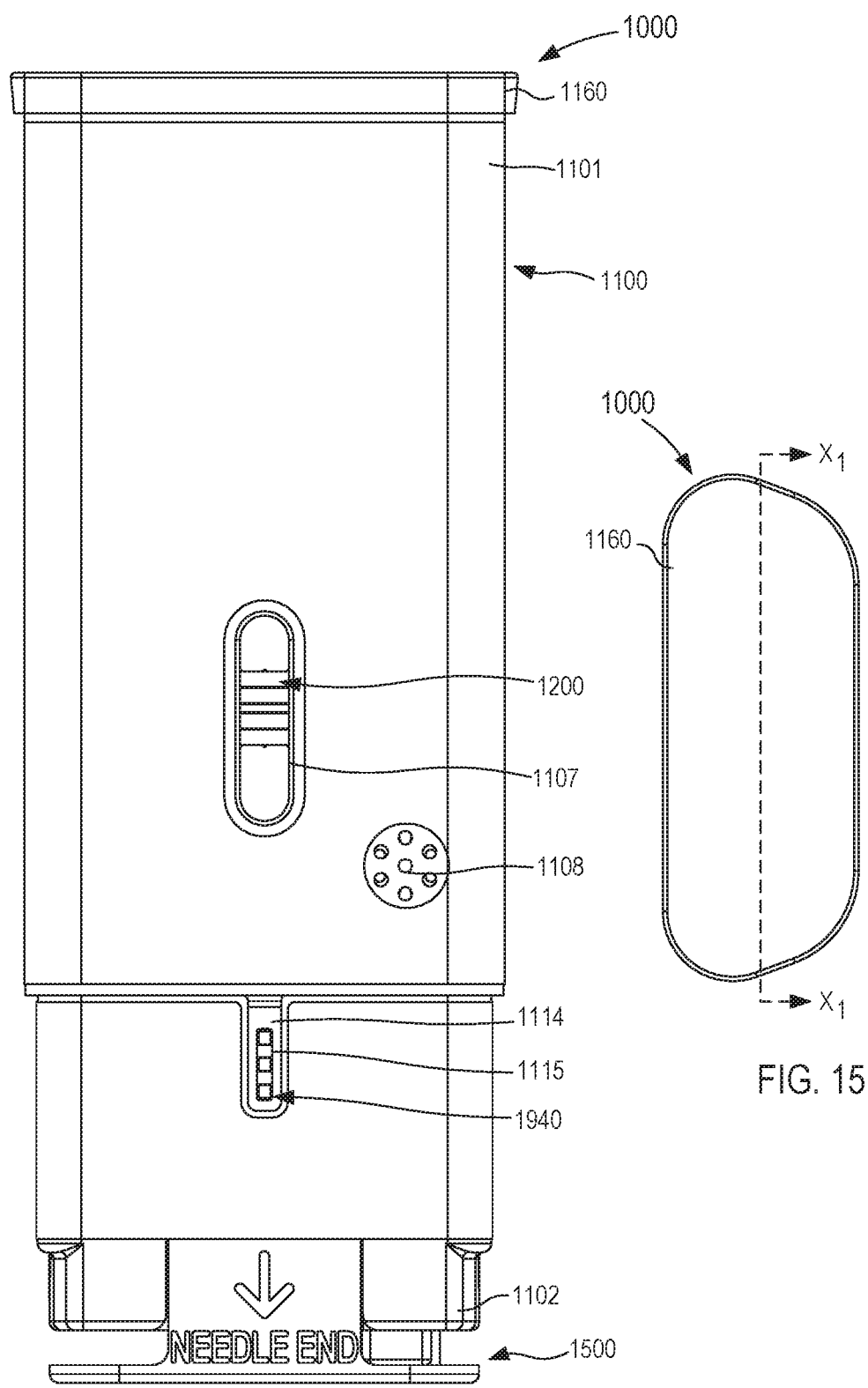

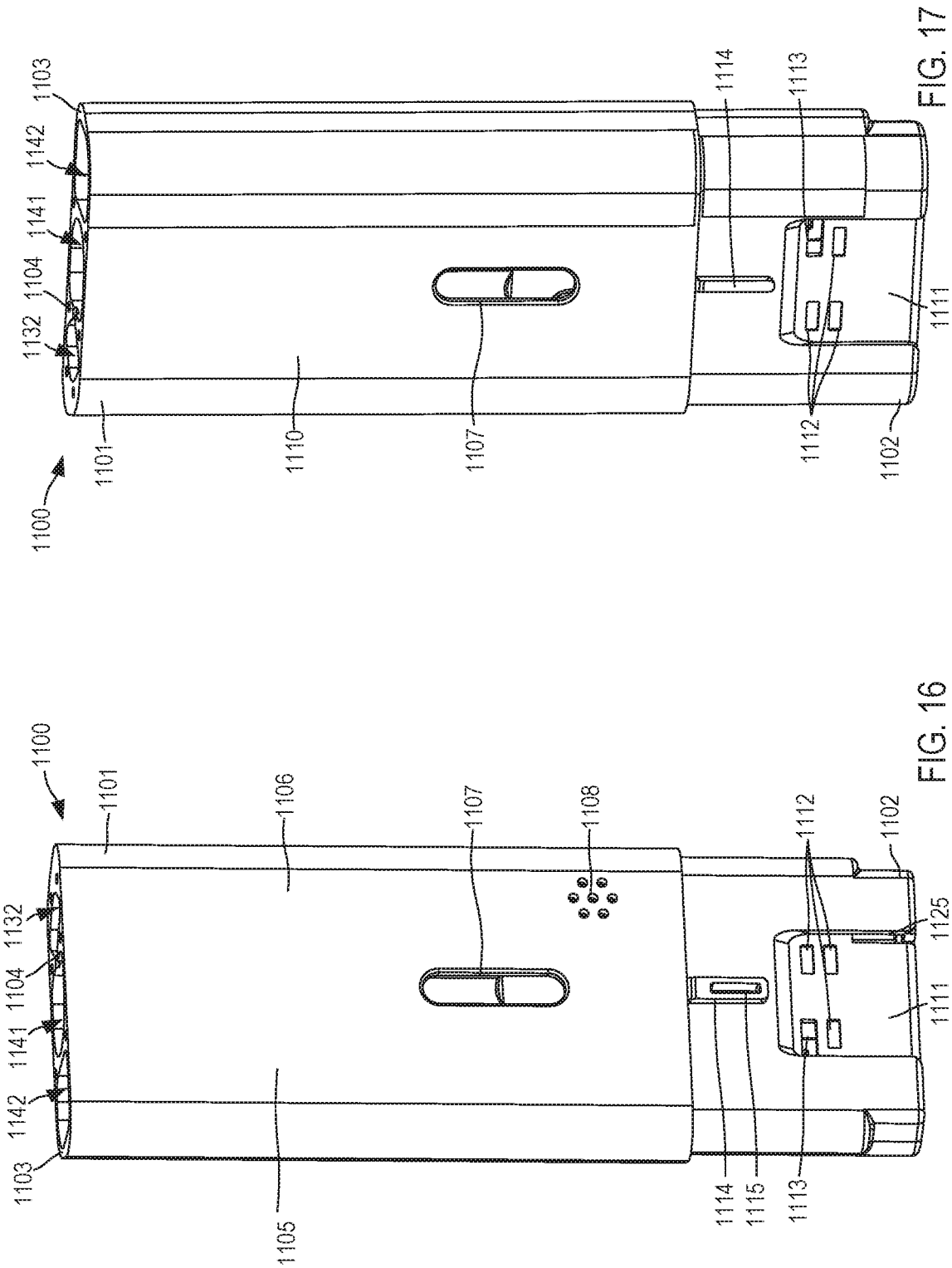

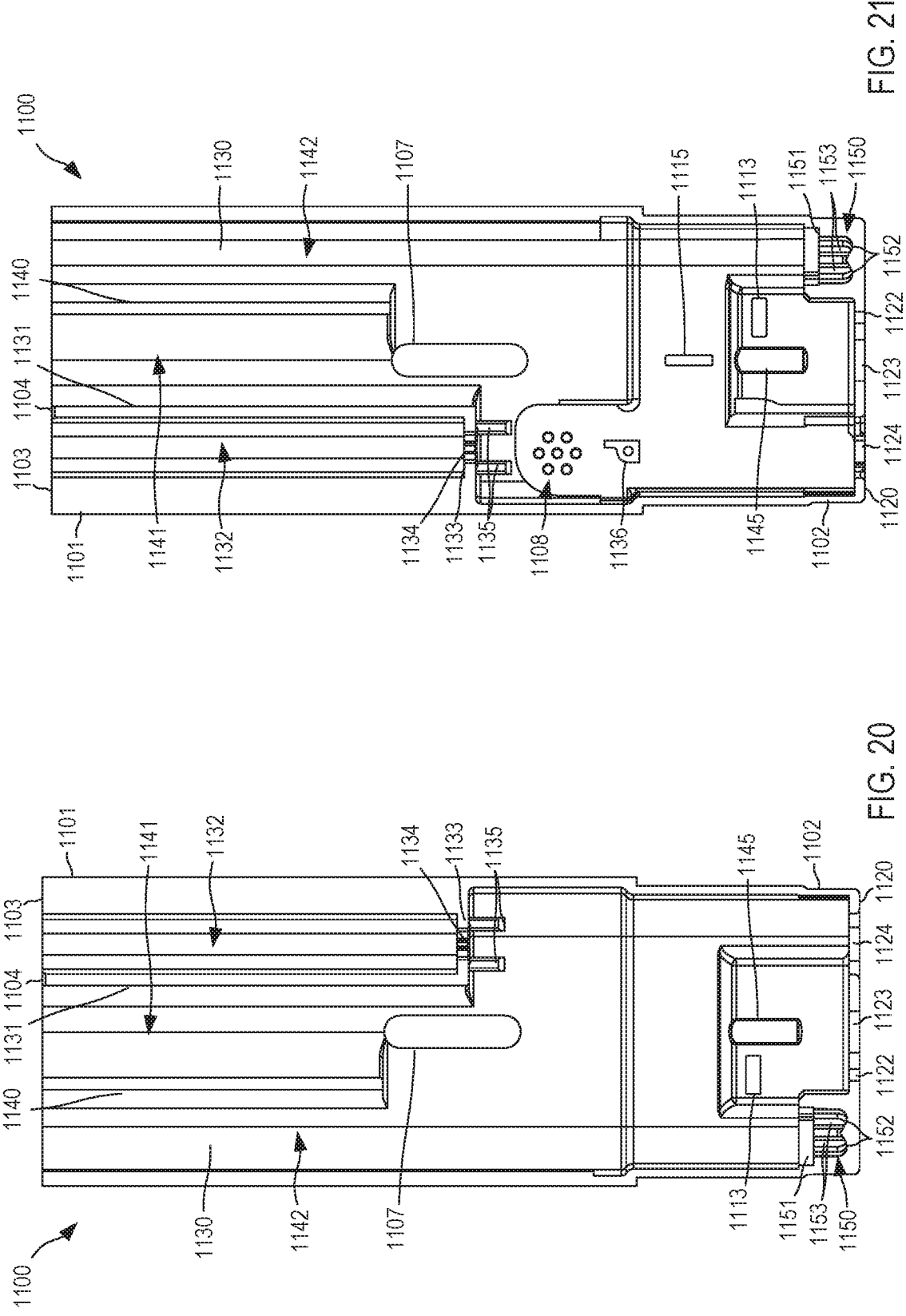

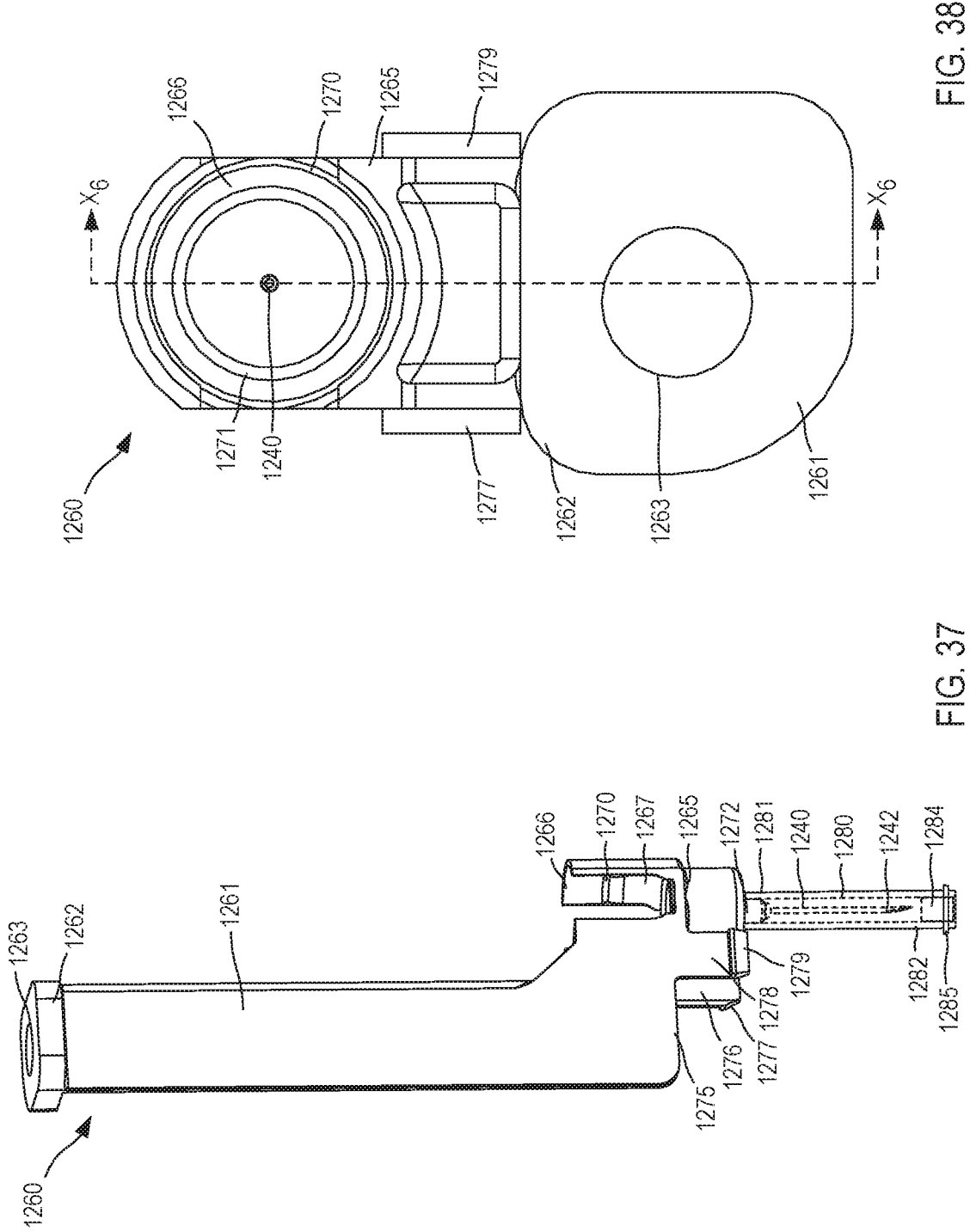

DEVICES AND METHODS FOR DELIVERING A LYOPHILIZED MEDICAMENT

CROSS-REFERENCE TO RELATED APPLICATIONS

This application is a U.S. national stage filing under 35 U.S.C. § 371 of International Application No. PCT/US2016/23995, entitled "DEVICES AND METHODS FOR DELIVERING A LYOPHILIZED MEDICAMENT," filed Mar. 24, 2016, which claims benefit of priority to U.S. Provisional Application Ser. No. 62/137,606, entitled "Devices and Methods for Injecting a Lyophilized Medicament," filed Mar. 24, 2015, the entire disclosure of each of which is incorporated herein by reference in its entirety.

BACKGROUND

The embodiments described herein relate generally to medicament delivery devices, and more particularly to a medicament delivery device for mixing a medicament, priming a medicament container, and delivering the medicament into a body of a patient.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure. Similarly, an injection of glucagon can reduce and/or eliminate the harm potentially caused by reduced blood glucose levels in individuals who suffer from diabetes (e.g., a hypoglycemic emergency).

Because emergency medical facilities are not always available when an individual is suffering from a medical condition, some individuals carry an auto-injector, a rescue inhaler, or the like to rapidly self-administer a medicament in response to such medical conditions. Some known auto-injectors include a vial containing a liquid medicament and a spring loaded needle to automatically penetrate the user's skin and inject the medicament. The storage of certain medicaments in a liquid form, however, can result in a shorter shelf life and/or an unstable medicament. Accordingly, some known auto-injectors include a vial containing a first medicament that is separated from a second medicament. Such auto-injectors are often referred to as "wet/dry" auto-injectors, because one medicament is often a liquid (e.g., water or another diluent) and the other medicament can be substantially solid or dry (e.g., lyophilized glucagon powder). Lyophilization is also known as "freeze drying." In use, the first medicament and the second medicament must be mixed prior to injection.

Some known wet/dry injectors, however, require that the user manually actuate a mixing mechanism prior to injection (e.g., by twisting a portion of the device to complete the mixing step). Such configurations can, however, result in incomplete mixing and/or an injection occurring without mixing. In addition, the operation of some known wet/dry delivery systems includes manually inserting the needle into the skin prior to activation and subsequent medicament delivery. The operation of such configurations may also include separately attaching a needle to prepare the device for injection, resulting in a delay in delivery of the medicament. Moreover, such configurations can be complicated, making them difficult for a user to operate during an emergency or by an individual without medical training.

Some known wet/dry injectors employ a single mechanism to automatically mix and inject the medicaments contained therein. Because the mixing operation is dependent on the injection operation in such configurations, however, the medicament can be injected prior to the completion of the mixing operation and/or prior to the injector being properly positioned for the injection operation.

Some known wet/dry injectors are configured such that a user can manually vent and/or purge a portion of air included in the medicament container (e.g., mixed with or a part of the glucagon powder). In some instances, such known injectors are generally oriented in a predetermined manner (e.g., with the needle end facing upward) during the mixing process and/or prior to injection to facilitate the venting process (also referred to as "priming"). Such injectors, however, lack a locking mechanism and/or a compliance mechanism to prevent initiation of the mixing process when the injector is not properly oriented. Moreover, known some injectors are not configured to prevent an injection event from occurring prior to mixing the medicament and/or otherwise venting or priming a portion of air in the medicament container. Therefore, in many known auto-injectors, the venting process can be performed incorrectly or incompletely.

Procedures for using some known medicament delivery devices, including medical injectors and inhalers, include rapidly moving (or shaking) the device to enhance the mixing or otherwise assist in preparing the dose for delivery. Such known devices, however, do not include any mechanism for providing feedback regarding whether the medicament has been properly shaken or mixed.

Thus, a need exists for improved medicament delivery devices to improve the procedures for mixing a medicament, priming a medicament container, and delivering the medicament. Specifically, a need exists for an improved auto-injector that can separately store two or more medicaments or medicament portions and that can mix the medicaments or medicament portions and vent excess air from the medicament container prior to injecting the medicament.

SUMMARY

Medicament delivery devices for mixing a medicament and delivering the medicament are described herein. In some embodiments, an apparatus includes a housing, a safety member, and a lock member. The housing is configured to contain at least a portion of a medicament container, and includes a housing surface defining a lock chamber. The safety member is coupled to the housing and can be moved relative to the housing between a first position and a second position. The safety member is configured to limit delivery of a contents of the medicament container when the safety member is in the first position. An outer surface of the safety member is disposed outside of the housing. A lock protrusion of the safety member is disposed within the lock chamber of the housing when the safety member is in the first position. The lock protrusion is disposed outside of the lock chamber when the safety member is in the second position. The lock member is disposed within the lock chamber of the housing and is configured to move along the housing surface when an orientation of the longitudinal axis of the medicament container changes. The lock member is positioned in contact with the lock protrusion of the safety member to limit movement of the safety member from the first position to the second position when the longitudinal axis of the medicament container is in a first orientation. The lock member is spaced apart from the lock protrusion when the longitudinal axis of the medicament container is in a second orientation.

In some embodiments, an apparatus includes a housing and an electronic circuit system. The housing has an interior wall defining a volume within which at least a portion of a medicament container can be disposed. The medicament container can move within the volume to convey a medicament when a force is exerted on a portion of the medicament container. The electronic circuit system is coupled to the housing, and includes a processor, an output device, and a sensor. The sensor is configured to produce a signal received by the processor that is associated with at least one of an orientation of the housing or a movement of the housing. The electronic circuit system configured to produce an electronic output via the output device in response to the signal.

BRIEF DESCRIPTION OF THE DRAWINGS

FIGS. 14 and 15 are a front view and a top view, respectively, of the medicament delivery device of FIG. 11 in a third configuration.

FIGS. 16 and 17 are a front perspective view and a rear perspective view, respectively, of a housing included in the medicament delivery device of FIG. 11.

FIG. 20 is a cross-sectional view of the housing of FIG. 16 taken along the line $X_2$-$X_2$ in FIG. 18.

FIG. 21 is a cross-sectional view of the housing of FIG. 16 taken along the line $X_3$-$X_3$ in FIG. 19.

FIGS. 37 and 38 are a perspective view and a top view, respectively, of a carrier included in the medicament delivery device of FIG. 11.

DETAILED DESCRIPTION

Figure 1:
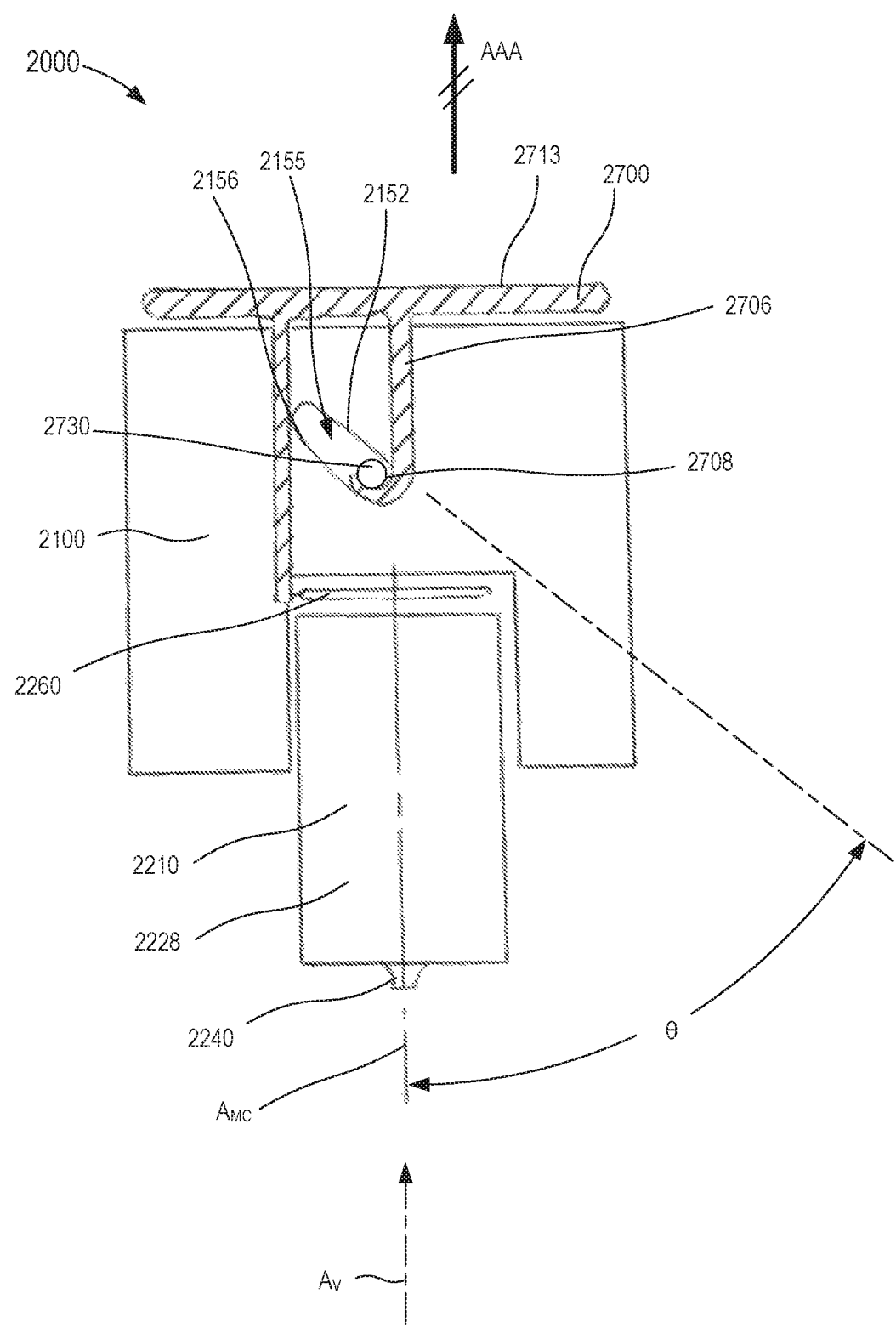
FIG. 1 is a schematic illustration of a medicament delivery device according to an embodiment in a first configuration and a first orientation.

Medicament delivery devices for mixing and/or delivering a medicament are described herein. In some embodiments, an apparatus includes an apparatus includes a housing, a safety member, and a lock member. The housing is configured to contain at least a portion of a medicament container, and includes a housing surface defining a lock chamber. The safety member is coupled to the housing and can be moved relative to the housing between a first position and a second position. The safety member is configured to limit delivery of a contents of the medicament container when the safety member is in the first position. An outer surface of the safety member is disposed outside of the housing. A lock protrusion of the safety member is disposed within the lock chamber of the housing when the safety member is in the first position. The lock protrusion is disposed outside of the lock chamber when the safety member is in the second position. The lock member is disposed within the lock chamber of the housing and is configured to move along the housing surface when an orientation of the longitudinal axis of the medicament container changes. The lock member is positioned in contact with the lock protrusion of the safety member to limit movement of the safety member from the first position to the second position when the longitudinal axis of the medicament container is in a first orientation. The lock member is spaced apart from the lock protrusion when the longitudinal axis of the medicament container is in a second orientation.

In some embodiments, the housing surface that defines the lock chamber is angularly offset from a longitudinal axis of the medicament container.

In some embodiments, the apparatus is an auto-injector that includes a medicament container within which a first medicament is stored separately from a second medicament. The first medicament can be a diluent (e.g., a liquid, such as water) and the second medicament can include an active agent. In some embodiments, the second medicament can be substantially solid or dry (e.g., glucagon powder, to form a wet/dry injector). In other embodiments, the second medicament can be liquid. In such embodiments, the contents of the medicament container delivered can include a gas from one of the medicament volumes within the medicament container. In other embodiments, the contents can include a portion of the first medicament, the second medicament, or both.

In some embodiments, an apparatus includes a housing, an energy storage member, and a safety member. The housing is configured to contain at least a portion of a medicament container. The energy storage member is disposed within the housing, and is configured to produce a force to convey a contents of the medicament container when the energy storage member is actuated to release a potential energy stored therein. The safety member is coupled to the housing. A first portion of the safety member is configured to actuate the energy storage member when the safety member is moved relative to the housing between a first position and a second position. A second portion of the safety member is configured to engage a lock member within the housing to limit movement of the safety member from the first position to the second position when the longitudinal axis of the medicament container is in a first orientation. The second portion of the safety member is spaced apart from the lock member when the longitudinal axis of the medicament container is in a second orientation.

In some embodiments, an apparatus includes a safety member configured to be coupled to a housing of a medicament delivery device. The safety member can be moved relative to the housing between a first position and a second position. A lock portion of the safety member is configured to be disposed within a lock chamber defined by the housing when the safety member is in the first position. The lock portion is configured to engage a lock member within the lock chamber to limit movement of the safety member from the first position to the second position when a longitudinal axis of the housing is in a first orientation. The lock portion is spaced apart from the lock member when the longitudinal axis of the medicament container is in a second orientation. An actuation portion of the safety member is configured to actuate an energy storage member of the medicament delivery device when the safety member is moved from the first position to the second position. The energy storage member produces a force to convey a contents from a medicament container of the medicament delivery device when the energy storage member is actuated.

In some embodiments, an apparatus includes a housing, an energy storage member, a medicament container assembly, and a flange. The housing has an interior wall defining a first portion of a boundary of a gas chamber. The energy storage member is configured to produce a pressurized gas within the gas chamber when the energy storage member is actuated to release a potential energy stored therein. The medicament container assembly is disposed within the housing, and includes a container body and an elastomeric member disposed within the container body. A surface of the elastomeric member defines a second portion of the boundary of the gas chamber. The medicament container assembly includes a delivery member coupled to a distal end portion of the container body. The flange is coupled to the container body. A proximal surface of the flange defines a third portion of the boundary of the gas chamber. An edge surface of the flange is in sliding contact with the interior wall of the housing. The flange and the container body are configured to move together within the housing from a first position to a second position in response to actuation of the energy storage member. A ratio of an area of the proximal surface of the flange to the surface of the elastomeric member is such that the elastomeric member remains in a fixed position within the container body when the flange and the container body move within the housing from the first position to the second position. In some embodiments, the ratio is greater than about two.

In some embodiments, any of the medicament delivery devices shown here can include an electronic circuit system that outputs instructions, wireless signals, or other electronic outputs in response to the user manipulating the device. In some embodiments, an apparatus includes a housing and an electronic circuit system. The housing has an interior wall defining a volume within which at least a portion of a medicament container can be disposed. The medicament container can move within the volume to convey a medicament when a force is exerted on a portion of the medicament container. The electronic circuit system is coupled to the housing, and includes a processor, an output device, and a sensor. The sensor is configured to produce a signal received by the processor that is associated with at least one of an orientation of the housing or a movement of the housing. The electronic circuit system configured to produce an electronic output via the output device in response to the signal.

In some embodiments, the sensor can be configured to produce a signal associated with a mixing of the contents within a medicament container. For example, in some embodiments, the sensor can be an optical sensor configured to detect the presence of solid particles (e.g., any unmixed lyophilized medicament) within the medicament container. In other embodiments, the electronic circuit system can produce a count-down timer or indication of time remaining until the medicament is mixed (e.g., the time remaining during which the medicament container should be shaken).

In some embodiments, an apparatus includes a housing, an actuator, a lock mechanism, and a medicament container. The actuator is at least partially disposed in the housing and is configured to be moved from a first position to a second position relative to the housing to release energy stored within an energy storage member. The lock mechanism is removably coupled to the housing to selectively maintain the actuator in the first position. The lock mechanism selectively engages a portion of the housing such that (1) the lock mechanism is maintained in a substantially fixed position when the housing is in a first orientation, and (2) the lock mechanism is removable from the housing when the housing is in a second orientation.

In some embodiments, the medicament container contains a first medicament portion and a second medicament portion. The medicament container is configured to be moved in a proximal direction within the housing in response to a first force when the lock mechanism is removed from the housing to mix the first medicament portion with the second medicament portion. The actuator is configured to be moved from the first position to the second position after the lock mechanism is removed from the housing. The medicament container is configured to move in a distal direction within the housing in response to a second force associated with the release of energy from the energy storage member.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the term "medicament" includes any constituent of a therapeutic substance. A medicament can include such constituents regardless of their state of matter (e.g., solid, liquid or gas). Moreover, a medicament can include the multiple constituents that can be included in a therapeutic substance in a mixed state, in an unmixed state and/or in a partially mixed state. A medicament can include both the active constituents and inert constituents of a therapeutic substance. Accordingly, as used herein, a medicament can include non-active constituents such as, water, colorant or the like.

The term "about" when used in connection with a referenced numeric indication means the referenced numeric indication plus or minus up to 10 percent of that referenced numeric indication. For example, "about 100" means from 90 to 110.

As used herein, the words "proximal" and "distal" refer to direction closer to and away from, respectively, an operator of the medical device. Thus, for example, the end of the medicament delivery device contacting the patient's body would be the distal end of the medicament delivery device, while the end opposite the distal end would be the proximal end of the medicament delivery device. As another example, the distal end portion of a medical injector is the end from which a needle or delivery member extends during the delivery event.

The term "parallel" is used herein to describe a relationship between two geometric constructions (e.g., two lines, two planes, a line and a plane, or the like) in which the two geometric constructions are non-intersecting as they extend substantially to infinity. For example, as used herein, a planar surface (i.e., a two-dimensional surface) is said to be parallel to a line when every point along the line is spaced apart from the nearest portion of the surface by a substantially equal distance. Similarly, a first line (or axis) is said to be parallel to a second line (or axis) when the first line and the second line do not intersect as they extend to infinity. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

The terms "perpendicular," "orthogonal," and "normal" are used herein to describe a relationship between two geometric constructions (e.g., two lines, two planes, a line and a plane, or the like) in which the two geometric constructions intersect at an angle of approximately 90 degrees within at least one plane. For example, as used herein, a line (or axis) is said to be normal to a planar surface when the line and a portion of the planar surface intersect at an angle of approximately 90 degrees within the planar surface. Two geometric constructions are described herein as being, for example, "perpendicular" or "substantially perpendicular" to each other when they are nominally perpendicular to each other, such as for example, when they are perpendicular to each other within a tolerance. Such tolerances can include, for example, manufacturing tolerances, measurement tolerances or the like.

Similarly, geometric terms, such as "parallel," "perpendicular," "cylindrical," "square," "conical," or "frusto-conical" are not intended to require absolute mathematical precision, unless the context indicates otherwise. Instead, such geometric terms allow for variations due to manufacturing or equivalent functions. For example, if an element is described as "conical" or "generally conical," a component that is not precisely conical (e.g., one that is slightly oblong) is still encompassed by this description.

Figure 2:
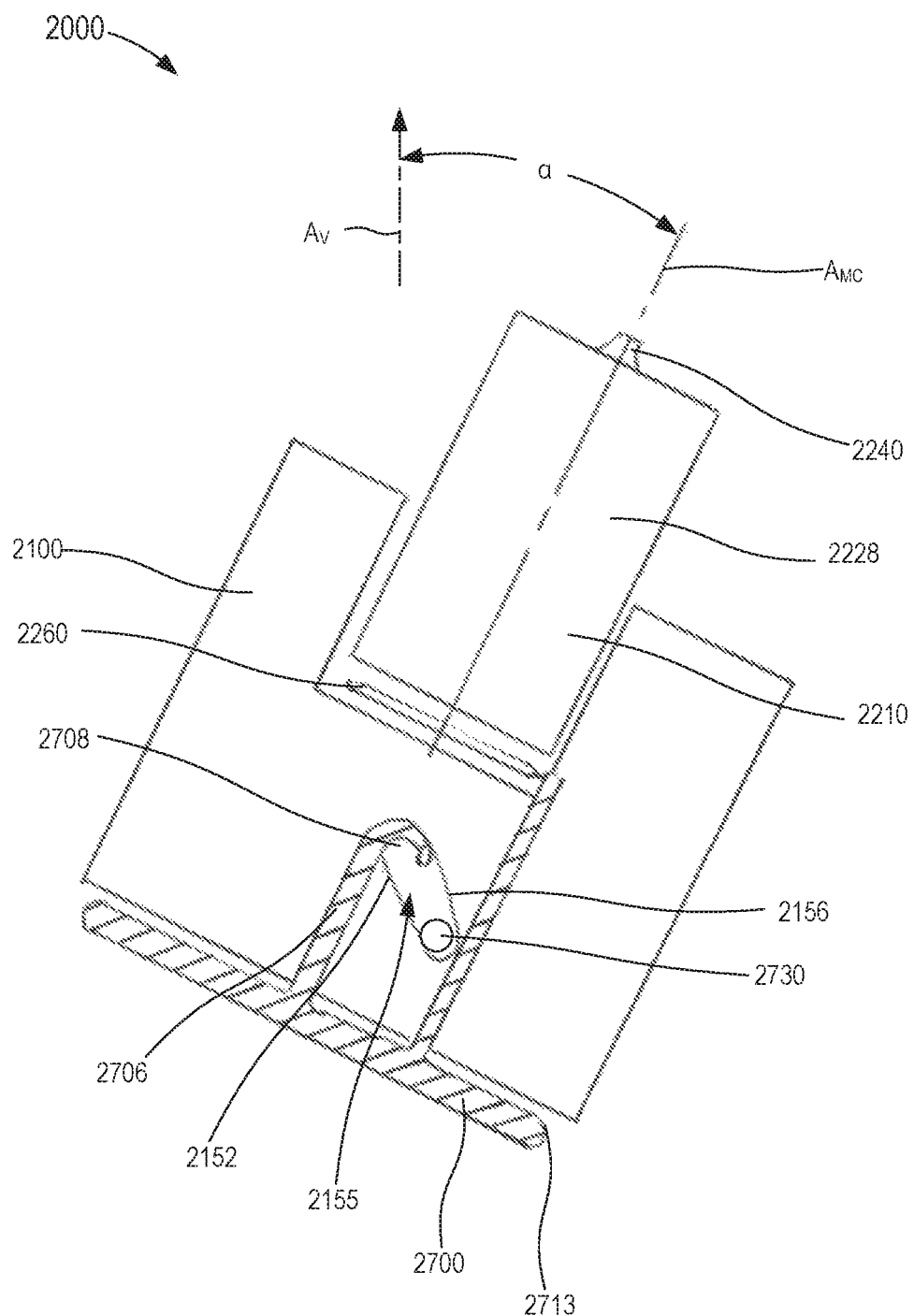
FIG. 2 is a schematic illustration of the medicament delivery device shown in FIG. 1 in a first configuration and a second orientation.
Figure 3:
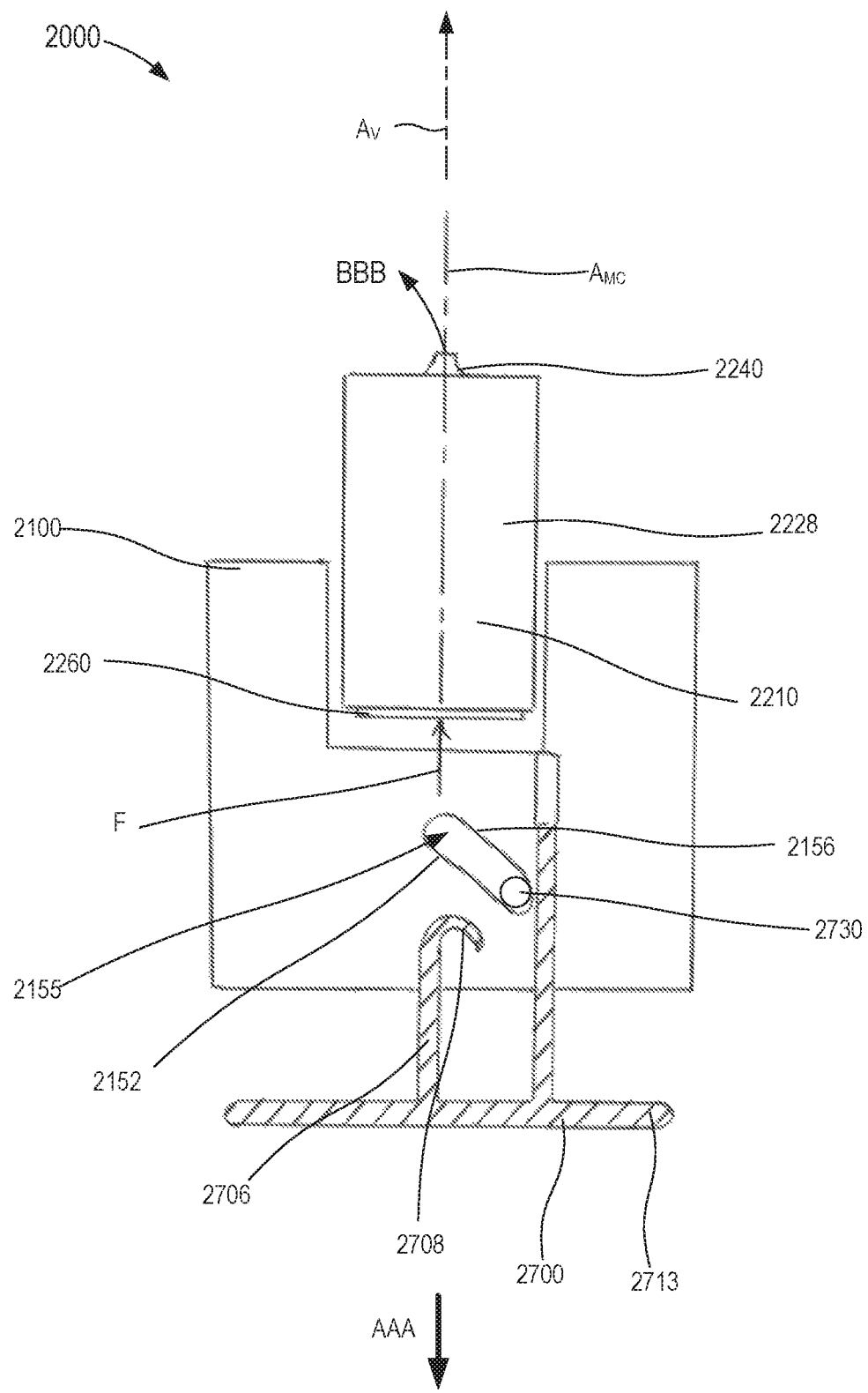
FIG. 3 is a schematic illustration of the medicament delivery device shown in FIG. 1 in a second configuration and a third orientation.

FIGS. 1-3 are schematic illustrations of a medicament delivery device 2000 according to an embodiment in various configurations and orientations. The orientation of the device 2000 (and any of the other devices shown herein) can be described with reference to an upward vertical axis $A_V$, which is an axis having a direction opposite that of the direction of gravity. The medicament delivery device 2000 includes a housing 2100, a safety member 2700, and a lock member 2730. The housing 2000 can be any suitable structure within which at least a portion of a medicament container 2210 can be disposed. The housing 2100 can be, for example, a housing of a single-use auto-injector within which the medicament container 2210 is fully disposed. In other embodiments, the housing 2100 can be a housing of a reusable auto-injector, within which multiple different medicament containers can be disposed and actuated as a part of a dosage regimen. In yet other embodiments, the housing 2100 can be a housing of a pen injector. In yet other embodiments, the housing 2100 can be an inhaler housing within which a distal end portion of the medicament container 2210 is disposed.

The housing 2100 (and any of the housings described herein) can be constructed from any suitable materials, such as plastic (including thermoplastics such as cyclic olefin copolymers). In some embodiments, the housing 2100 can be monolithically constructed. In other embodiments, the housing 2100 (and any of the housing described herein) can be constructed of multiple components that can be coupled together (such as the housing 1100 described below).

As shown, the housing 2100 defines a volume within which a portion of the medicament container 2210 can be disposed. The medicament container 2210 defines a longitudinal axis $A_{MC}$, and includes a delivery member 2240 (e.g., a needle, a nozzle, a mouthpiece, or a valve) through which the contents 2228 contained therein can be conveyed. The medicament container 2210 can be any suitable medicament container, such as, for example a pre-filled cartridge, a vial, an ampule, a pre-filled syringe, or the like. In some embodiments, the medicament container 2210 can be a container within which a first medicament is stored separately from a second medicament. The first medicament can be a diluent (e.g., a liquid, such as water) and the second medicament can include an active agent. In some such embodiments, the second medicament can be substantially solid or dry (e.g., glucagon powder, to form a wet/dry injector). In other embodiments, the second medicament can be liquid. In still other embodiments, the medicament container 2210 can be a drug canister containing a propellant and a medicament, and the housing 2100 can be an inhaler housing. The contents 2228 can a liquid medicament, a gas from one of the medicament volumes within the medicament container (e.g., excess air from the lyophilized medicament), a combination of a liquid and a gas, or a propellant.

The housing 2100 includes a housing surface 2152 that defines a lock chamber 2155 within the housing 2100. As described in more detail below, the lock chamber 2155 contains the lock member 2730. In some embodiments, the housing surface 2152 is angularly offset from the longitudinal axis $A_{MC}$ of the medicament container 2210 when the medicament container 2210 is disposed within the housing 2100. Similarly stated, in some embodiments, a tangent line of the housing surface 2152 and the longitudinal axis $A_{MC}$ of the medicament container 2210 form an angle greater than zero degrees and less than 90 degrees. Specifically, as shown in FIG. 1, in some embodiments, the tangent line of the housing surface 2152 and the longitudinal axis $A_{MC}$ form an angle θ that is non-parallel with and not normal to the longitudinal axis $A_{MC}$. In this manner, as described below, the lock member 2730 can move along the housing surface 2152 when the medicament container 2210 is within a desired orientation range or when the medicament container 2210 changes orientation relative to the upward vertical axis $A_V$.

In some embodiments, the lock chamber 2155 can be defined by more than one housing surface. For example, in some embodiments, the housing can include multiple, discontinuous surfaces that collectively define the lock chamber 2155 such that the movement of the lock member 2730 follows a desired path when the medicament container 2210 changes orientation relative to the upward vertical axis $A_V$. For example, as shown in FIGS. 1-3, in some embodiments, the housing 2100 can include a second housing surface 2156 that, along with the first housing surface 2152, defines the lock chamber 2155. In some embodiments, the second housing surface 2156 can be opposite to and/or substantially parallel to the first housing surface 2152. In other embodiments, the second housing surface 2156 can form a non-zero angle (i.e., can be non-parallel to) the first housing surface 2152. In this manner, the lock member can move along either of the first housing surface 2152 or the second housing surface 2156 when the orientation of the longitudinal axis $L_{MC}$ of the medicament container changes.

The safety member 2700 is movably coupled to the housing 2100, and is configured to limit the delivery of the contents 2228 from the medicament container 2210. As shown in FIG. 1, the safety member 2700 includes an outer surface 2713 and a lock protrusion (or lock portion) 2706. The safety member 2700 is coupled to the housing 2100 such that the outer surface 2713 is disposed outside of the housing 2100. Thus, in use, the safety member 2700 can be manipulated via the outer surface 2713 to be moved relative to the housing 2100 to enable delivery of the contents 2228 from the medicament container 2210. In some embodiments, the outer surface 2713 can include ribs, protrusions, or a surface texture to facilitate a user manipulating the safety member 2700. In some embodiments, the outer surface 2713 can include visual indicia (symbols, arrows, text, etc.).

The lock protrusion 2706 is disposed within the lock chamber 2155 of the housing 2100 when the safety member is in a first position, as shown in FIG. 1. In this manner, depending on the orientation of the housing 2100 and/or the medicament container 2210, the lock protrusion 2706 can be in contact with the lock member 2730 to limit movement of the safety member 2700 relative to the housing 2100. This arrangement allows for the safety member 2700 to be removed only when the housing 2100 and/or the medicament container 2210 are within a desired orientation range. In some embodiments, for example, the lock protrusion 2706 can include a recessed portion 2708 (or "hook") that receives the lock member 2730 when the longitudinal axis $A_{MC}$ of the medicament container 2210 is in a desired orientation.

In use, the safety member 2700 can be moved between a first position (see FIG. 1) and a second position (see FIG. 3). Moreover, the device 2000 (including the housing 2100 and the longitudinal axis $A_{MC}$ of the medicament container 2210) can be moved between at least two orientations. Said another way, the device 2000 can be rotated such that the longitudinal axis $A_{MC}$ of the medicament container 2210 rotates relative to the upward vertical axis $A_V$. FIG. 1 shows the device 2000 having the safety member 2700 in the first position (i.e., attached to the housing 2100 such that the lock protrusion 2706 is disposed within the lock chamber 2155) and in a first orientation. Specifically, the medicament container 2210 is pointed downwards (i.e., the longitudinal axis $A_{MC}$ of the medicament container 2210 forms an angle of about 180 degrees with the upward vertical axis $A_V$). When the medicament container 2210 and/or housing 2100 are in the first orientation, the lock protrusion 2706 is in contact with the lock member 2730, and the lock member 2730 is retained within the lock chamber 2155. This arrangement prevents the safety member 2700 from being moved to the second position (as indicated by the arrow AAA in FIG. 1).

FIG. 2 shows the device 2000 having the safety member 2700 in the first position (i.e., attached to the housing 2100 such that the lock protrusion 2706 is disposed within the lock chamber 2155) and in a second orientation. Specifically, the orientation of the medicament container 2210 has changed such that the longitudinal axis $A_{MC}$ of the medicament container 2210 forms an angle α with the upward vertical axis $A_V$. As shown in FIG. 2, the lock member 2730 moves along the housing surface 2152 when the orientation of the longitudinal axis $A_{MC}$ of the medicament container 2210 changes such that the lock member 2730 is no longer in contact with the lock protrusion 2706. Thus, when the device 2000 is in the second orientation, the safety member 2700 can be moved from its first position to its second position. Similarly stated, the lock member 2730 is disengaged from the lock protrusion 2706, and the safety member 2700 is no longer retained by the lock member 2730.

FIG. 3 shows the device 2000 having the safety member 2700 in the second position (i.e., attached to the housing 2100 but with the lock protrusion 2706 no longer within the lock chamber 2155) and in a third orientation. Specifically, the orientation of the medicament container 2210 has changed such that the longitudinal axis $A_{MC}$ of the medicament container 2210 is pointed directly upwards (i.e., it forms an angle of about zero degrees with the upward vertical axis $A_V$). As shown by the arrow AAA in FIG. 3, the safety member 2700 can be moved relative to the housing 2100 to enable delivery of the contents 2228 of the medicament container 2210 (shown by the arrow BBB). Thus, when the device 2000 is in a range of orientations, including at least the second orientation and the third orientation, the safety member 2700 can be moved from its first position to its second position. Further, upon removal of the safety member 2700, a force F can be exerted on the medicament container 2210 (e.g. via a movable member 2260) to deliver at least a portion of the contents 2228.

In some embodiments, the contents 2228 can include a gas from within the medicament container 2210, and the orientation range can be within ±15 degrees from the upward vertical axis $A_V$. In this manner, the medicament container 2210 can be properly primed (or bled) when the delivery member 2240 is pointing in a generally upward direction to allow the gas to escape. Because the safety member 2700 cannot be removed when the delivery member 2240 is pointing downward (e.g., FIG. 1), an orientation in which the gas cannot easily escape, the arrangement of the safety member 2700 described above prevents the initiation of the priming step. The orientation range can be any suitable orientation range. For example, in some embodiments, the orientation range can be within ±25 degrees from the upward vertical axis $A_V$, within ±30 degrees from the upward vertical axis $A_V$, within ±35 degrees from the upward vertical axis $A_V$, or within ±40 degrees from the upward vertical axis $A_V$.

Although the safety member 2700 is shown as being coupled to the housing 2100 when in its second position (e.g., FIG. 3), in other embodiments, the safety member 2700 can be removed from the housing 2100 when in its second position.

Although the housing 2100 is shown as including a housing surface 2152 that is substantially linear (or flat), in other embodiments, the housing surface 2152 can have any suitable shape. For example, in some embodiments, the housing surface 2152 can have a conical shape, and the lock member 2730 can have a spherical shape, such that the lock member 2730 can roll along the conical surface 2152.

The force F can be applied by any suitable means. For example, in some embodiments, the user can apply the force manually, such as by squeezing the housing 2100, depressing the medicament container 2210, pushing a piston against an elastomeric member (not shown) within the medicament container 2210, or the like. In other embodiments, the force F can be applied by an energy storage member (not shown) disposed within the housing 2100. In some such embodiments, the safety member can include an actuation portion configured to actuate the energy storage member when the safety member is moved.

Figure 4:
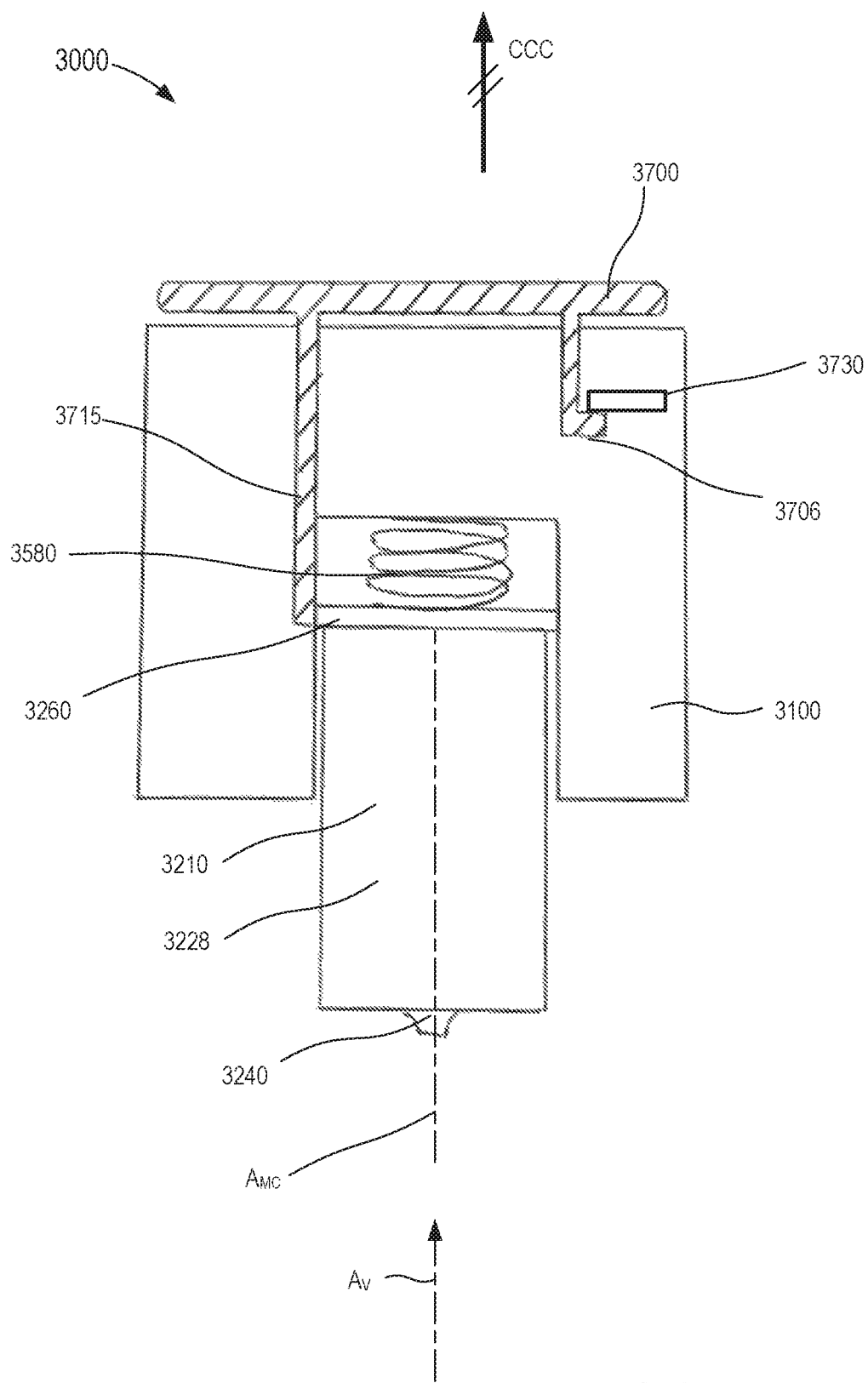
FIG. 4 is a schematic illustration of a medicament delivery device according to an embodiment in a first configuration and a first orientation.
Figure 5:
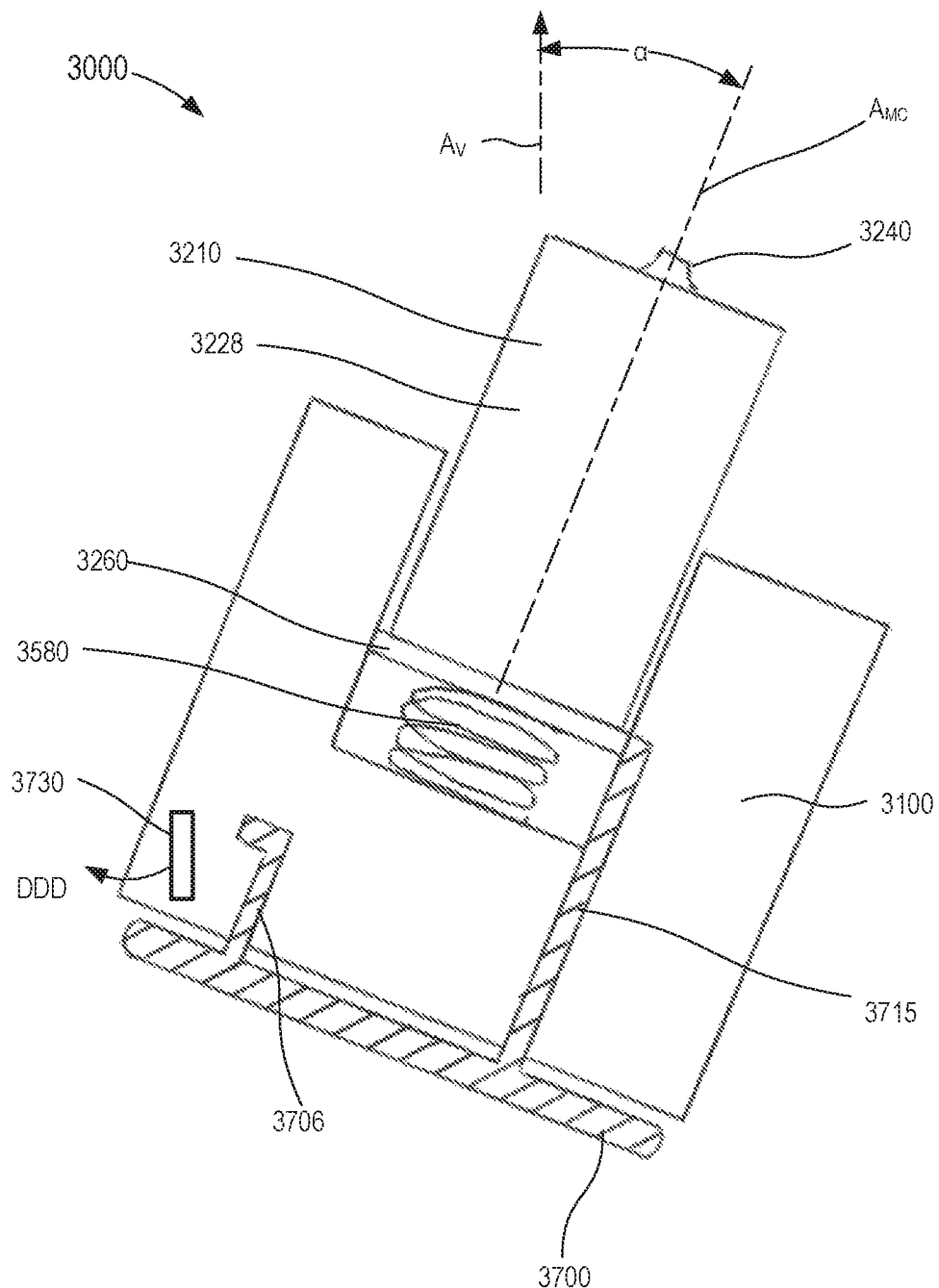
FIG. 5 is a schematic illustration of the medicament delivery device shown in FIG. 4 in a first configuration and a second orientation.
Figure 6:
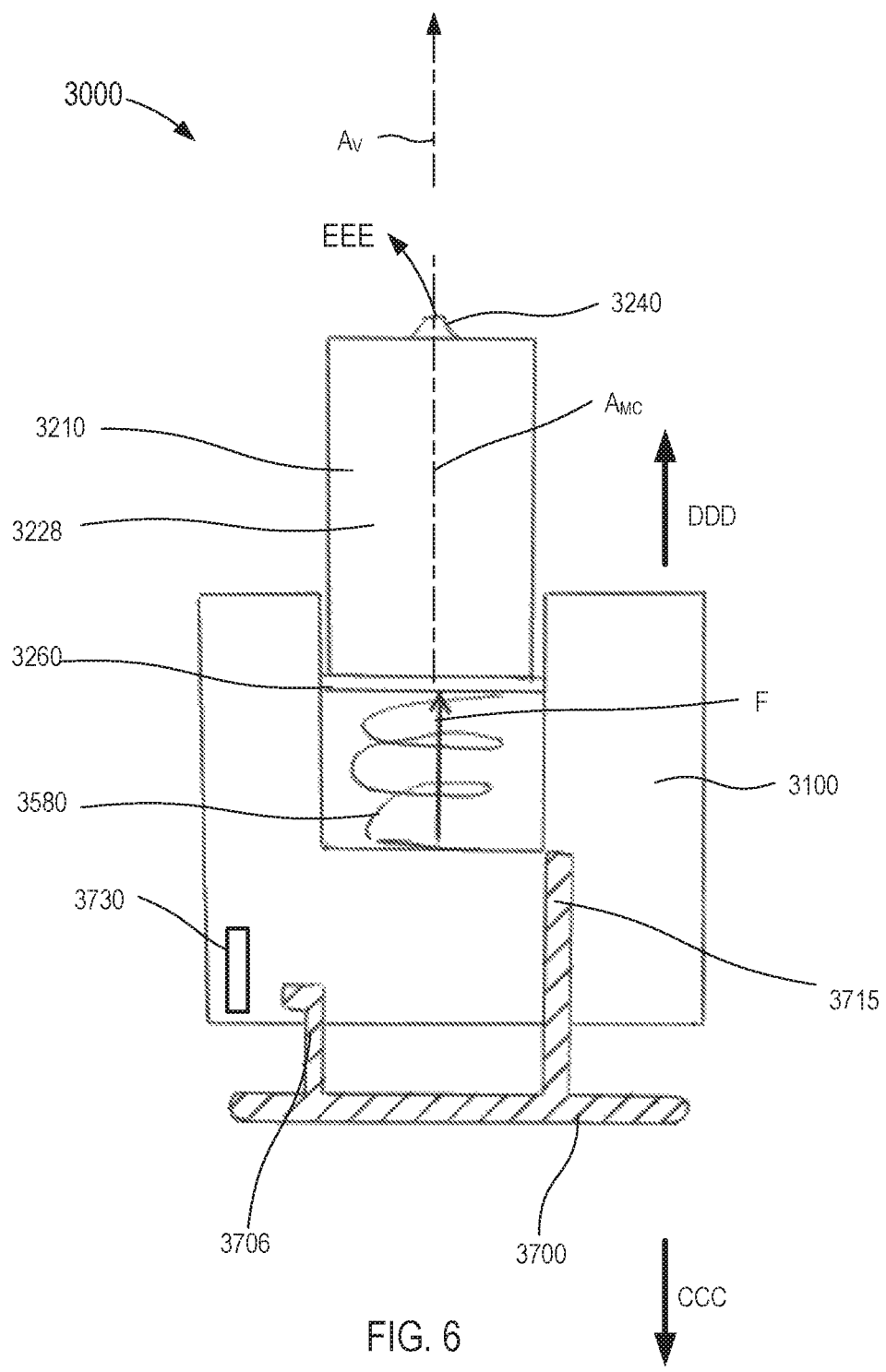
FIG. 6 is a schematic illustration of the medicament delivery device shown in FIG. 4 in a second configuration and a third orientation.
Figure 7:
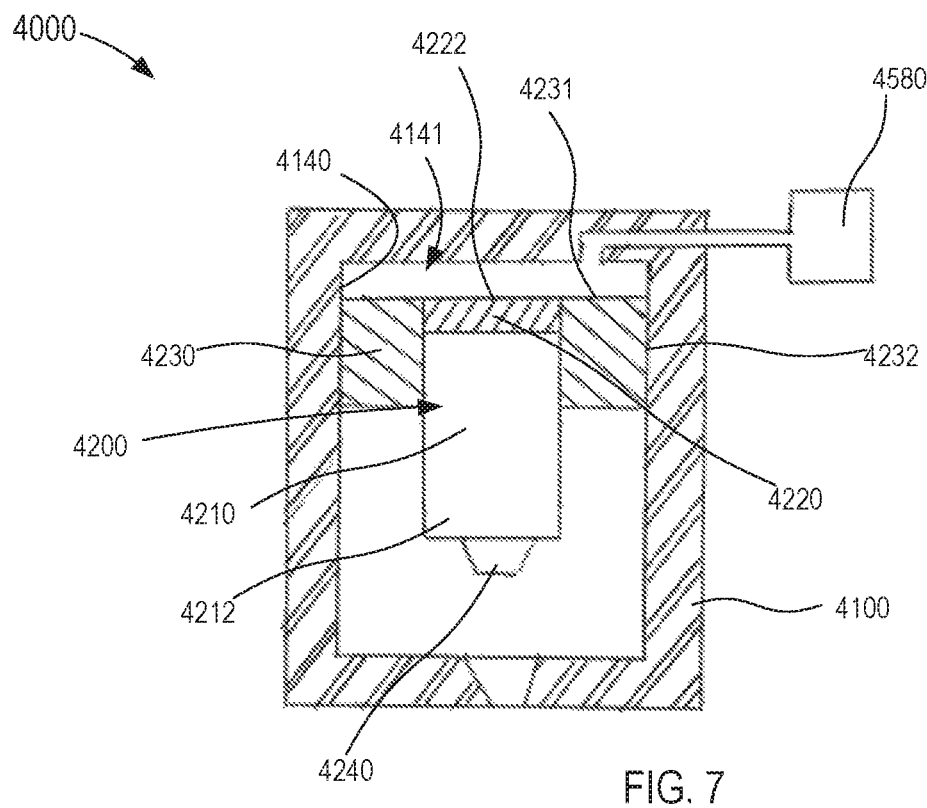
FIGS. 7-9 are schematic illustrations of a medicament delivery device according to an embodiment in a first configuration, a second configuration, and a third configuration, respectively.
Figure 8:
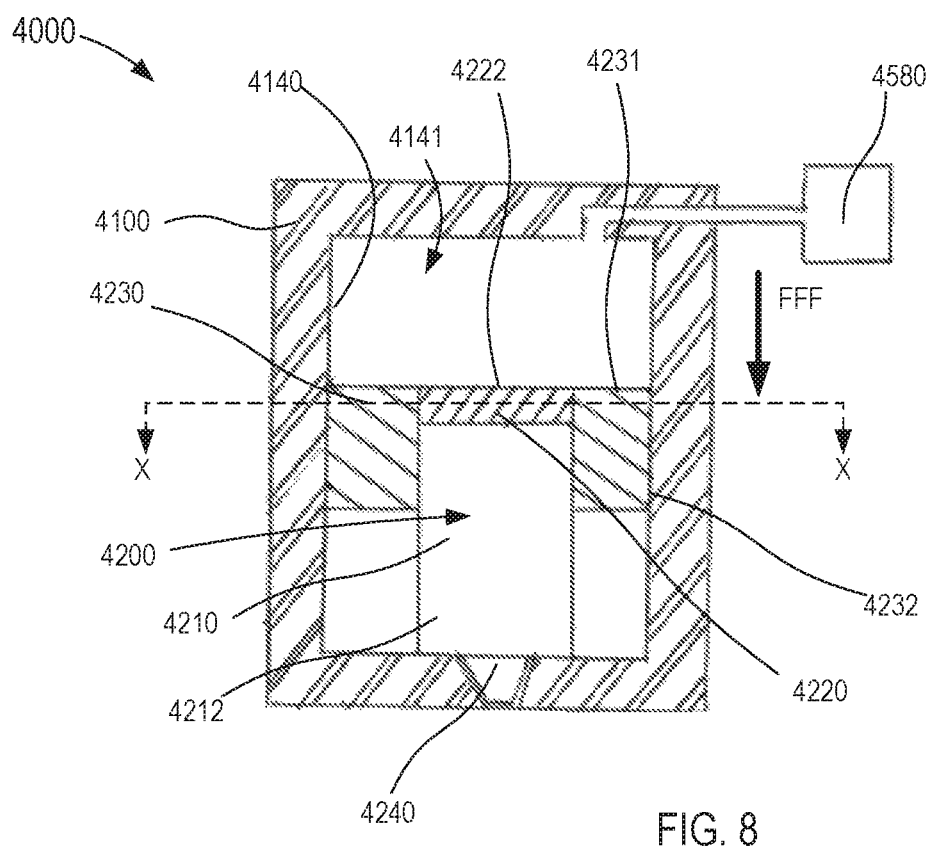
Figure 9:
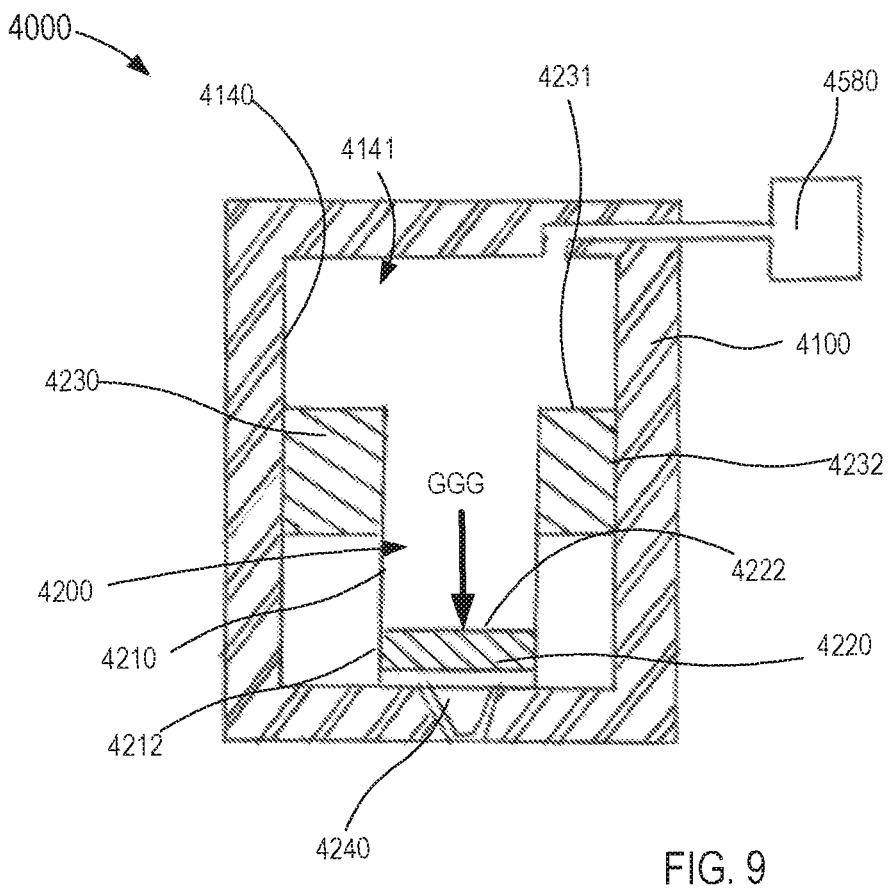

For example, FIGS. 4-6 show a medicament delivery device 3000 according to an embodiment in various configurations and orientations. The orientation of the device 3000 (and any of the other devices shown herein) can be described with reference to an upward vertical axis $A_V$, which is an axis having a direction opposite that of the direction of gravity. The medicament delivery device 3000 includes a housing 3100, a safety member 3700, a lock member 3730, and an energy storage member 3580. The housing 3000 can be any suitable structure within which at least a portion of a medicament container 3210 can be disposed. The housing 3100 can be, for example, a housing of a single-use auto-injector within which the medicament container 3210 is fully disposed. In other embodiments, the housing 3100 can be a housing of a reusable auto-injector, within which multiple different medicament containers can be disposed and actuated as a part of a dosage regimen. In yet other embodiments, the housing 3100 can be a housing of a pen injector. In yet other embodiments, the housing 3100 can be an inhaler housing within which a distal end portion of the medicament container 3210 is disposed.

As shown, the housing 3100 defines a volume within which a portion of the medicament container 3210 can be disposed. The medicament container 3210 defines a longitudinal axis $A_{MC}$, and includes a delivery member 3240 through which the contents 3228 contained therein can be conveyed. The medicament container 3210 can be any suitable medicament container, such as, for example a pre-filled cartridge, a vial, an ampule, a pre-filled syringe, or the like. In some embodiments, the medicament container 3210 can be a container within which a first medicament is stored separately from a second medicament. The first medicament can be a diluent (e.g., a liquid, such as water) and the second medicament can include an active agent. In some such embodiments, the second medicament can be substantially solid or dry (e.g., glucagon powder, to form a wet/dry injector). In other embodiments, the second medicament can be liquid. In still other embodiments, the medicament container 3210 can be a drug canister containing a propellant and a medicament, and the housing 3100 can be an inhaler housing. The contents 3228 can a liquid medicament, a gas from one of the medicament volumes within the medicament container, a combination of a liquid and a gas, or a propellant.

In some embodiments, the lock member 3730 can be disposed within the housing 3100. In such embodiments, the lock member 3730 can move within the housing 3100 to selectively engage the safety member 3700, as described in more detail below. In other embodiments, the lock member 3730 can be coupled to the housing 3100 (e.g., on an outer surface of the housing), and can move relative to the housing 3100 to selectively engage the safety member 3700.

The energy storage member 3580 is disposed within the housing 3100, and is configured to produce a force F (see FIG. 6) to convey the contents 3228 of the medicament container 3210 when the energy storage member 3580 is actuated to release a potential energy stored therein. The energy storage member 3580 can be any suitable member or device that stores potential energy and, when actuated, releases the energy to produce a force. For example, the energy storage member can be any of a gas container, a chemical energy storage member, a spring, or an electrical energy storage member.

The safety member 3700 is movably coupled to the housing 3100, and is configured to actuate the energy storage member 3580 when the safety member 3700 is moved relative to the housing 3100 between a first position (FIG. 4) and a second position (FIG. 6). As shown, the safety member 3700 includes a first portion 3715 and a second portion 3706. The first portion 3715 engages a movable member 3260 (e.g., a carrier, a retention member, or the like) when the safety member 3700 is in one of the first position or the second position. When the safety member 3700 is moved from the first position (FIG. 4) to the second position (FIG. 6), the first portion 3715 actuates the movable member 3260 and/or the energy storage member 3580 to produce the force F, as shown in FIG. 6.

The second portion 3706 of the safety member 3700 can be engaged with the lock member 3730 when the safety member 3700 is in a first position to limit movement of the safety member 3700 relative to the housing 3100, as shown in FIG. 4. Moreover, depending on the orientation of the housing 3100 and/or the medicament container 3210, the second portion 3706 can be either be in contact with the lock member 3730 to limit movement of the safety member 3700 relative to the housing 3100, or can be spaced apart from the lock member 3730. This arrangement allows for the safety member 3700 to be removed only when the housing 3100 and/or the medicament container 3210 are within a desired orientation range. In some embodiments, for example, the second portion 3706 can include a recessed portion (not shown) that receives the lock member 3730 when the longitudinal axis $A_{MC}$ of the medicament container 3210 is in a desired orientation.

In use, the safety member 3700 can be moved between a first position (see FIG. 4) and a second position (see FIG. 6, as shown by the arrow CCC). Moreover, the device 3000 (including the housing 3100 and the longitudinal axis $A_{MC}$ of the medicament container 3210) can be moved between at least two orientations. Said another way, the device 3000 can be rotated such that the longitudinal axis $A_{MC}$ of the medicament container 3210 rotates relative to the upward vertical axis $A_V$. FIG. 4 shows the device 3000 having the safety member 3700 in the first position (i.e., attached to the housing 3100) and in a first orientation. Specifically, the medicament container 3210 is pointed downwards (i.e., the longitudinal axis $A_{MC}$ of the medicament container 3210 forms an angle of about 180 degrees with the upward vertical axis $A_V$). When the medicament container 3210 and/or housing 3100 are in the first orientation, the second portion 3706 is in contact with the lock member 3730. This arrangement prevents the safety member 3700 from being moved to the second position (as indicated by the arrow CCC in FIG. 4).

FIG. 5 shows the device 3000 having the safety member 3700 in the first position (i.e., attached to the housing 3100) and in a second orientation. Specifically, the orientation of the medicament container 3210 has changed such that the longitudinal axis $A_{MC}$ of the medicament container 3210 forms an angle α with the upward vertical axis $A_V$. As shown in FIG. 3, the lock member 3730 moves (as shown by the arrow DDD in FIG. 5) when the orientation of the longitudinal axis $A_{MC}$ of the medicament container 3210 changes such that the lock member 3730 is no longer in contact with the second portion 3706. Thus, when the device 3000 is in the second orientation, the safety member 3700 can be moved from its first position to its second position.

FIG. 6 shows the device 3000 having the safety member 3700 in the second position, and with the device 3000 in a third orientation. Specifically, the orientation of the medicament container 3210 has changed such that the longitudinal axis $A_{MC}$ of the medicament container 3210 is pointed directly upwards (i.e., it forms an angle of about zero degrees with the upward vertical axis $A_V$). As shown by the arrow CCC in FIG. 6, the safety member 3700 can be moved relative to the housing 3100 to actuate the energy storage member 3580. This, in turn, produces the force F to deliver of the contents 3228 of the medicament container 3210 (shown by the arrow EEE). Thus, when the device 3000 is in a range of orientations, including at least the second orientation and the third orientation, the safety member 3700 can be moved from its first position to its second position. Further, upon removal of the safety member 3700, a force F produced by the energy storage member 3580 can be exerted on the medicament container 3210 (e.g. via a movable member 3260) to deliver at least a portion of the contents 3228.

In some embodiments, the contents 3228 can include a gas from within the medicament container 3210, and the orientation range can be within ±15 degrees from the upward vertical axis $A_V$. In this manner, the medicament container 3210 can be properly primed (or bled) when the delivery member 3240 is pointing in a generally upward direction to allow the gas to escape. Because the safety member 3700 cannot be removed when the delivery member 3240 is pointing downward (e.g., FIG. 1), an orientation in which the gas cannot easily escape, the arrangement of the safety member 3700 described above prevents the initiation of the priming step. The orientation range can be any suitable orientation range. For example, in some embodiments, the orientation range can be within ±25 degrees from the upward vertical axis $A_V$, within ±30 degrees from the upward vertical axis $A_V$, within ±35 degrees from the upward vertical axis $A_V$, or within ±40 degrees from the upward vertical axis $A_V$.

Although the safety member 3700 is shown as being coupled to the housing 3100 when in its second position (e.g., FIG. 6), in other embodiments, the safety member 3700 can be removed from the housing 3100 when in its second position.

In some embodiments, the housing 3100 can define a lock chamber (not shown) within which the lock member 3730 is disposed. The lock chamber can be similar to the lock chamber 2155 shown and described above.

In some embodiments, a medical injector can include a fluid system to produce a force to move a medicament container and/or to move an elastomeric member within the medicament container to deliver a medicament therein. Such fluid systems can be hydraulic or gas-based. Moreover, in some embodiments, such medical injectors can be devoid of a rigid member that transfers the force produced by the pressurized fluid onto the surface of the medicament container and/or elastomeric member. Said another way, in some embodiments, a medical injector can be a "pistonless" design that does not require a rigid member to apply force onto the fluid and/or elastomeric member in order to deliver fluid from the medicament container. Such arrangements can produce a more compact (smaller) form factor when compared to devices that employ a rigid member to deliver the fluid from the medicament container.

As one example, FIGS. 7-10 show a medicament delivery device 4000 according to an embodiment in various configurations. The medicament delivery device 4000 includes a housing 4100, a medicament container assembly 4200, a flange 4230, and an energy storage member 4580. The housing 4000 can be any suitable structure within which at least a portion of the medicament container 4210 can be disposed. The housing 4100 can be, for example, a housing of an auto-injector within which the medicament container 4210 is fully disposed. In other embodiments, the housing 4100 can be a housing of a reusable auto-injector, within which multiple different medicament containers can be disposed and actuated as a part of a dosage regimen. In yet other embodiments, the housing 4100 can be a housing of a pen injector.

As shown, the housing 4100 includes an interior wall 4140 that defines a first portion of a boundary of a gas chamber 4141. The gas chamber 4141 is a volume within which a portion of the pressurized gas from the energy storage member 4580 is conveyed when the energy storage member 4580 is actuated. As described in more detail below, the gas chamber 4141 is also the volume within which a portion of the medicament container 4210 is movably disposed.

The medicament container assembly 4200 includes a container body 4210, an elastomeric member 4220, and a delivery member 4240 (coupled to a distal end portion 4212). The delivery member 4240 is the structure through which the contents contained within the container body 4210 can be conveyed. The delivery member 4240 can be any suitable member, such as a needle, a nozzle, or a valve, through which the contents contained of the container body 4210 can be conveyed.

The elastomeric member 4220 is disposed within the container body 4210 and defines a portion of the medicament volume within the container body 4210. The elastomeric member 4220 forms a substantially fluid-tight seal with the container body 4210 such that when a force is exerted on the elastomeric member 4220 that is sufficient to move the elastomeric member 4220 within the container body 4210, the contents therein will be conveyed via the delivery member 4240. As shown, the elastomeric member 4220 includes a surface 4222 that defines a second portion of the boundary of the gas chamber 4141.

The elastomeric member 4220 can be of any design or formulation suitable for contact with the medicament (e.g., a diluent, a liquid medicament, or a lyophilized medicament). For example, the elastomeric member 4220 can be formulated to minimize any reduction in the efficacy of the medicament that may result from contact (either direct or indirect) between the elastomeric member 4220 and the medicament. In some embodiments, the elastomeric member 4220 can be made from and/or can include butyl rubber, such as chlorobutyl rubber, bromobutyl rubber, and/or the like. In some embodiments, the elastomeric member 4220 can be formulated to minimize any leaching or out-gassing of compositions that may have an undesired effect on the medicament.

The medicament container 4210 can be any suitable medicament container, such as, for example a pre-filled cartridge, a vial, an ampule, a pre-filled syringe, a Crystal Zenith® container, or the like. In some embodiments, the medicament container 4210 can be a container within which a first medicament is stored separately from a second medicament. The first medicament can be a diluent (e.g., a liquid, such as water) and the second medicament can include an active agent. In some such embodiments, the second medicament can be substantially solid or dry (e.g., glucagon powder, to form a wet/dry injector). In other embodiments, the second medicament can be liquid.

The flange 4230 is coupled to the container body 4210, and includes a proximal surface 4231 and an edge surface 4232. The proximal surface 4231 defines a third portion of the boundary of the gas chamber 4141. In this manner, the interior wall 4140 of the housing 4100, the surface 4222 of the elastomeric member 4220, and the proximal surface 4231 of the flange 4230 are exposed to the pressurized gas (and thus, the same pressure) during normal use. The edge surface 4232 of the flange 4230 is in sliding contact with the interior wall 4140. Thus, in use, the flange 4230 and the container body 4210 move together within the housing 4100 from a first position (FIG. 7) to a second position (FIGS. 8 and 9) in response to actuation of the energy storage member 4580.

Figure 10:
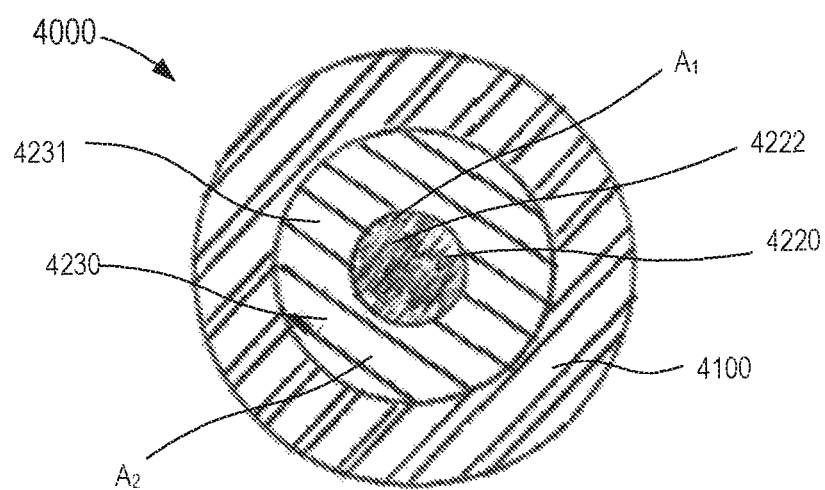
FIG. 10 is a cross-section view of the medicament delivery device shown in FIG. 8 taken along the line X-X in FIG. 8.

Moreover, as shown in FIG. 10, the area $A_1$ of the surface 4222 of the elastomeric member 4220 is sized such that when the pressurized gas is conveyed into the gas chamber 4141, the resulting force exerted on the surface 4222 is insufficient to move the elastomeric member 4220 within the container body 4210 when the flange 4230 and the container body 4210 are moving from the first position to the second position. Similarly stated, a ratio of an area $A_2$ of the proximal surface 4231 of the flange 4230 (including the area $A_1$) to the area $A_1$ of the surface 4222 of the elastomeric member 4220 is such that the elastomeric member 4220 remains in a fixed position within the container body 4210 when the flange 4230 and the container body 4201 move within the housing 4100 from the first position to the second position, as shown by the arrow FFF in FIG. 8. When the medicament container assembly 4200 reaches the second position (FIG. 8), a portion of the container body 4210 engages a surface, protrusion, or end-stop. The continued increase of the gas pressure (due in part to the fixed volume of the gas chamber 4141) then causes the elastomeric member 4220 to move, as shown by the arrow GGG in FIG. 9.

In some embodiments, the area ratio is greater than about 2. In other embodiments, the area ratio is greater than about 2.5. In other embodiments, the area ratio is greater than about 3.0.

In some embodiments, the flange 4230 can include a valve, bore, or other mechanism to release the gas pressure from within the gas chamber 4141. In this manner, the flange 4230 and the container assembly 4200 can be moved proximally (e.g., retracted) after delivery of the medicament. In some embodiments, for example, the flange 4230 can define a bore that is continuously opened, and that releases the gas pressure during the insertion and injection event. The bore can be sized such that the amount of pressure released from the gas chamber 4141 does not impede the insertion and injection operations.

Figure 11:
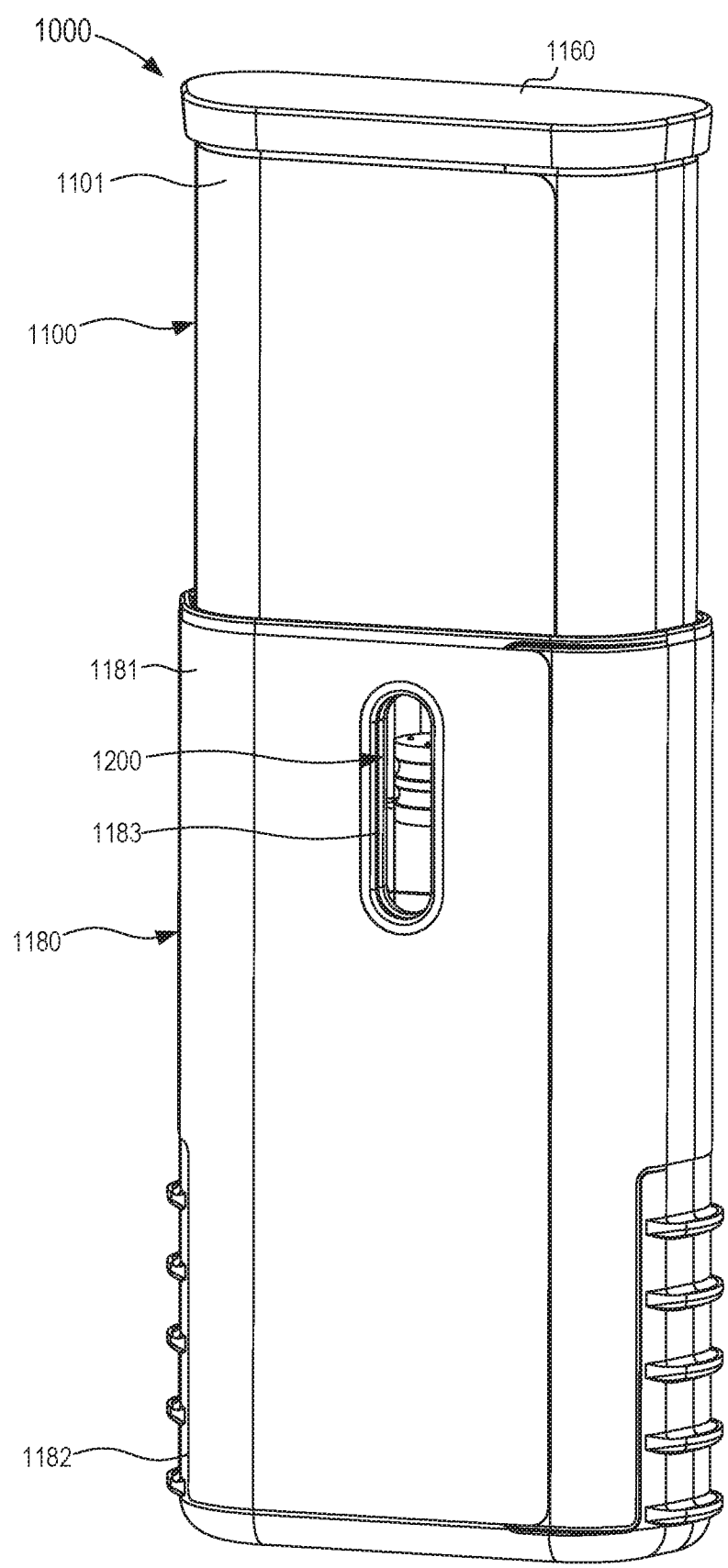
FIG. 11 is a perspective view of a medicament delivery device according to an embodiment in a first configuration.
Figure 12:
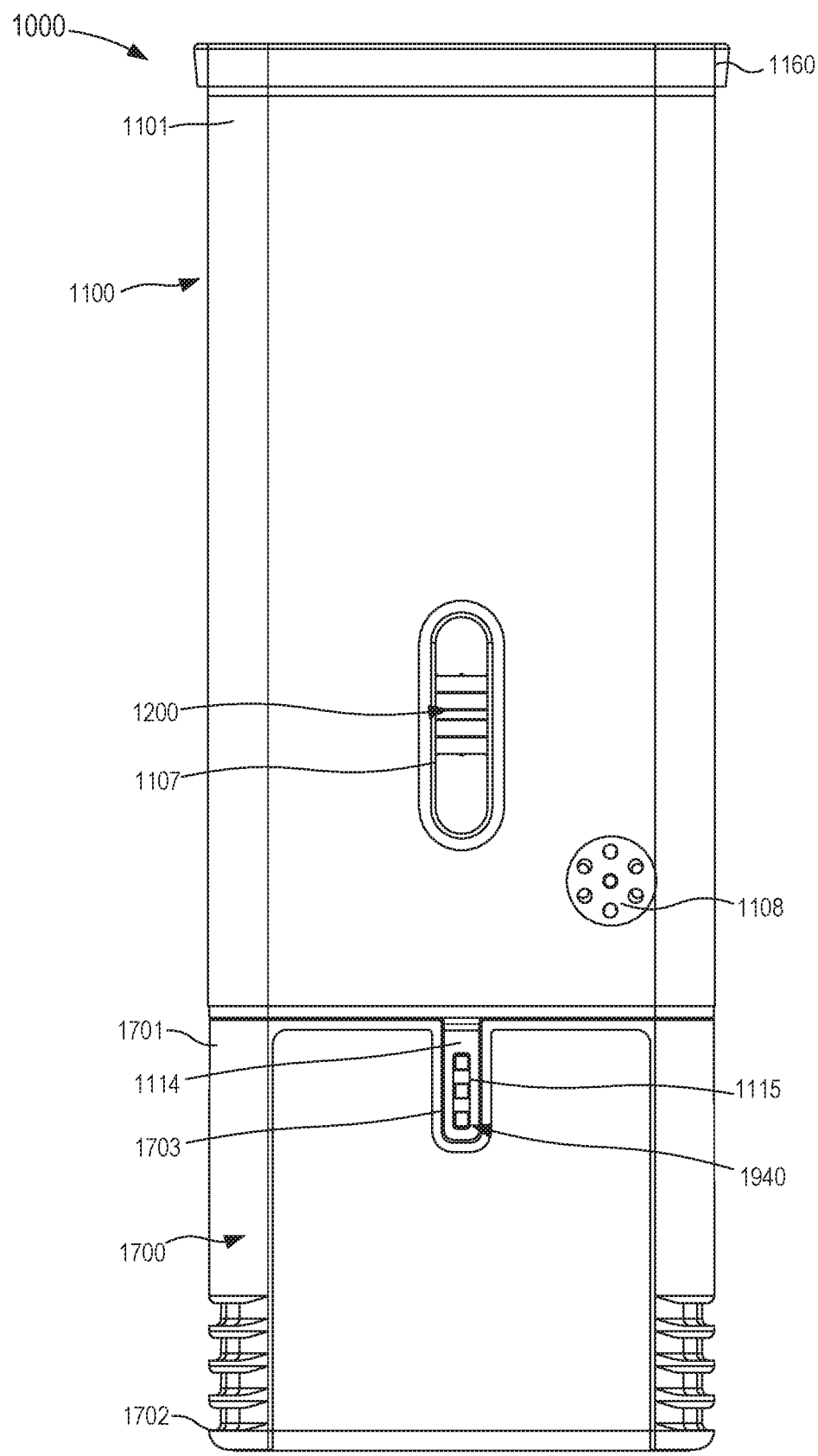
FIGS. 12 and 13 are a front view and a rear view, respectively, of the medicament delivery device of FIG. 11 in a second configuration.
Figure 13:
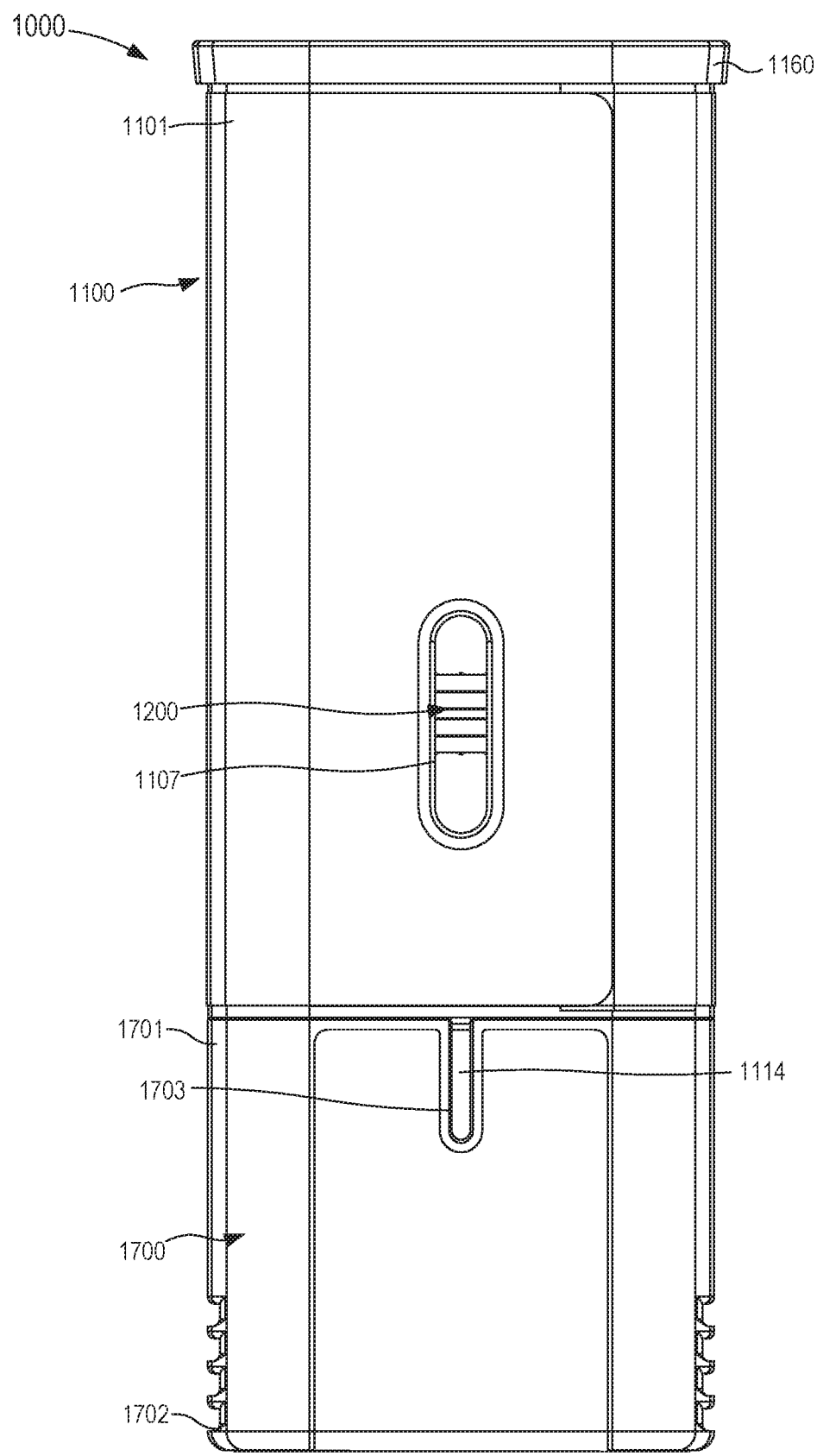
Figure 64:
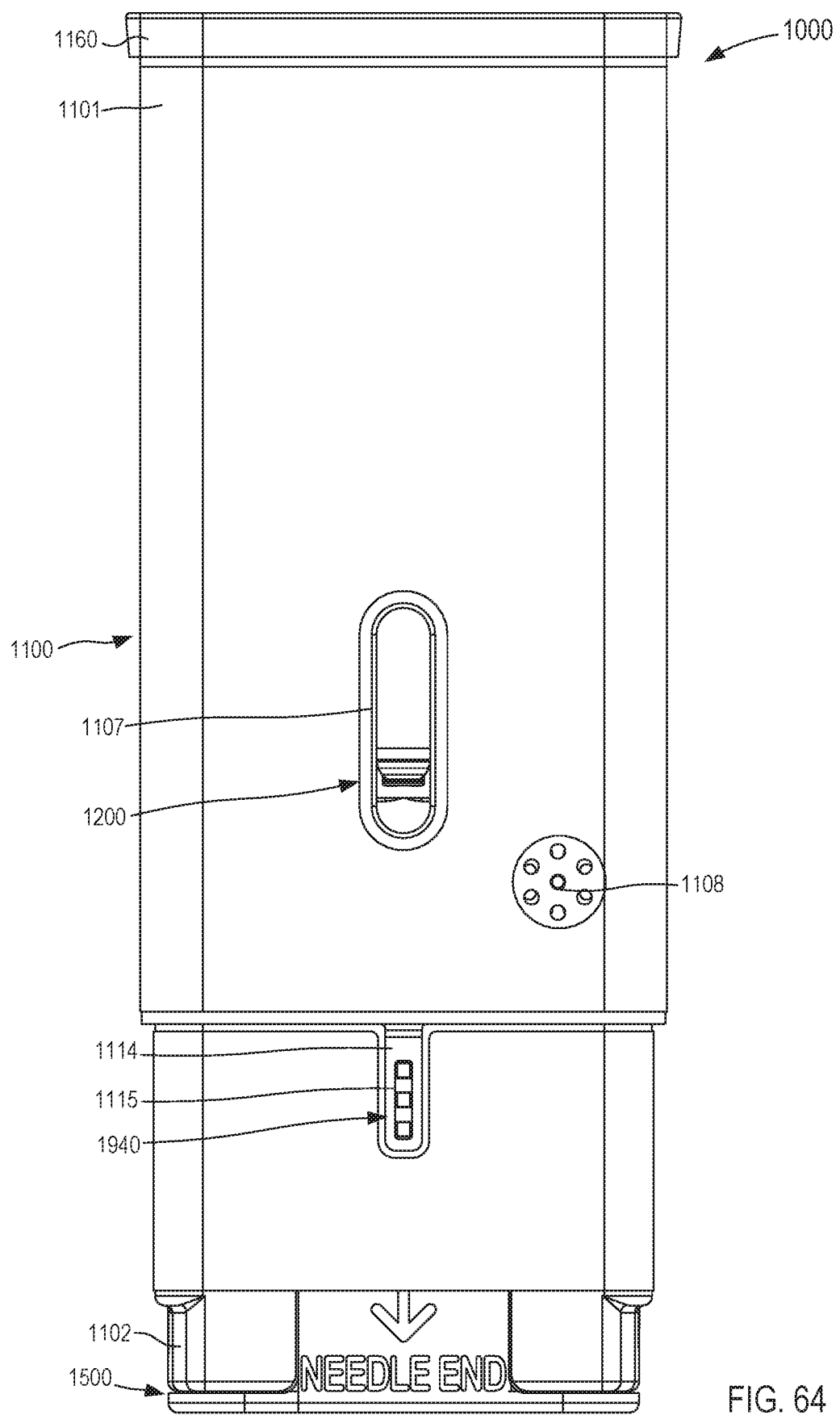
FIG. 64 is a front view of the medicament delivery device of FIG. 11 in an eighth configuration (i.e., after retraction of the needle).
Figure 65:
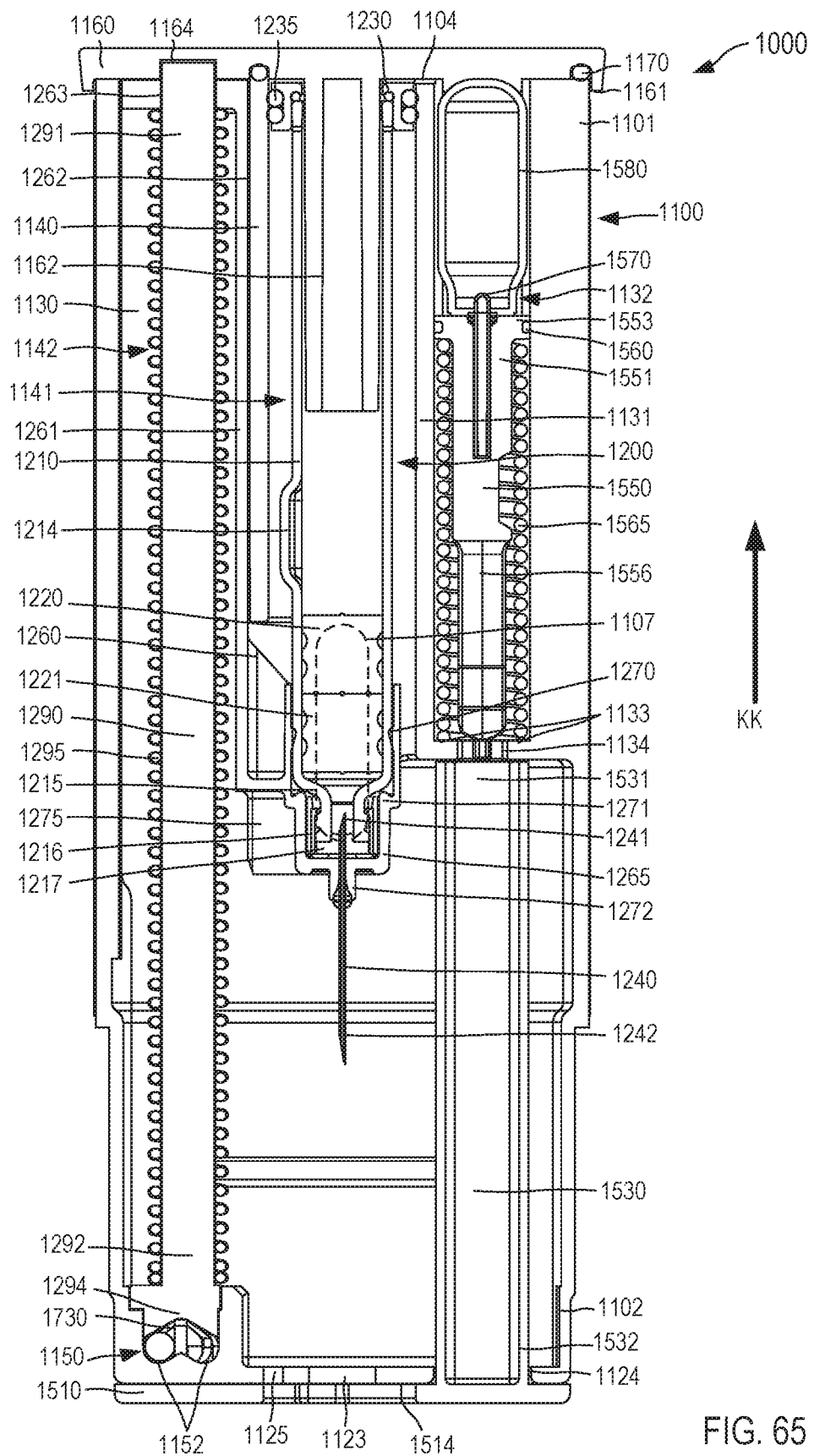
FIG. 65 is a cross-sectional view of the medicament delivery device of FIG. 11 in the eighth configuration, taken along the line $X_1$-$X_1$ in FIG. 15.

FIGS. 11-65 show various views of a medical injector 1000 according to an embodiment in various different configurations (or stages of operation). FIG. 11 is a perspective view of the medical injector 1000 (also referred to herein as "medicament delivery device" or "device") in a first configuration (i.e., prior to use). FIGS. 12 and 13 are a front view and a rear view, respectively, of the medical injector 1000 in a second configuration (i.e., with the case 1180 removed). FIGS. 14 and 15 are a front view and a top view, respectively, of the medical injector 1000 in a third configuration (i.e., with the safety lock removed to initiate mixing). The medical injector 1000 includes a housing 1100 (see e.g., FIGS. 16-26), a system actuator assembly 1500 (see e.g., FIGS. 27-33), a medicament container assembly 1200 including a medicament container 1210 (see e.g., FIGS. 34-36), a carrier 1260 (FIGS. 37-39), an electronic circuit system 1900 (see e.g., FIGS. 40-46), a cover 1180 (see e.g., FIGS. 47-10), and a safety lock (or mixing actuator, see e.g., FIGS. 51-54, also referred to as a mixing actuator). A discussion of the components of the medical injector 1000 will be followed by a discussion of the operation of the medical injector 1000 corresponding to FIGS. 55-65.

As shown in FIGS. 16-26, the housing 1100 has a proximal end portion 1101 and a distal end portion 1102, and an outer surface 1105 and an inner surface 1130. The housing 1100 defines a pair of status indicator apertures 1107 disposed on a front side 1106 and a rear side 1110 of the housing 1100 (e.g., opposite sides of the housing 1100), which are configured to allow a patient to monitor the status and/or contents of the medicament container 1200 contained within the housing 1100. For example, by visually inspecting the status indicator apertures 1107, a patient can determine whether the medicament container 1200 contains a medicament and/or whether the medicament has been dispensed. As shown in FIG. 16, the housing 1100 defines a set of audible output device openings 1108. As described in further detail herein, the housing 1100 is configured to house the electronic circuit system 1900 such that an audible output device 1930 (see e.g., FIGS. 40, 41 and 50) is substantially aligned with the audible output device openings 1108. Thus, during use, the audible output device openings 1108 can allow sound waves produced by the audible output device 1930 to pass therethrough.

As shown in FIGS. 16 and 17, the distal end portion 1102 of the housing 1100 includes a set of alignment protrusions 1114 and defines a set of recess 1111 and a LED opening 1115. The alignment protrusions 1114 extend from the outer surface 1105 on the front side 1106 and the rear side 1110 of the housing 1100. In some embodiments, the alignment protrusion 1114 on the first side 1106 of the housing 1100 is substantially opposite the alignment protrusion 1114 on the second side 1110 of the housing 1100. In other embodiments, the alignment protrusions 1114 need not be aligned and/or opposite each other. The alignment protrusions 1114 are configured to be matingly inserted into a corresponding alignment notch 1703 of the safety lock 1700 (also referred to as the mixing actuator, see e.g., FIGS. 12 and 13). As shown in FIG. 16, the alignment protrusion 1114 disposed on the front side 1106 of the housing 1100 defines the LED opening 1115. As described in further detail herein, the housing 1100 is configured to housing the electronic circuit system 1900 such that a set of LEDs 1940 are aligned with and at least partially extend through the LED opening 1115 (see e.g., FIG. 12). Thus, a user can verify a status and/or receive an instruction associated with the medical injector 1000 by visually inspecting the LEDs 1940 via the LED opening 1115.

As shown in FIGS. 16 and 17, the outer surface 1105 of the housing 1100 defines the recesses 1111 on the front side 1106 and the rear side 1130 of the housing 1100. The recesses 1111 are configured to receive a portion of a base 1510 included in the system actuator assembly 1500. Similarly, the recesses 1111 each define a set of actuator retention notches 1112 and a carrier lock aperture 1113. More specifically, the actuator retention notches 1112 disposed on the front side 1106 of the housing 1100 include, for example, a pair of distal actuator retention notches 1112 and a proximal retention notch 1112. The pair of distal actuator retention notches 1112 are configured to receive a corresponding pair of retention members 1519 of the base 1510 (see e.g., FIG. 29) when the system actuator assembly 1500 is in a first position relative to the housing 1100. The proximal actuator retention recess 1112 is configured to receive the corresponding retention member 1519 of the base 1510 when the system actuator assembly 1500 is in a second position relative to the housing 1100. As described in further detail herein, the housing 1100 can house the medicament container assembly 1200 such that a lock portion 1275 of the carrier 1260 (see e.g., FIG. 37) is at least partially disposed in the carrier lock aperture 1113 when the carrier 1260 is in a first position relative to the housing 1100 (e.g., prior to insertion and injection, for example, when the device 1000 is in the first or second configuration).

In some embodiments, the actuator retention notches 1112 have a tapered proximal sidewall and a non-tapered distal sidewall. This allows the actuator retention notches 1112 to receive the retention members 1519 of the base 1510 to allow the base 1510 to move proximally relative to the housing 1100 (e.g., to actuate the injector 1000), but to substantially prohibit the base 1510 from moving distally relative to the housing 1100. Said another way, the distal actuator retention notches 1112 are configured to prevent the base 1510 from moving distally when the system actuator 1500 is in its first position and the proximal actuator retention notches 1112 are configured to prevent the base 1510 from moving distally when the system actuator 1500 is in its second (or actuated) position. Thus, the actuator retention notches 1112 and the retention members 1519 of the actuator cooperatively limit movement of the system actuator 1500 to prevent undesirable movement of the system actuator 1500 after the medical injector 1000 is actuated. Specifically, the retention member 1519 prevent the base 1510 from being removed from the housing 1100 (e.g., pulled distally from the housing) when the safety lock 1700 is removed. The arrangement of the second side 1130 of the housing 1100 is substantially similar to the first side 1106 of the housing 1100 and thus, is not described in further detail herein.

Figure 18:
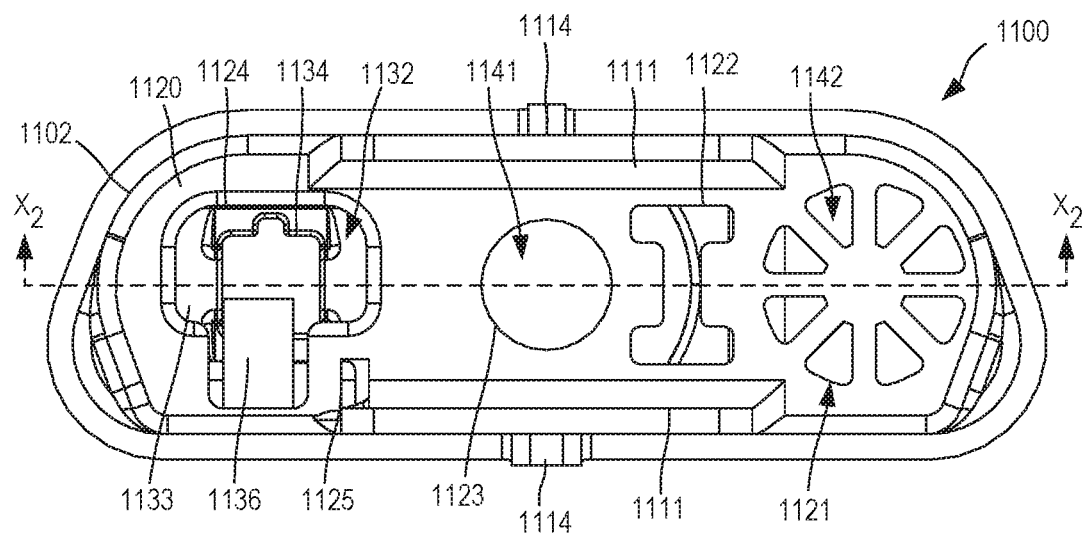
FIGS. 18 and 19 a bottom view and a top view, respectively, of the housing of FIG. 16.
Figure 19:
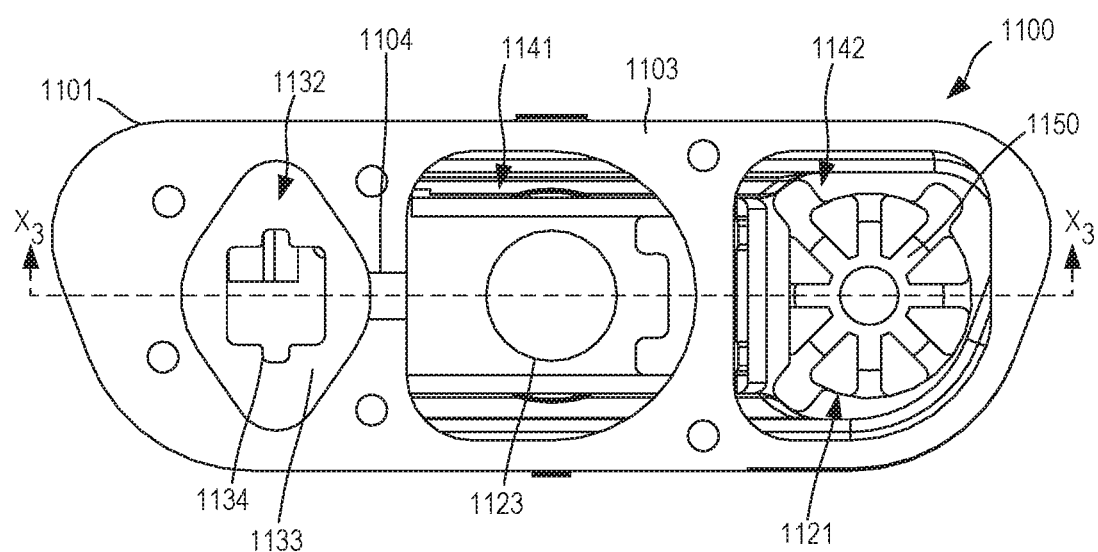

As shown in FIGS. 18 and 19, the distal end portion 1102 of the housing 1100 defines a set of lock mechanism openings 1121, a lock rod opening 1122, a needle opening 1123, a system activation opening 1124, and an electronic activation opening 1125. The set of lock mechanism openings 1121 receives, at least partially, a lock portion 1705 included in the safety lock (or mixing actuator) 1700 (see e.g., FIGS. 25, 26, and 51-54) when the safety lock 1700 is coupled to the housing 1100. Similarly, the lock rod opening 1122 receives a portion of a lock rod 1715 included in the safety lock 1700 (see e.g., FIGS. 25, 26, and 51-54) when the safety lock 1700 is coupled to the housing 1100. The needle opening 1105 is the opening through which the needle 1240 is disposed (see e.g., FIGS. 25 and 26) when the medical injector 1000 is actuated. The system activation opening 1124 receives a release rod 1530 extending from a proximal surface 1511 of the base 1510 of the system actuator assembly 1500 (see e.g., FIGS. 25 and 27) and allows the system actuator 1500 to be moved in a proximal direction relative to the housing 1100. In addition, the system activation opening 1124 receives a battery isolation protrusion 1185 of the cover 1180 (see e.g., FIGS. 48 and 50) when the cover 1180 is disposed about at least a portion of the housing 1100. The electronic activation opening 1125 receives an electronic actuator protrusion 1520 of the base 1510 (see e.g., FIGS. 28 and 29) and allows the system actuator 1500 to engage a portion of the electronic circuit system 1900, as described in further detail herein.

Figure 25:
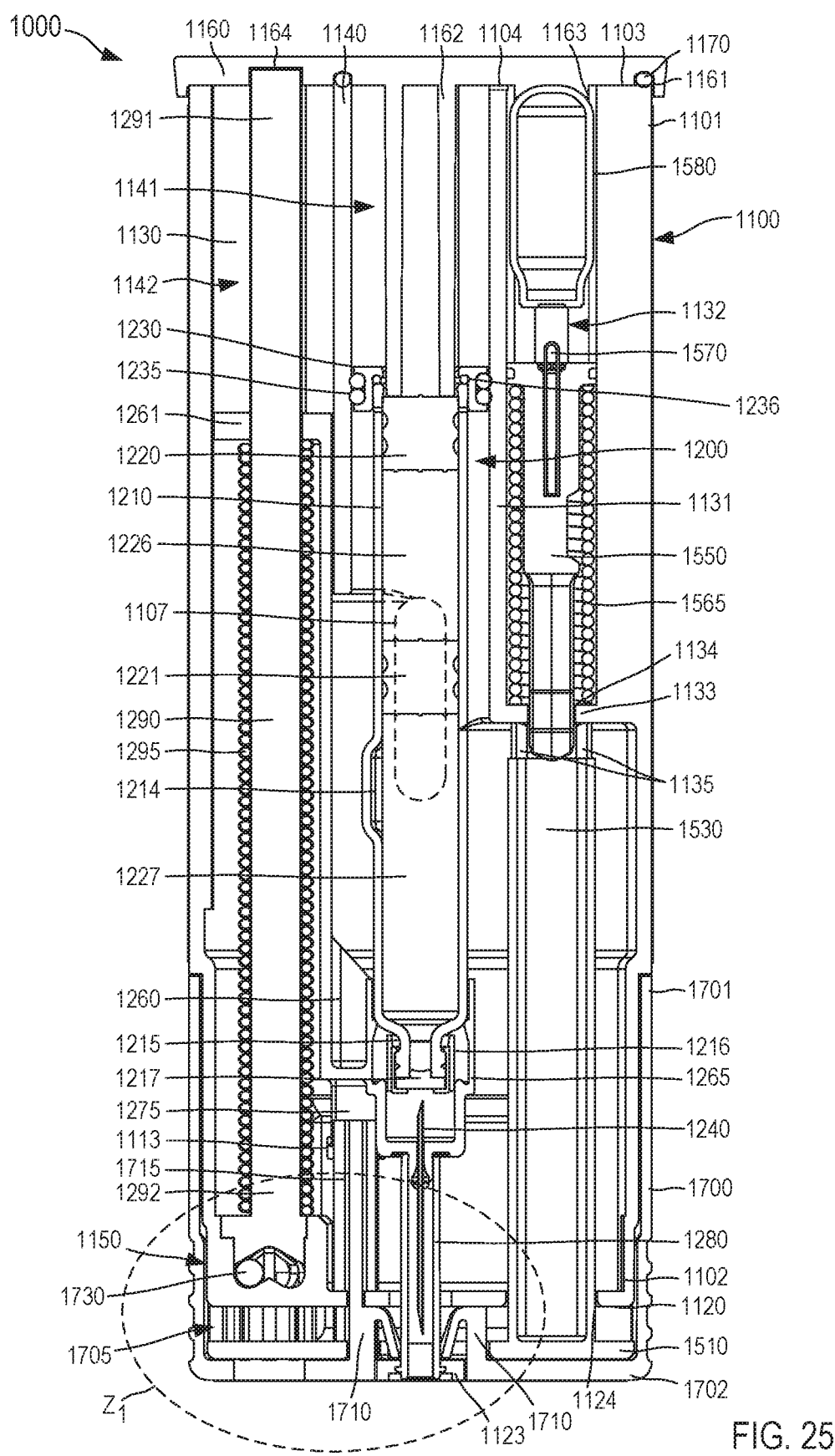
FIG. 25 is a cross-sectional view of the medicament delivery device of FIG. 11 in the second configuration (i.e., with the case removed and the safety lock in the "locked" position) taken along the line $X_1$-$X_1$ in FIG. 15.
Figure 26:
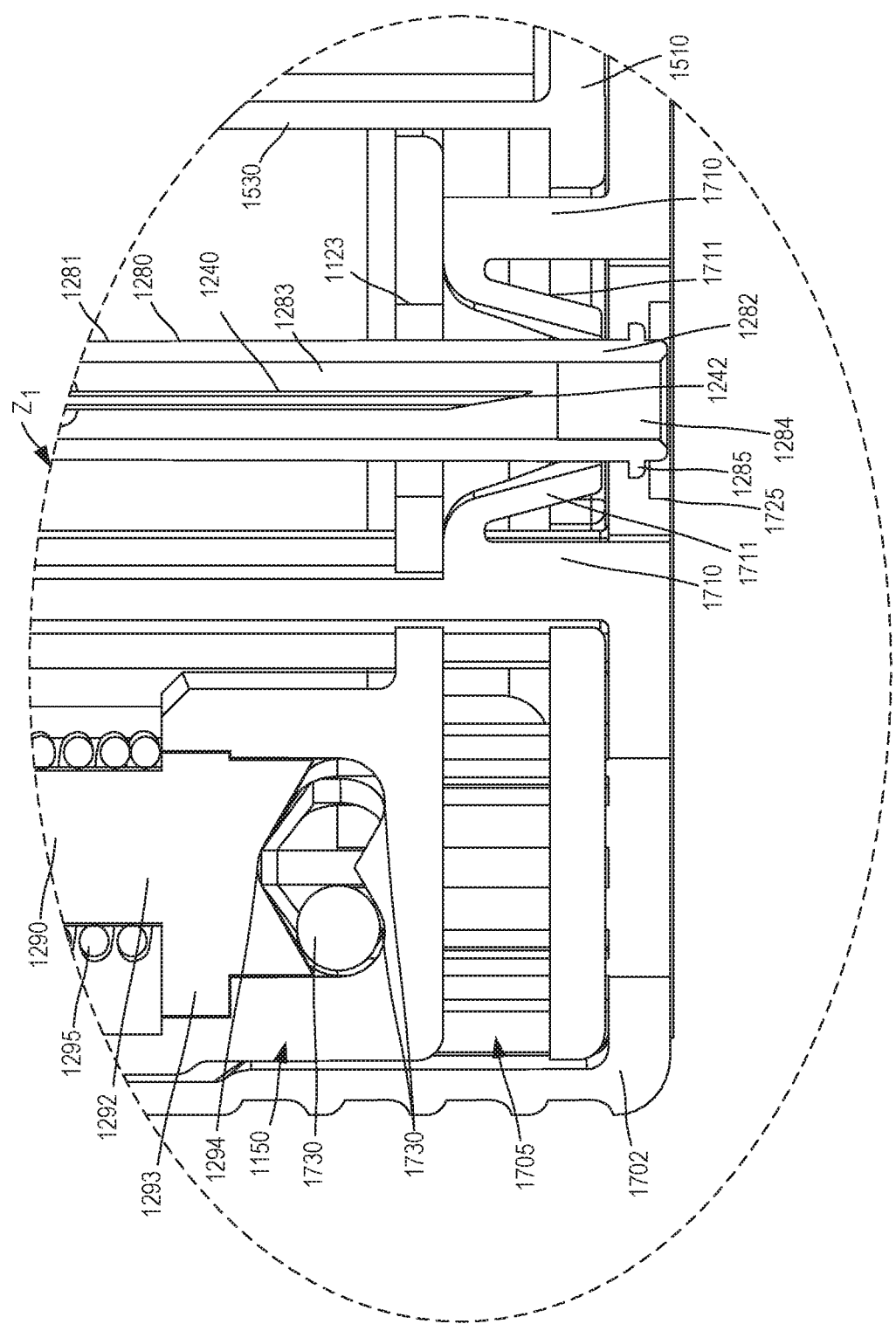
FIG. 26 is an enlarged view of a portion of the medicament delivery device of FIG. 1 identified by the region $Z_1$ in FIG. 25.

As shown in FIGS. 18-22, the inner surface of the housing 1100 defines a gas cavity 1132, a medicament cavity 1141, and a mixing actuator cavity 1142. The gas cavity 1132 is configured to receive a set of retention members 1163 included in a proximal cap 1160, a gas container 1580, and a portion of the system actuator assembly 1500 (e.g., a release member 1550 and a spring 1565, as shown in FIG. 25), as described in further detail herein. The gas cavity 1132 is at least partially separated from the medicament cavity 1141 and the mixing actuator cavity 1142. Specifically, the inner surface 1130 includes and/or forms a sidewall 1131 and a distal wall 1133, which collectively define at least a portion of the gas cavity 1132. As shown in FIGS. 19-22, the gas cavity 1132 is in fluid communication with the medicament cavity 1141 via a gas passageway 1104 defined, for example, by a proximal surface 1103 of the housing 1100, as described in further detail herein. The distal wall 1133 defines an opening 1134 that is configured to receive a portion of the release member 1550 (see e.g., FIG. 25). More particularly, a distal end portion 1552 of the release member 1550 can be maintained in contact with the distal wall 1133 prior to using the medical injector 1000. Thus, prior to actuating the medical injector 1000 the release member 1550 is substantially prevented from moving in a proximal direction relative to the housing 1100, as described in further detail herein. As described in further detail herein, inner surface 1130 of the housing 1100 includes and/or forms a set of actuator protrusions 1135 that are configured to limit a transverse or lateral movement of the release rod 1530 while allowing the release rod 1530 to move substantially freely in an axial direction (e.g., proximal and/or distal direction).

Figure 22:
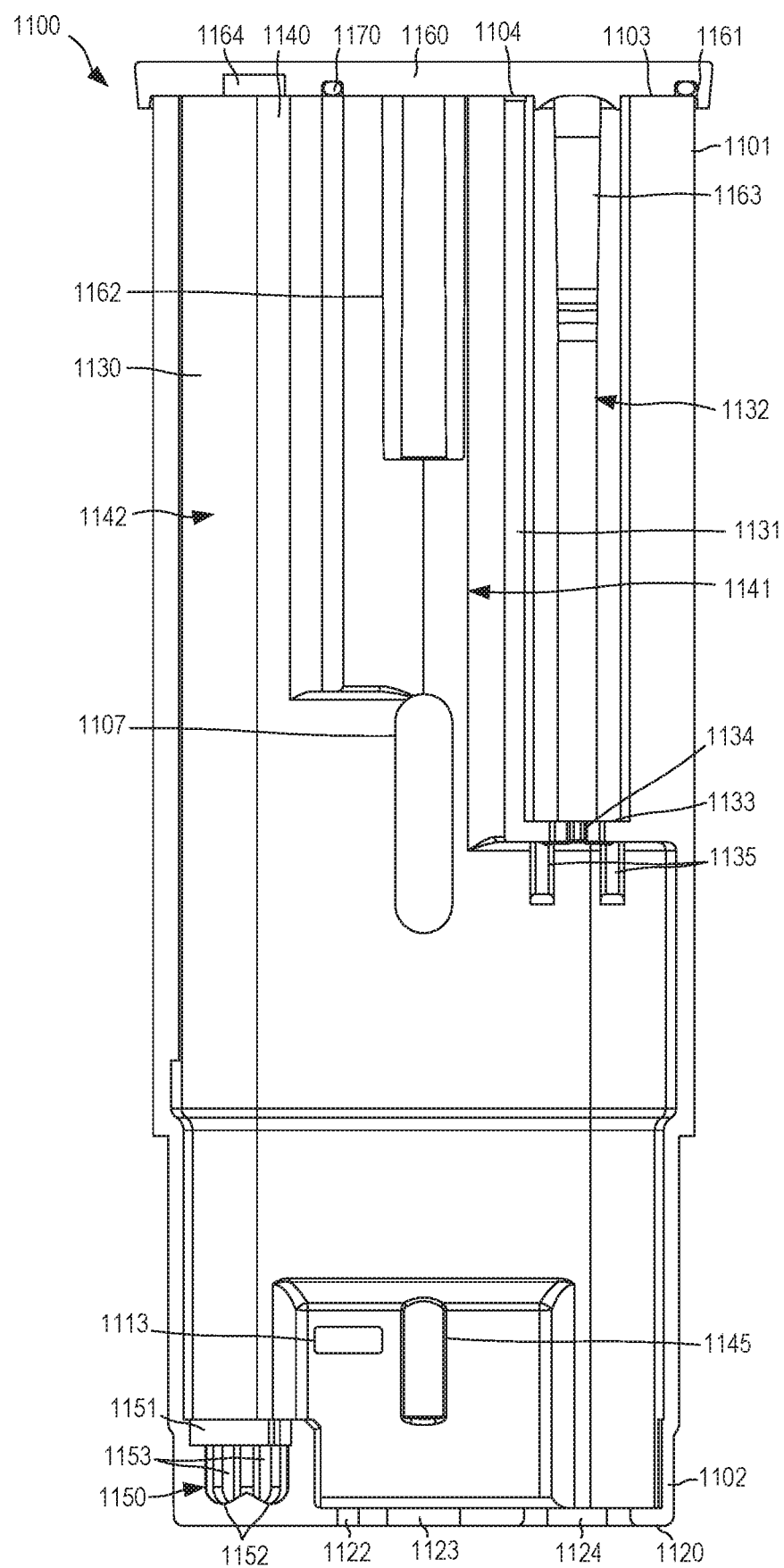
FIG. 22 is a cross-sectional view of a portion of the medicament delivery device of FIG. 11 taken along the line $X_1$-$X_1$ in FIG. 15.
Figure 23:
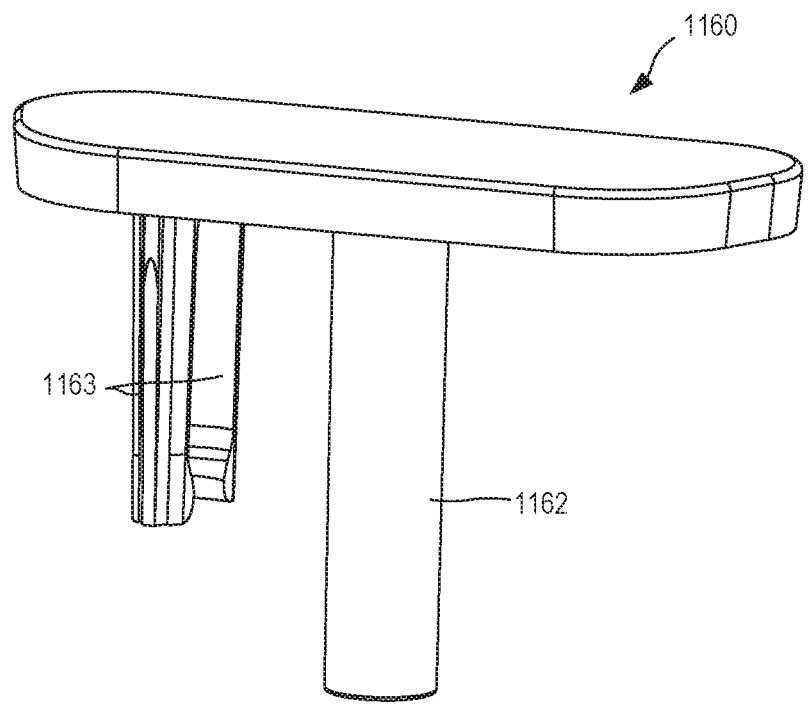
FIGS. 23 and 24 are a front perspective view and a bottom perspective view, respectively, of a proximal cap included in the medicament delivery device of FIG. 11.
Figure 24:
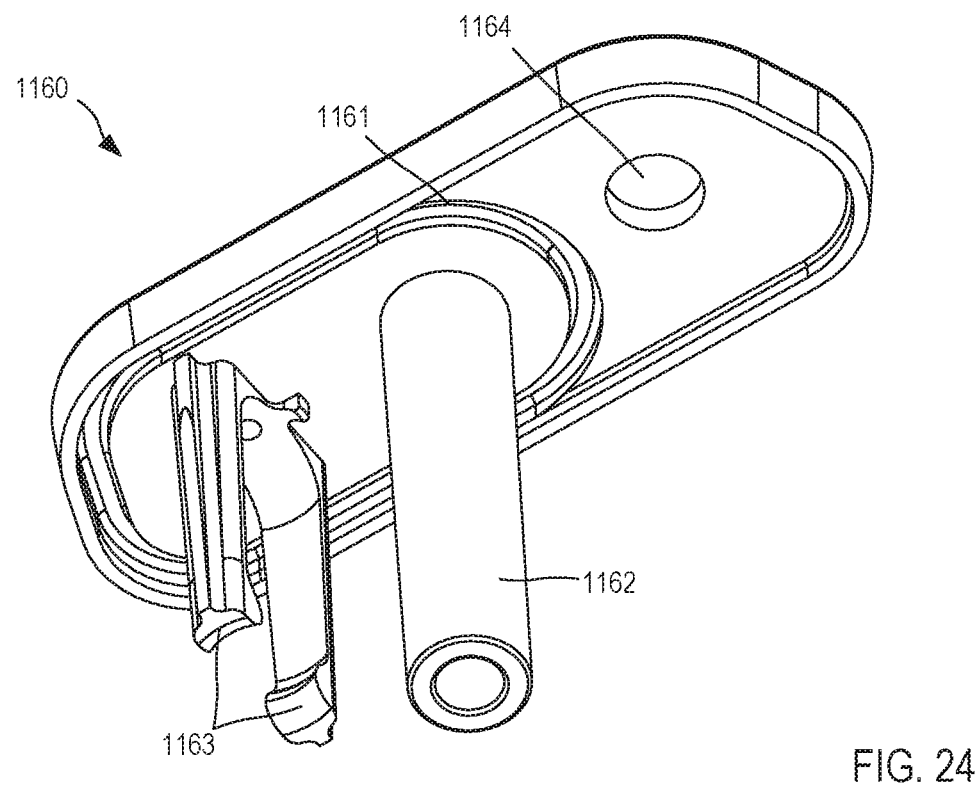

The medicament cavity 1141 is configured to receive the medicament container assembly 1200 and a mixing protrusion 1162 of the proximal cap 1160 (see e.g., FIGS. 23-25). As shown in FIGS. 20-22 at least a portion of the medicament cavity 1141 is separated from the gas cavity 1132 and the mixing actuator cavity 1142. More specifically, the inner surface 1130 of the housing 1100 includes and/or forms the sidewall 1131, which separates the medicament cavity 1141 from the gas cavity 1132, and a sidewall 1140, which separates at least a portion of the medicament cavity 1141 from the mixing actuator cavity 1142. As described in further detail herein, the medicament container assembly 1200 is movable within the medicament cavity 1141 in the proximal direction and in the distal direction. Moreover, the medicament container 1210 included in the medicament container assembly 1200 includes a proximal flange 1230 with an outer seal member 1235 configured to form a substantially fluid tight seal with the inner surface 1130 of the housing 1100 defining the medicament cavity 1141 (see e.g., FIG. 25). The medicament container assembly 1200 also includes an inner seal member 1236 disposed between an inner surface of the flange 1230 and the medicament container 1210. The inner seal member 1236 form a substantially fluid tight seal with the inner surface of the flange 1230 defining the medicament cavity 1141 (see e.g., FIG. 25).

The mixing actuator cavity 1142 is configured to receive a mixing actuator rod 1290, a bias member 1295 (e.g., a spring or the like), and a portion of the carrier 1260. More particularly, the mixing actuator rod 1290 of the medicament container assembly 1290 is fixedly disposed in the mixing actuator cavity 1142 and extends from a lock mechanism portion 1150 disposed at or near the distal end portion 1102 of the housing 1100 to a mixing rod recess 1164 defined by the proximal cap 1160. A mixing portion 1261 of the carrier 1260 is disposed about the mixing actuator rod 1290 and is movable within the mixing actuator cavity 1142 along a length of the mixing actuator rod 1290 in response to a force produced by the bias member 1295, as described in further detail herein.

As shown in FIGS. 20-22, the inner surface 1130 of the housing 1100 includes and/or forms the lock portion 1150 and defines a pair of medicament container recesses 1145 disposed on opposite sides on the inner surface 1130. The medicament container recesses 1145 are configured to increase a distance between opposite sides of the inner surface 1130 to allow a portion of the medicament container 1210 to move therebetween, as described in further detail herein. The lock portion 1150 defines a recess 1151, a basket 1152, and a set of openings 1153. The recess 1151 is configured to receive a corresponding portion of the mixing actuator rod 1290 (see e.g., FIGS. 25 and 26). In some embodiments, the portion of the mixing actuator rod 1290 (e.g., a distal end portion 1292) can be fixedly disposed in the recess 1151 and maintained therein via an adhesive, a fastener, a friction fit, a snap fit, an ultrasonic weld, and/or the like or combination thereof. More particularly, the distal end portion 1292 of the mixing actuator rod 1290 includes a flange 1293 configured to be disposed in the recess 1151 defined by the lock portion 1150. The set of openings 1153 are configured to receive a lock portion 1705 of the safety lock 1700. As described in further detail herein, the lock portion 1150 of the housing 1100 can receive a lock member (or lock ball) 1730 that can be selectively positioned in the basket 1152 such that the lock portion 1150 of the housing 1100, the mixing actuator rod 1290 of the medicament container assembly 1200, and the safety lock 1700 collectively maintain the safety lock 1700 in a fixed position relative to the housing 1100, which in turn, prevents the medical injector 1000 from being actuated (see e.g., FIGS. 25 and 26). In particular, as described in more detail below, the lock member 1730 is positioned to limit movement of the safety lock (or mixing actuator) 1700 relative to the housing 1100 when the medical injector 1000 is outside of a desired orientation range (e.g., when the medical injector 1000 is not within approximately 30 degrees of being vertical, with the needle tip pointed upwards).

As described above, the proximal end portion 1101 of the housing 1100 includes and/or is otherwise coupled to a proximal cap 1160 (see e.g., FIGS. 22-24). The proximal cap 1160 includes the retention members 1163 and the mixing protrusion 1162, and defines a seal recess 1161 and the mixing rod recess 1164. As shown in FIG. 22, the proximal cap 1160 is coupled to the proximal surface 1103 of the housing 1100. In some embodiments, the proximal cap 1103 is fixedly coupled to the proximal surface 1103 via, for example, ultrasonic welding, adhesive, fasteners, and/or the like or a combination thereof. Moreover, a seal member 1170 is disposed in the seal recess 1161 and is configured to form a substantially fluid tight seal between the proximal cap 1160 and the proximal surface 1103 of the housing 1100.

The retention members 1163 of the proximal cap 1160 are configured to receive and/or retain the gas container 1580 that contains a pressurized gas, as shown in FIG. 25. When the medical injector 1000 is actuated, pressurized gas from the gas container 1580 is conveyed from the gas cavity 1132 to the medicament cavity 1141 via the gas passageway 1104 (described above). Said another way, the gas passageway 1104 places the gas cavity 1132 in fluid communication with the medicament cavity 1141. The mixing protrusion 1162 extends from a surface of the proximal cap 1160 and is configured to engage a portion of the medicament container assembly 1200 (e.g., an elastomeric member 1220 disposed in the medicament container 1210), as described in further detail herein. The mixing rod recess 1164 receives a proximal end portion 1291 of the mixing actuator rod 1290. In some embodiments, the proximal end portion 1291 of the mixing actuator rod 1290 can be fixedly disposed in the mixing rod recess 1164 via a friction fit, a fastener, an adhesive, ultrasonic welding, and/or the like or a combination thereof. Thus, in some embodiments, the proximal end portion 1291 of the mixing actuator rod 1290 can be fixedly coupled to the proximal cap 1160 and the distal end portion 1292 can be fixedly coupled to the lock portion 1150 of the housing 1100 such that the mixing actuator rod 1290 substantially traverses the mixing actuator cavity 1142.

Figure 29:
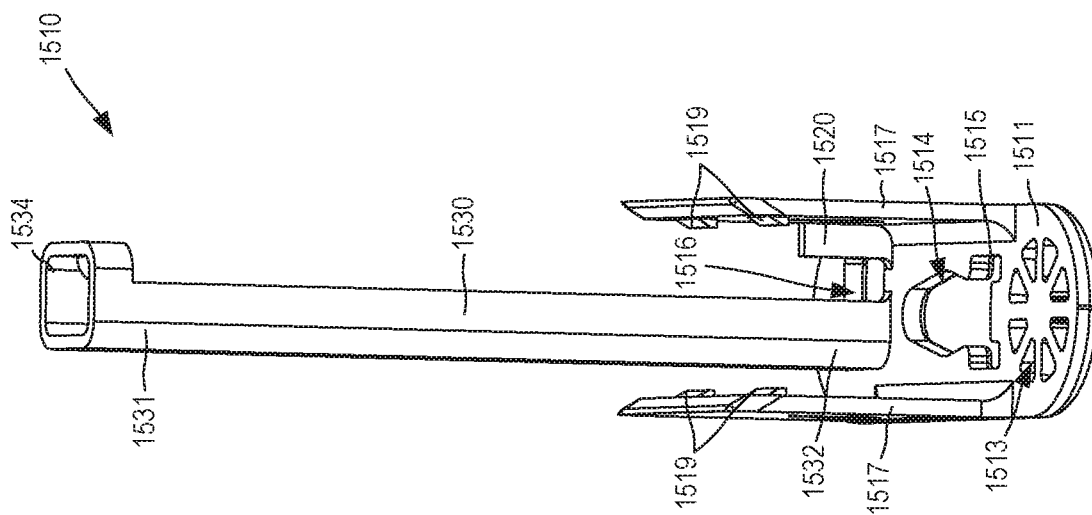
FIGS. 28 and 29 are perspective views of a system actuator included in the medicament delivery device of FIG. 11.
Figure 30:
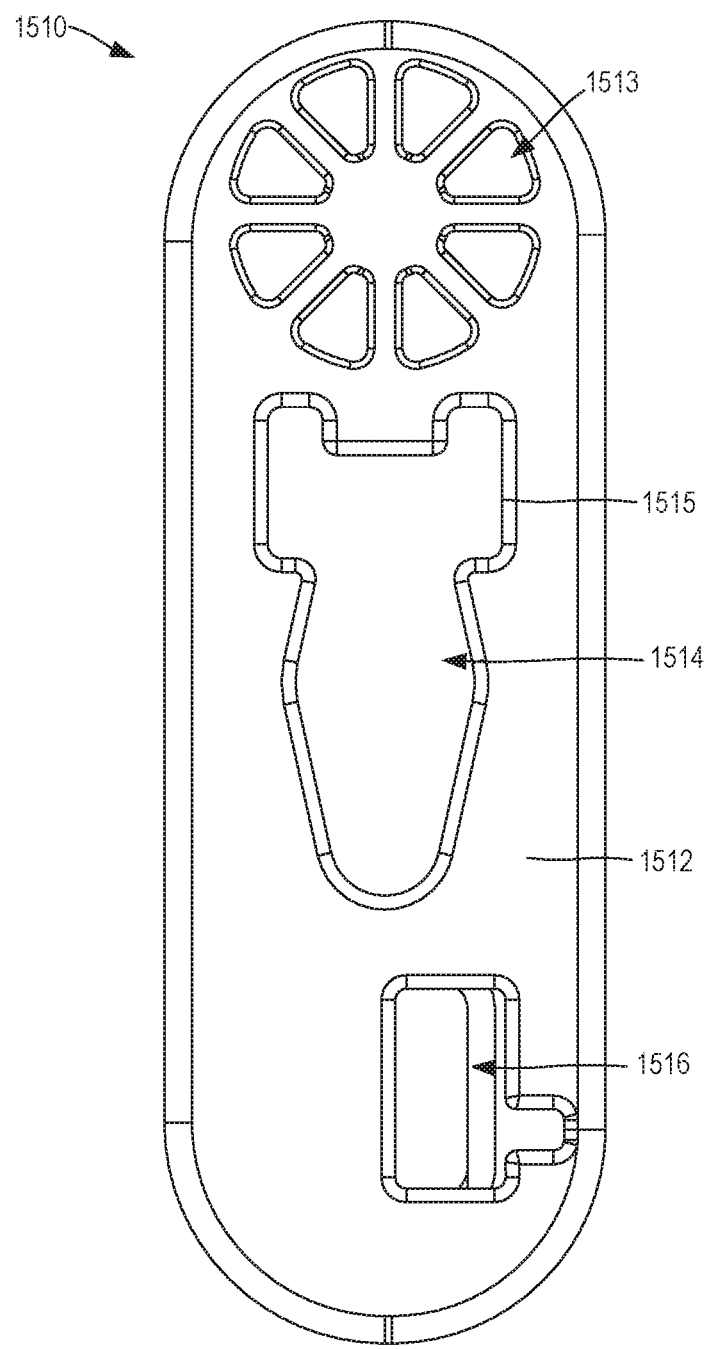
FIG. 30 is a bottom view of the system actuator of FIG. 28.

FIGS. 27-39 show the medicament container assembly 1200, the system actuator assembly 1500, and the proximal cap 1160 of the medical injector 1000. As shown in FIGS. 27-33, the system actuator assembly 1500 includes the base 1510, a release member 1550, and a spring 1565. As shown in FIGS. 28-30, the base 1510 of the system actuator assembly 1500 includes a proximal surface 1511, a distal surface 1512. The base 1510 defines a set of lock mechanism openings 1513, a needle opening 1514 with a safety lock rod portion 1515, and a battery isolation protrusion opening 1516. The set of lock mechanism openings 1513 receive, at least partially, the lock portion 1705 included in the safety lock 1700 (see e.g., FIGS. 25, 26, and 51-54) when the safety lock 1700 is coupled to the housing 1100. Similarly, the safety lock rod portion 1515 of the needle opening 1514 receives a portion of the lock rod 1715 of the safety lock 1700 (see e.g., FIGS. 25, 26, and 51-54) when the safety lock 1700 is coupled to the housing 1100. The needle opening 1514 also receives and/or allows the needle 1240, an engagement portion 1710 of the safety lock 1700, and a needle sheath 1280 to be disposed and/or pass therethrough, as described in further detail herein. The battery isolation protrusion opening 1516 receives the battery isolation protrusion 1185 of the cover 1180 and an electronic activation protrusion 1720 of the safety lock 1700, as described in further detail herein.

The proximal surface 1511 of the base 1510 includes and/or is coupled to the release rod 1530, a set of tabs 1517, and an electronic actuator protrusion 1520. More specifically, in this embodiment, the base 1510 includes two tabs 1517 monolithically formed with the base 1510, each of which is disposed on opposite sides of the base 1510. As shown in FIG. 29, each tab 1517 includes a set of the retention members 1519. The retention members 1519 are configured to selective engage the actuator retention notches 1112 of the housing 1100, as described in detail above. The electronic actuator protrusion 1520 extends from the proximal surface 1511 of the base 1510 and is movably received in the electronic activation opening 1125 (see FIG. 16) of the housing 1100. The electronic actuator protrusion 1520 is configured to selectively engage a portion of the electronic circuit system 1900 to actuate at least a portion thereof, as described in further detail herein.

The release rod 1530 extends from the proximal surface 1511 of the base 1510 to selectively engage a portion of the release member 1550 when the base 1510 is moved relative to the housing 1100, as described in further detail herein. Although the base 1510 and the release rod 1530 are shown as being monolithically constructed to form a portion of the system actuator assembly 1500, in other embodiments, the system actuator assembly 1500 can include a base that is constructed separately from (and later joined to) a release member. A portion of the release rod 1530 is movably disposed within the system activation opening 1124 defined by the housing 1100 (see e.g., FIGS. 25 and 32). Said another way, the release rod 1530 extends from the base 1510 and through the system activation opening 1124 defined by the housing 1100 to allow the release rod 1530 to move within the housing 1100 from a first position to a second position, as described in further detail herein.

The release rod 1530 includes a proximal end portion 1531 and a distal end portion 1532 and defines a channel 1533 between an engagement surface 1534 and the distal end portion 1532 (see e.g., FIGS. 25, and 27-29). The channel 1533 receives a portion of the electronic circuit system 1900, thereby allowing a sufficient distance between the inner surface 1130 of the housing 1100 and the release rod 1530 to accommodate a portion of the electronic circuit system 1900. The engagement surface 1534 is disposed at the proximal end portion 1531 of the release rod 1530 and is configured to engage a distal end portion 1552 of the release member 1550, as described below. Although the engagement surface 1534 is shown as forming a substantially closed wall the circumscribes the proximal end portion 1531 of the release rod 1530, in other embodiments, the release rod 1530 can include an engagement surface 1534 having any suitable configuration.

Figure 27:
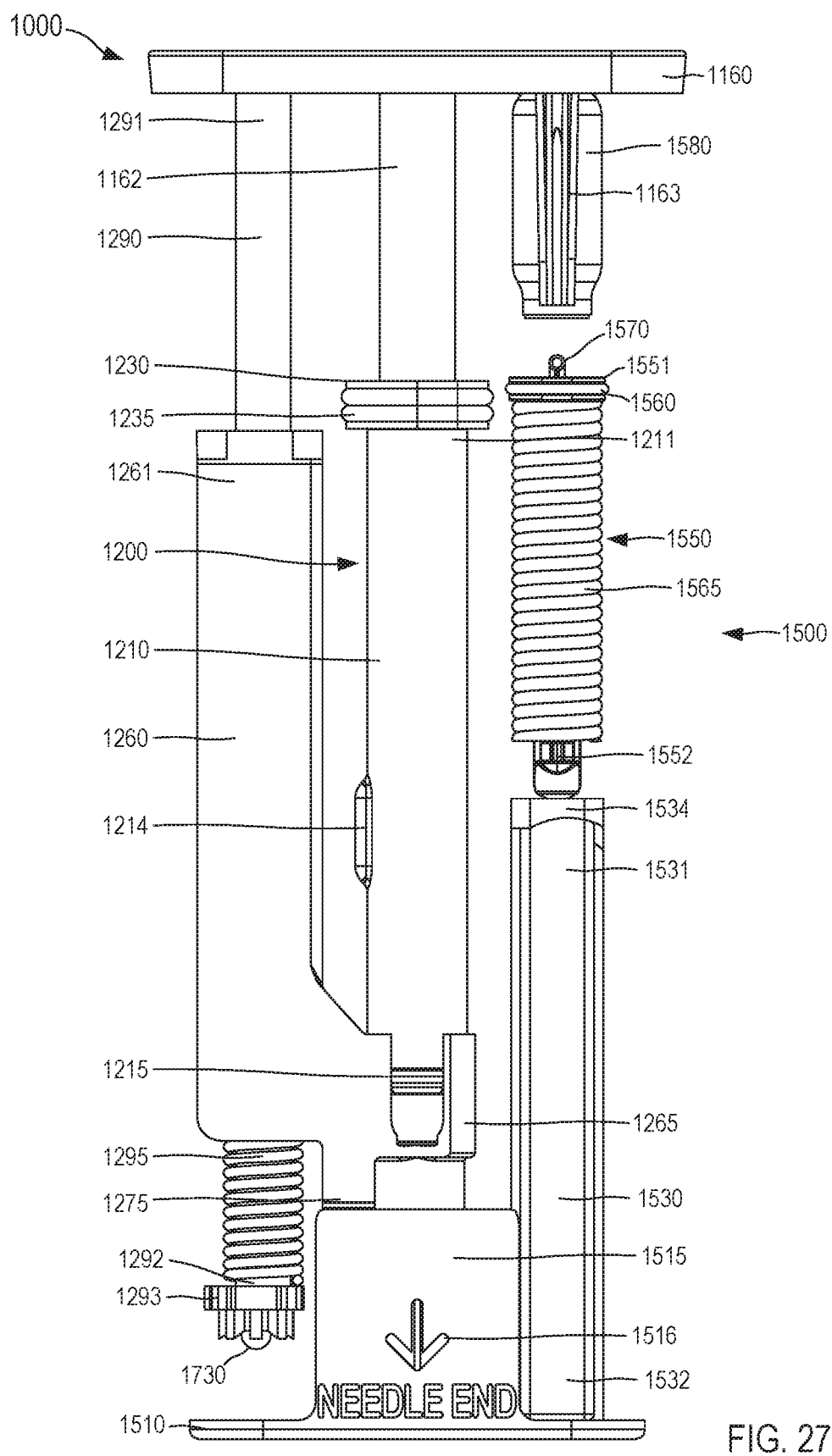
FIG. 27 is a front view of a portion of the medicament delivery device of FIG. 11 in the second configuration.
Figure 28:
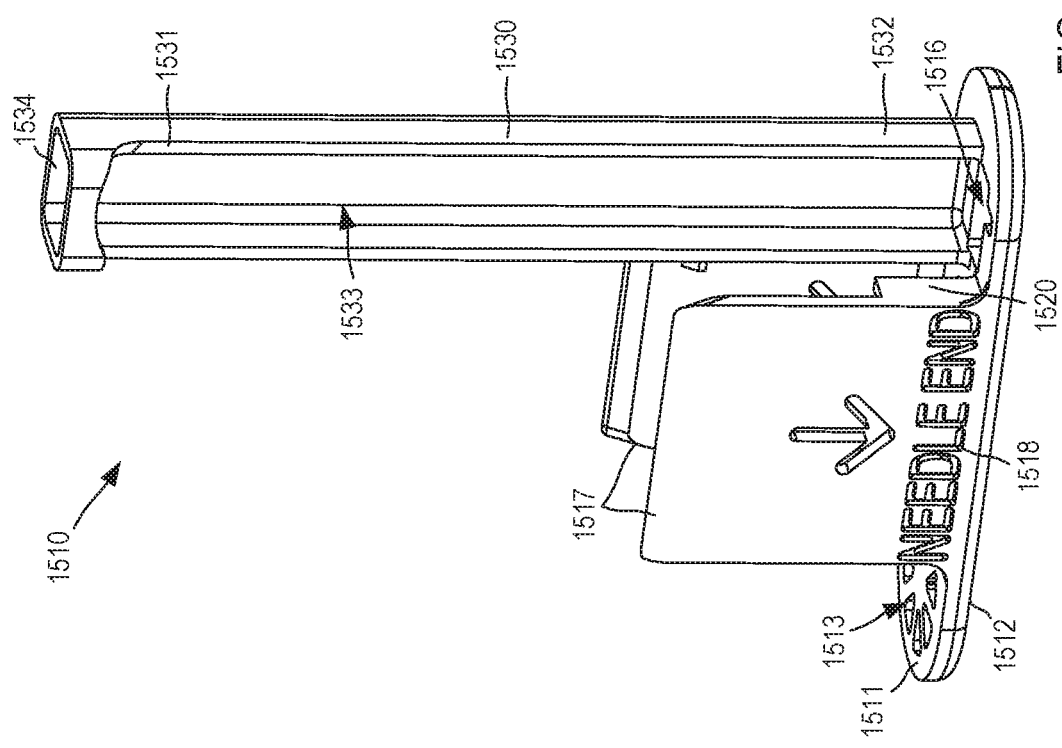
Figures 31, 32:
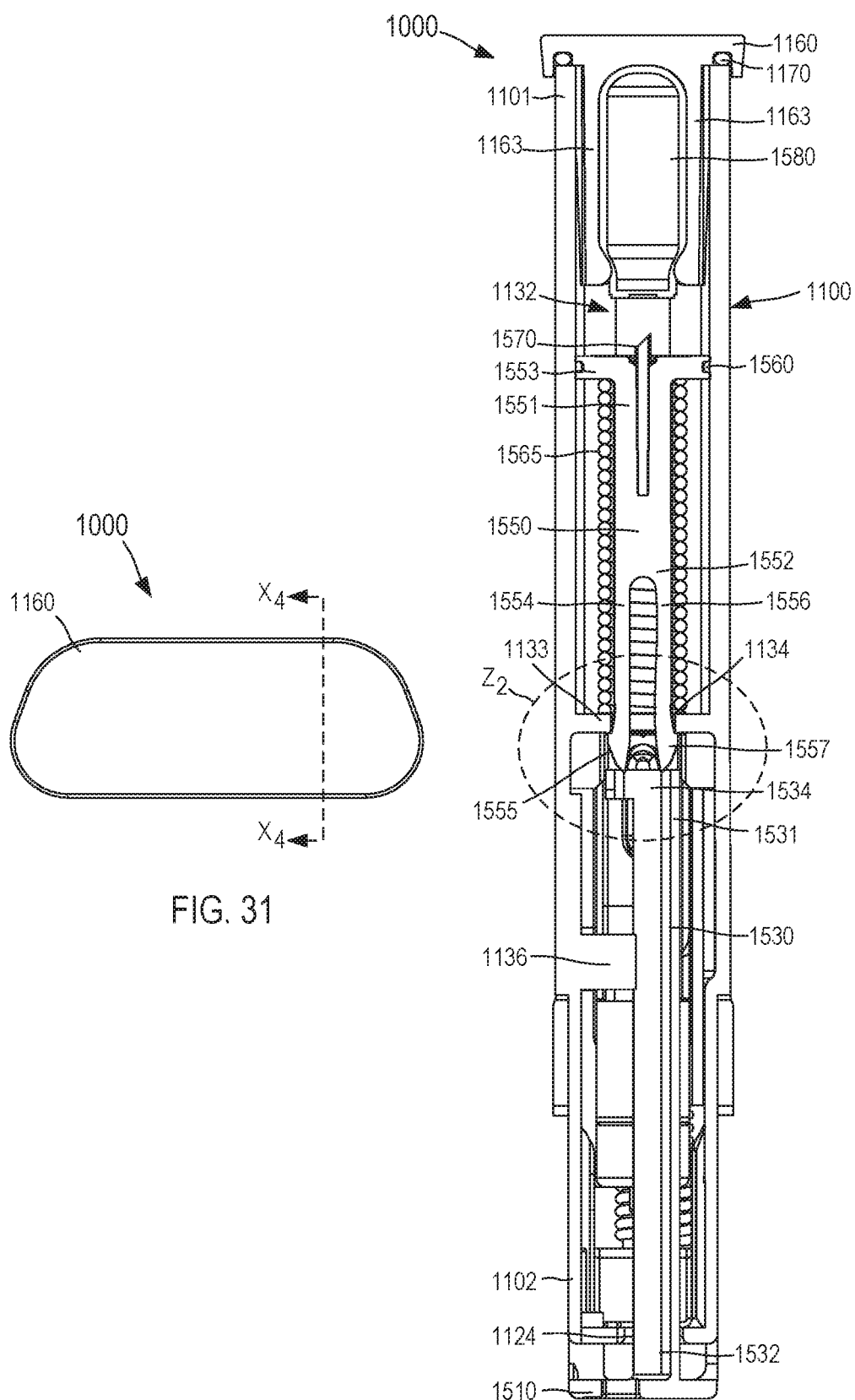
FIG. 31 is a top view of the medicament delivery device of FIG. 11.
FIG. 32 is a cross-sectional view of the medicament delivery device of FIG. 11 in the second configuration (i.e., with the case removed and the safety lock in the "locked" position) taken along the line $X_4$-$X_4$ in FIG. 31.

As shown in FIGS. 27 and 32, the release member 1550 of the system actuator assembly 1500 has a proximal end portion 1551 and a distal end portion 1552, and is movably disposed within the gas cavity 1132. The proximal end portion 1551 of the release member 1550 includes a flange 1553, a sealing member 1560, and a puncturer 1570. As shown in FIG. 32, the spring 1565 of the system actuator assembly 1500 is disposed between the flange 1553 and the distal wall 1133 of the housing 1100 that defines a portion of the gas cavity 1132. In this manner, the spring 1565 can be transitioned from a first configuration with a relatively high potential energy (e.g., a compressed configuration) to a second configuration with a relatively low potential energy (e.g., a non-compressed configuration) to exert a force on the flange 1553 of the release member 1550 sufficient to move the release member 1550 within the gas cavity 1132, as described in further detail herein.

In this embodiment, the sealing member 1560 substantially circumscribes the flange 1553 of the release member 1550. In other embodiments, the sealing member 1560 can be any suitable configuration such as, for example, an over-mold about the flange 1553 of the release member 1550. The sealing member 1560 is configured to be in contact with a portion of the inner surface 1130 of the housing 1100 defining the gas cavity 1132 such that a portion of the gas cavity 1132 proximal to the flange 1553 is substantially fluidically isolated from a portion of the gas cavity 1132 distal to the flange 1553. In this manner, when gas is released from the gas container 1580, the gas is contained in the portion of the gas cavity 1132 proximal to the flange 1553, as described in further detail herein.

The puncturer 1570 disposed at or near the proximal end portion 1551 of the release member 1550 is configured to contact and puncture, for example, a frangible seal of the gas container 1580 when the release member 1550 moves proximally within the gas cavity 1151, as described in further detail herein. As shown in FIG. 32, the length of the gas container retention member 1163 of the proximal cap 1160 and the length of the release member 1550 collectively determine a distance between the puncturer 1570 and the frangible seal (not shown) when the medical injector 1000 is in the storage configuration (or first configuration). This distance, which is the distance through which the puncturer 1570 travels when the medical injector 1000 is actuated, can be adjusted by changing the length of the gas container 1580, a length and/or arrangement of the gas container retention members 1163 of the proximal cap 1160, and/or the length of the release member 1550. In some embodiments, the actuation time and/or the force exerted by the puncturer 1570 on the frangible seal can be adjusted by changing the distance between the puncturer 1570 and the frangible seal.

Figure 33:
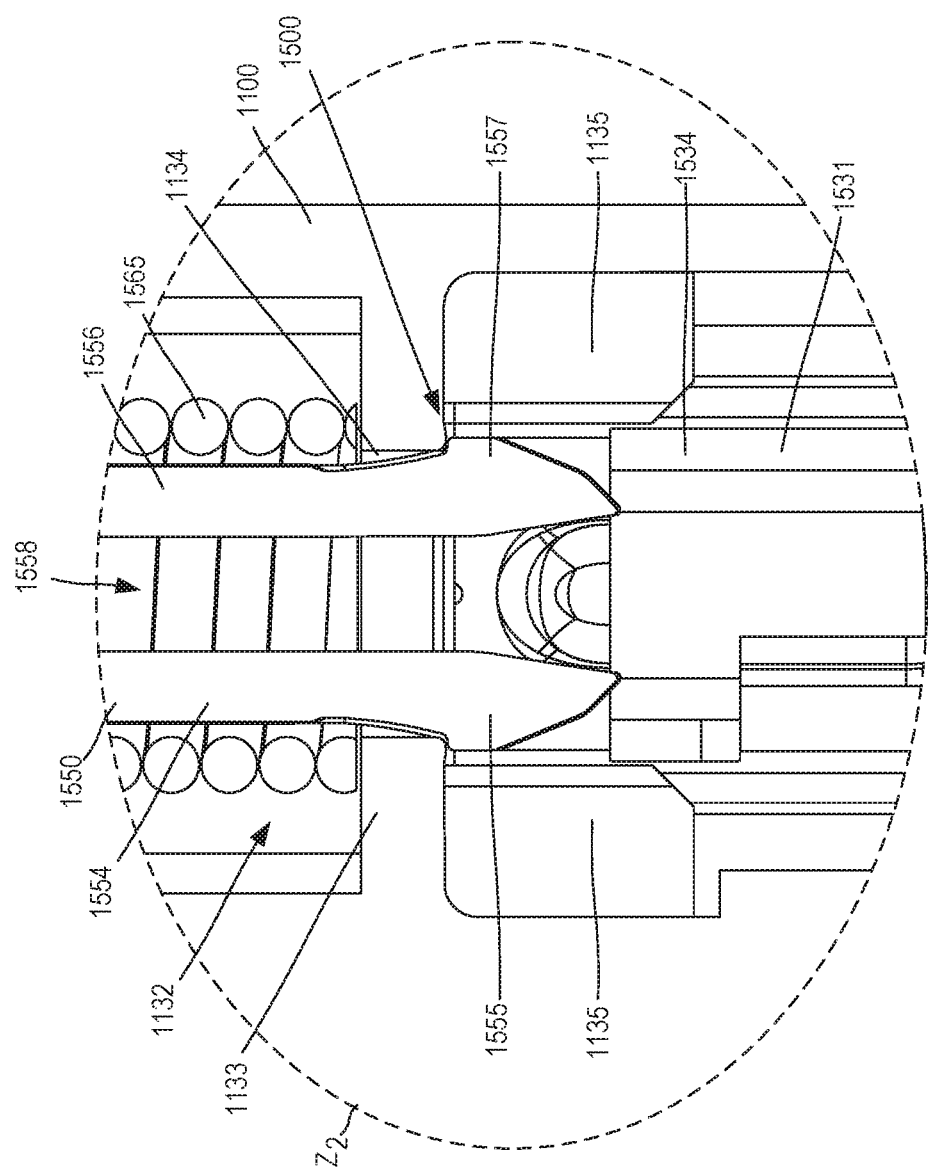
FIG. 33 is an enlarged view of a portion of the medicament delivery device of FIG. 1 identified by the region $Z_2$ in FIG. 32.

The distal end portion 1552 of the release member 1550 includes a first extension 1554 and a second extension 1556. The extensions 1554 and 1556 each have projections 1555 and 1557, respectively. As shown in FIGS. 32 and 33, the projection 1555 of the first extension 1554 and the projection 1557 of the second extension 1556 each include a surface configured to selectively engage the distal wall 1133 of the gas cavity 1132. More specifically, the release member 1550 is disposed within the gas cavity 1132 of the housing 1100 such that a portion of each extension 1554 and 1556 extends through the opening 1134 defined by the distal wall 1133 prior to actuation of the medical injection 1000. Thus, the surface of each projection 1555 and 1557 engages a distal surface of the distal wall 1133 and each are maintained in contact therewith until actuation of the medical injector 1000. In other words, the projections 1555 and 1557 engage the distal wall 1133 to limit proximal movement of the release member 1550 prior to actuation of the medical injector 1000. Furthermore, as shown in FIG. 33, an opening 1558 is defined between the extensions 1554 and 1556 (i.e., the first extension 1554 is spaced apart a distance from the second extension 1556). As described in further detail herein, the medical injector 1000 can be actuated to move the release rod 1530 in the proximal direction such that the engagement surface 1534 of the release rod 1530 contacts the protrusions 1555 and 1557, thereby reducing the distance defined between the extensions 1554 and 1556 (i.e., reduces the size of the opening 1558) to an extent that the projections 1555 and 1557 can pass through the opening 1134 defined by the distal wall 1133. As such, the spring 1565 can exert a force to move the release member 1550 in a proximal direction within the gas cavity 1132 to cause the puncture member 1570 to puncture the frangible seal of the gas container 1580, as described in further detail herein.

As shown in FIGS. 34-39, the medicament container assembly 1200 includes a medicament container 1210, the needle 1240, the carrier 1260, and the needle sheath 1280. The medicament container assembly 1200 functions cooperatively with the mixing actuator rod 1290 and the bias member 1295, as described herein. As shown in FIGS. 25 and 27, the mixing actuator rod 1290 includes the proximal end portion 1291 and the distal end portion 1292. The proximal end portion 1291 of the mixing actuator rod 1290 is disposed in and/or otherwise coupled to the mixing rod recess 1164 defined by the proximal cap 1160 of the housing 1100. The distal end portion 1292 of the mixing actuator rod 1290 includes the flange 1293 and forms a distal surface 1294. The flange 1293 is disposed in the recess 1151 defined by the lock portion 1150 of the housing 1100. The distal surface 1294 of the mixing actuator rod 1290 is disposed within the lock portion 1150 of the housing 1100 substantially opposite the basket 1152 of the lock portion 1150. As shown, for example, in FIGS. 25 and 26, the distal surface 1294 can be concave and/or can be substantially conical with a diameter that decreases as the distal surface 1294 extends in the proximal direction. As described in further detail herein, the distal surface 1294 of the mixing actuator rod 1290, the lock portion 1150 of the housing 1100, and the lock portion 1705 of the safety lock 1700 collectively define and/or circumscribe a volume configured to receive the lock member 1730 (see e.g., FIGS. 25 and 26).

Figures 34, 35:
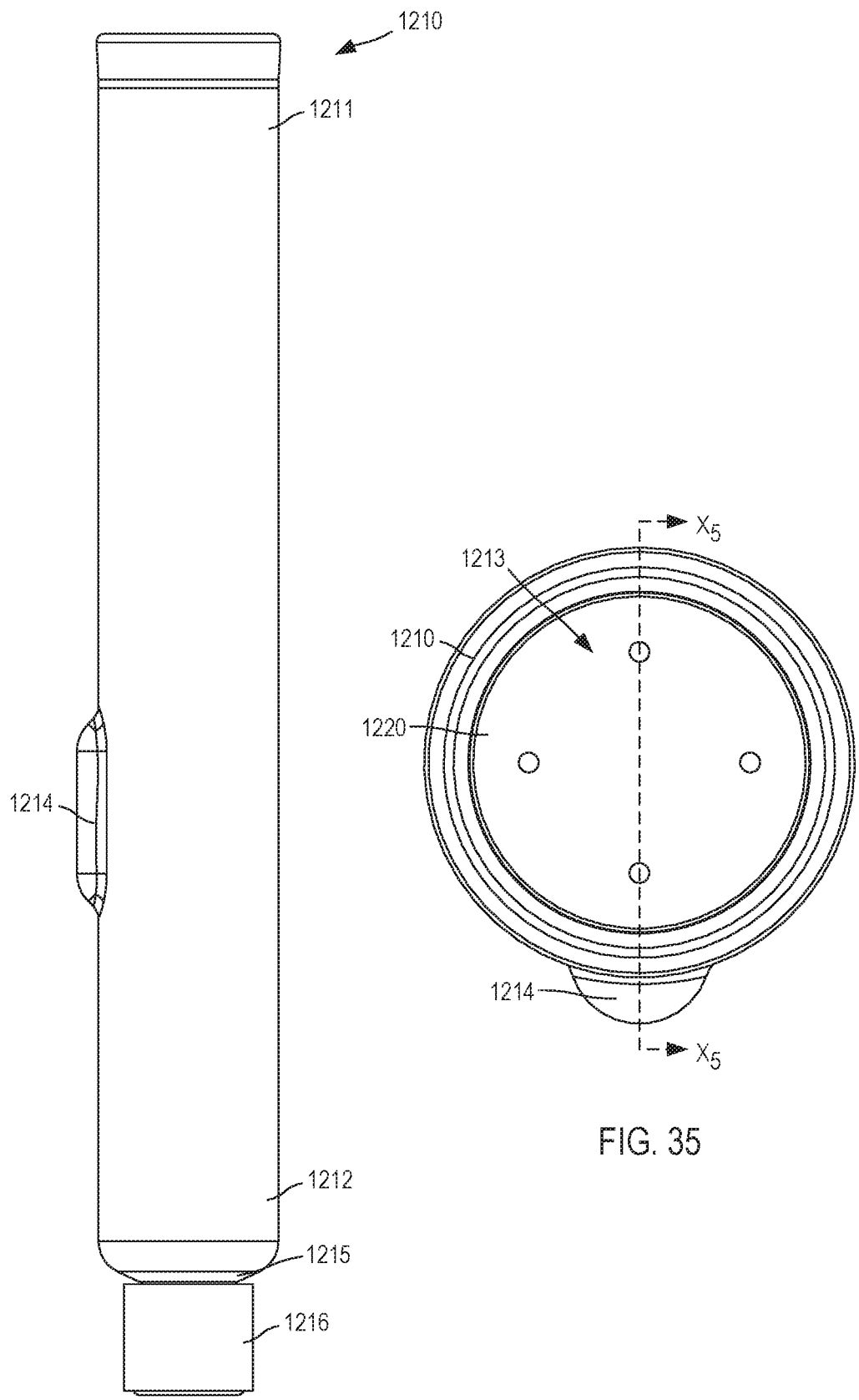
FIGS. 34 and 35 are a front view and a top view, respectively, of a medicament container included in the medicament delivery device of FIG. 11.
Figure 36:
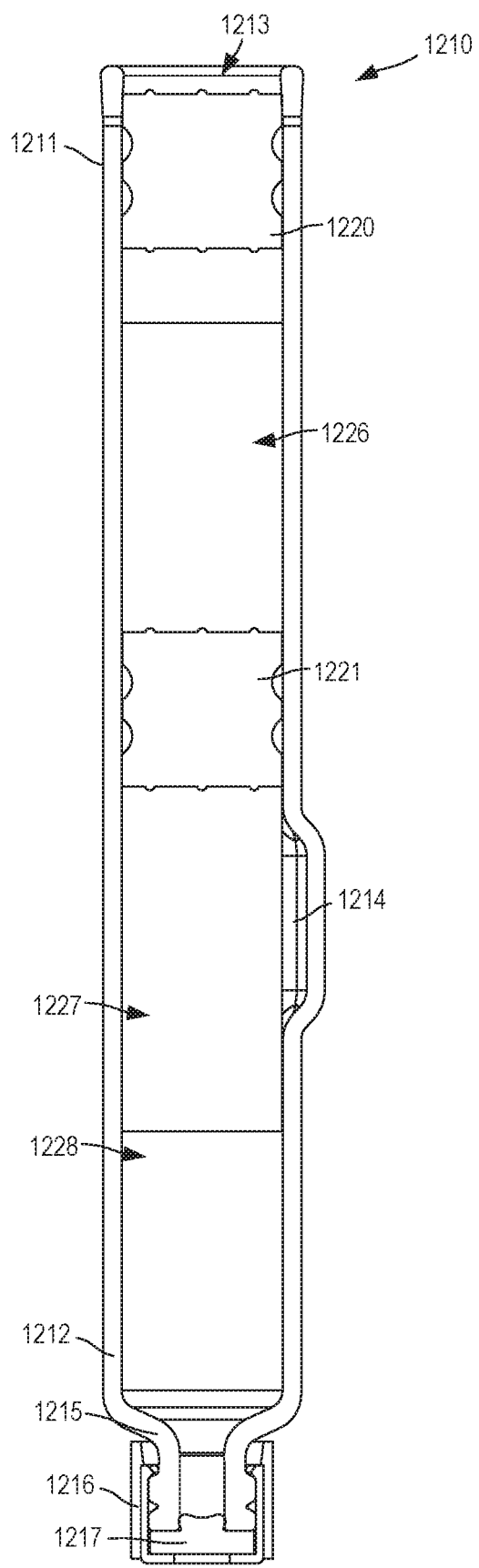
FIG. 36 is a cross-sectional view of the medicament container of FIG. 34 taken along the line $X_5$-$X_5$ in FIG. 35.

The medicament container 1210 includes a proximal end portion 1211, a distal end portion 1212, and defines an inner volume 1213 and a bypass 1214. The bypass 1214 can be a singular channel bypass or can define multiple channels. Although the bypass 1214 is shown in FIGS. 34 and 36 as an external bypass, in other embodiments, the bypass 1214 can be internal to the medicament container and/or a part of an elastomeric member disposed in the inner volume 1213. Said another way, in some embodiments a bypass can be configured such that the outer diameter of the medicament container 1210 is substantially constant. The bypass 1214 is configured to facilitate the mixing and/or injection of a medicament contained within the medicament container 1210, as described in further detail herein. In particular, the bypass 1214 is configured to place various volumes within the medicament container 1210 in fluid communication with each other.

As shown in FIGS. 34 and 36, the distal end portion 1212 of the medicament container 1210 includes a neck 1215 and a distal cap 1216 including a seal member 1217. The distal end portion 1212 is configured to be at least partially disposed within a container-mounting portion 1265 of the carrier 1260, as described below. The distal cap 1216 can be, for example, a crimp seal or cap disposed about the distal end portion 1212 of the medicament container 1210. The seal member 1217 can be any suitable member, such as, for example, a septum, a valve, a frangible seal, and/or the like. In this manner, the seal member 1217 is configured to engage a surface of the medicament container 1210 and an inner surface of the distal cap 1216 to define a fluidic seal, as described in further detail herein.

As described above, the proximal end portion 1211 of the medicament container 1210 is coupled to and/or otherwise includes the flange 1230. The flange 1230 includes the seal member 1235 (i.e., the outer seal) configured to form a substantially fluid tight seal with a portion of the inner surface 1130 of the housing 1100 that defines at least a portion of the medicament cavity 1141. The flange 1230 also includes the seal member 1236 (i.e., the inner seal) that forms a substantially fluid tight seal with an inner portion of the flange 1230 that defines at least a portion of the medicament cavity 1141.

The proximal end portion 1211 of the medicament container 1210 allows the inner volume 1213 to receive a first elastomeric member 1220 and a second elastomeric member 1221. In some embodiments, the first elastomeric member 1220 and the second elastomeric member 1221 are placed within the medicament container 1210 during a fill/finish process to define a diluent volume 1226 and a dry medicament volume 1227 (see, e.g., FIG. 36). Said another way, the diluent volume 1226 is a volume disposed within the medicament container 1210 defined between the first elastomeric member 1220 and the second elastomeric member 1221. The dry medicament volume 1227 is a volume disposed within medicament container 1210 defined between the second elastomeric member 1220 and the seal member 1217 disposed at the distal end portion 1213 of the medicament container 1210. As shown in FIG. 36, the diluent volume 1226 and the dry medicament volume 1227 are defined by the positions of the first elastomeric member 1220 and the second elastomeric member 1221 relative to and/or within the medicament container 1210. In some embodiments, the diluent volume 1226 can contain a medicament diluent, such as, for example, water. In some embodiments, the dry medicament volume 1227 can contain a lyophilized medicament (e.g., any suitable medicament produced via any suitable lyophilizing process) including any of the formulations and/or compositions described herein.

As shown in FIGS. 25 and 27, the proximal end portion 1211 of the medicament container 1210 is coupled to and/or receives a portion of the mixing protrusion 1162 of the proximal cap 1160. As described in further detail herein, the medicament container 1210 can be moved within the housing 1100 and relative to the mixing protrusion 1162, which in turn, can result in movement of the first elastomeric member 1220 and/or the second elastomeric member 1221 within the medicament container 1210. While the mixing protrusion 1162 is shown in FIG. 25 as being in contact with first elastomeric member 1220 prior to actuating the medical injector 1000 (e.g., when the medical injector 1000 is in a storage, or first, configuration), in other embodiments, the mixing protrusion 1162 can be spaced apart from the first elastomeric member 1220 when the medical injector 1000 is in the storage configuration.

The medicament container 1210 can have any suitable size (e.g., length and/or diameter). In some embodiments, the medicament container 1210 and/or the mixing protrusion 1162 of the proximal cap 1160 can be configured (collectively or independently) such that the medicament container 1210 travels a desired distance during a mixing event (i.e., a "mixing stroke"). In this manner, the medicament container 1210, the diluent contained within the diluent volume 1226, the lyophilized medicament contained within the dry medicament volume 1227, and the mixing protrusion 1162 can be collectively configured to provide a desired fill volume and delivery volume. Moreover, the length of the medicament container 1210 and the length of the mixing protrusion 1162 can be configured such that the medicament container assembly 1200 can fit in the same housing 1100 regardless of the fill volume, the delivery volume, and/or the ratio of the fill volume to the delivery volume. In this manner, the same housing 1100 and production tooling can be used to produce devices having various dosages of the medicament. For example, in a first embodiment (e.g., having a fill volume to delivery volume ratio of 0.4), a medicament container has a first length and a mixing protrusion has a first length. In a second embodiment (e.g., having a fill volume to delivery volume ratio of 0.6), a medicament container has a second length shorter than the first length, and a mixing protrusion has a second length longer than the first length. In this manner, the mixing stroke of the device of the second embodiment is longer than that of the device of the first embodiment, thereby allowing mixing of a greater dosage. The medicament container of the device of the second embodiment, however, is shorter than the medicament container of the device of the first embodiment, thereby allowing the components of both embodiments to be disposed within the same housing and/or a housing having the same length.

The first elastomeric member 1220 and the second elastomeric member 1221 can be of any design or formulation suitable for contact with the medicament (e.g., the diluent contained in the diluent volume 1226 and/or a lyophilized medicament contained in the dry medicament volume 1227). For example, the elastomeric members 1220 and 1221 can be formulated to minimize any reduction in the efficacy of the medicament that may result from contact (either direct or indirect) between the elastomeric members 1220 and 1221 and the medicament. In some embodiments, the elastomeric members 1220 and 1221 can be made from and/or can include butyl rubber, such as chlorobutyl rubber, bromobutyl rubber, and/or the like. In some embodiments, the first elastomeric member 1220 and the second elastomeric member 1221 can be formulated to minimize any leaching or out-gassing of compositions that may have an undesired effect on the medicament. In other embodiments, the elastomeric members 1220 and 1221 can be formulated to maintain its chemical stability, flexibility and/or sealing properties when in contact (either direct or indirect) with the medicament over a long period of time (e.g., for up to six months, one year, two years, five years or longer).

Figure 39:
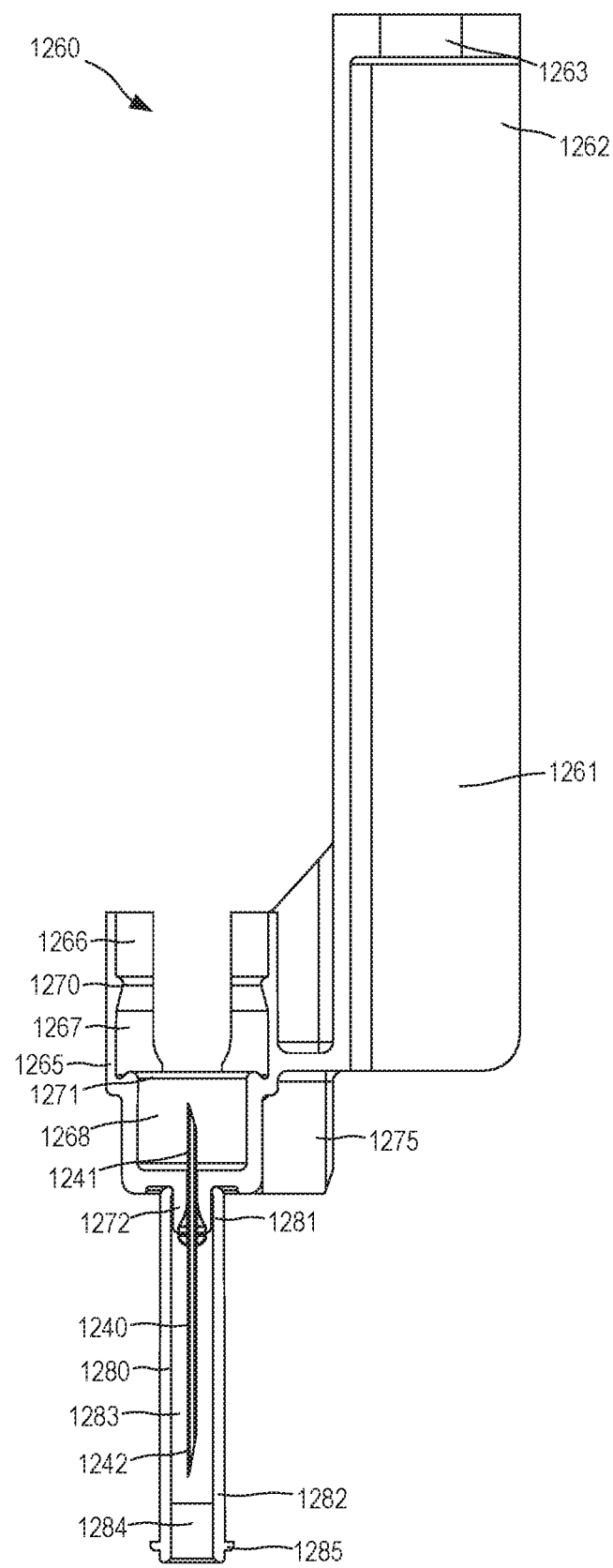
FIG. 39 is a cross-sectional view of the carrier of FIG. 27 taken along the line $X_6$-$X_6$ in FIG. 28.
Figure 41:
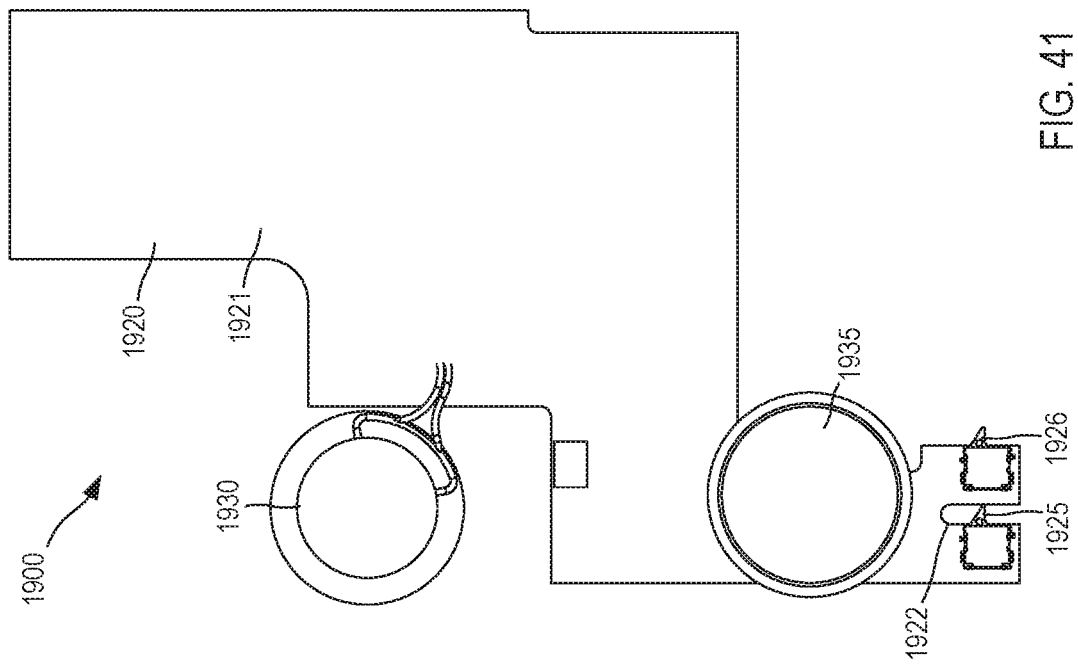
FIGS. 40 and 41 are a front view and a rear view of an electronic circuit system included in the medicament delivery device of FIG. 11.
Figure 40:
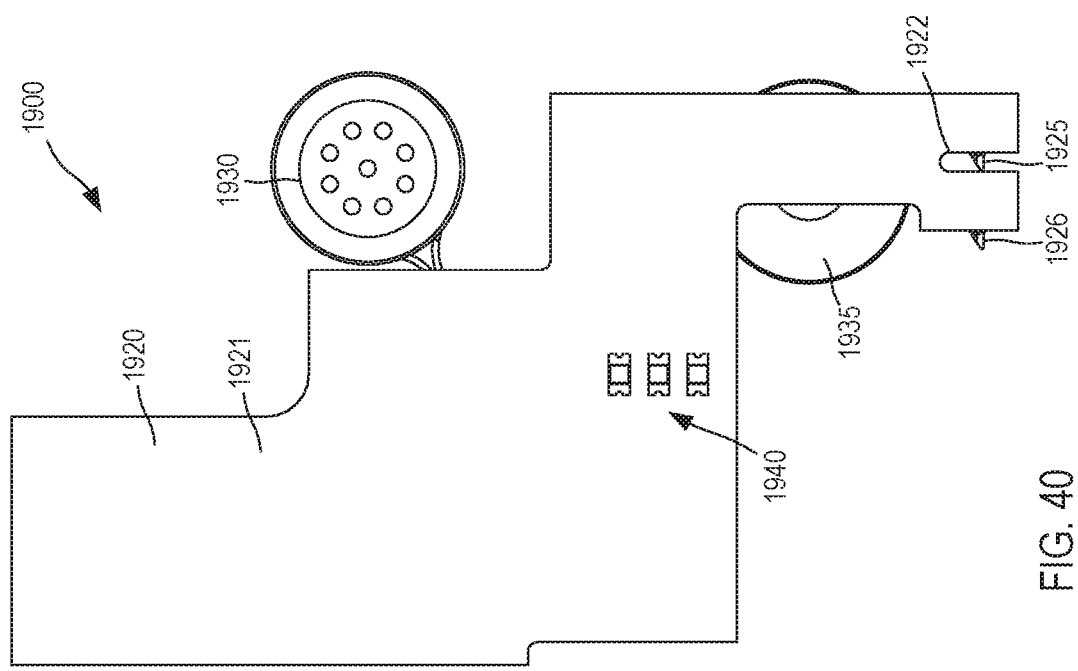
Figure 42:
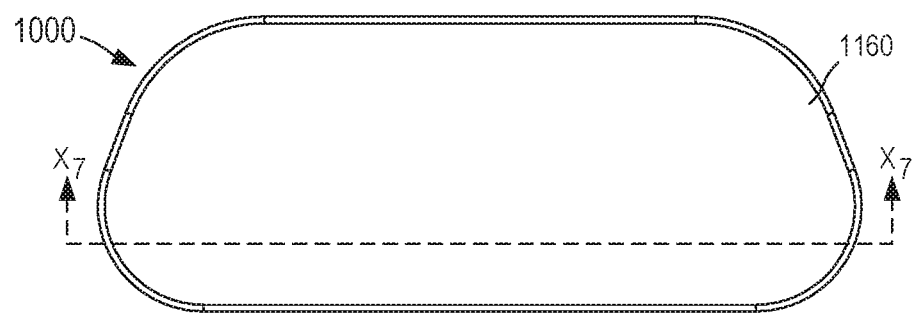
FIG. 42 is a top view of the medicament delivery device of FIG. 11.
Figure 43:
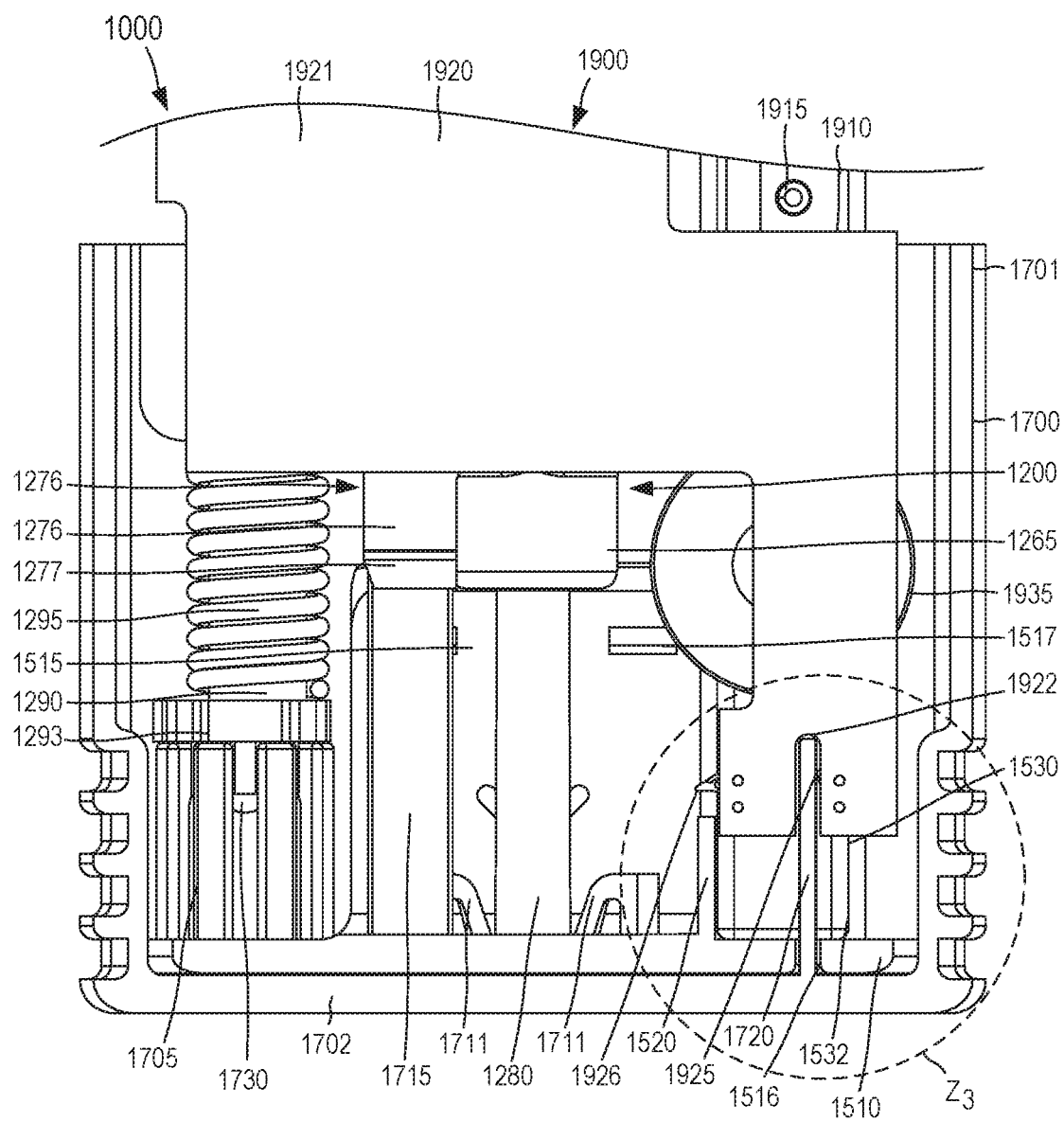
FIG. 43 is a cross-sectional view of a portion of the medicament delivery device of FIG. 11 in the second configuration (i.e., with the case removed and the safety lock in the "locked" position) taken along the line $X_7$-$X_7$ in FIG. 42.

As described above, the medicament container 1210 is configured to engage and/or be coupled to the carrier 1260 (see e.g., FIGS. 25, 27 and 37-39). Referring to FIGS. 37-39, the carrier 1260 includes the mixing portion 1261, the container-mounting portion 1265, the lock portion 1275, the needle 1240, and the needle sheath 1280. The mixing portion 1261 extends from the container-mounting portion 1265 and the lock portion 1275. As shown in FIG. 37, the mixing portion 1261 includes a proximal flange 1262 that defines an opening 1263. The opening 1263 is configured to receive a portion of the mixing actuator rod 1290. The arrangement of the opening 1263 is such that the proximal flange 1262 is movably disposed about the mixing actuator rod 1290 (i.e., the proximal flange 1262 and the carrier 1260 can slide about the actuator rod 1290). Moreover, as shown in FIG. 25, the arrangement of the medicament container assembly 1200 is such that the bias member 1295 is disposed about the mixing actuator rod 1290 and between the flange 1293 at the distal end portion 1292 of the mixing rod actuator 1290 and the proximal flange 1262 of the carrier 1260. In this manner, the medical injector 1000 can be actuated to transition the bias member 1295 from a first configuration with a relatively high potential energy (e.g., a compressed configuration) to a second configuration with a relatively low potential energy (e.g., a non-compressed configuration) to exert a force on the proximal flange 1262 of the mixing portion 1261 of the carrier 1260 sufficient to move the carrier 1260 within the mixing actuator cavity 1142 in the proximal direction, as described in further detail herein.

The container-mounting portion 1265 of the carrier 1260 includes and/or forms a substantially annular wall within which a portion of the medicament container 1210 is disposed. More specifically, the container-mounting portion 1265 includes an inner surface 1266 with a first portion 1267 and a second portion 1268 (see e.g., FIG. 39). In this embodiment, the first portion 1267 of the inner surface 1266 has a diameter that is greater than a diameter of the second portion 1268. The diameter of the first portion 1267 and the diameter of the second portion 1268 can each be associated with a diameter of a different portion of the medicament container 1210, thereby allowing the medicament container 1210 to selectively engage the container-mounting portion 1265 in various positions during the various stages of operation of the medical injector 1000. As shown in FIG. 39, the first portion 1267 of the inner surface 1266 includes a first shoulder 1270. Similarly, the inner surface 1266 includes a second shoulder 1271 disposed at or near a transition from the first portion 1267 to the second portion 1268. In this manner, the container-mounting portion 1265 of the carrier 1260 can selectively engage a corresponding portion of the medicament container 1210 to at least temporarily maintain the medicament container 1210 in a fixed position relative to the carrier 1260, as described in further detail herein. Furthermore the container-mounting portion 1265 includes a needle mount 1272 configured to couple the needle 1240 to the carrier 1260 such that a proximal end portion 1241 of the needle 1240 is disposed within a volume circumscribed by the second portion 1268 of the inner surface 1266 (see e.g., FIG. 39).

As shown in FIG. 37, the lock portion 1275 of the carrier 1260 includes a first member 1276 having a tab 1277, and a second member 1278 having a tab 1279. The lock portion 1275 is configured such that a space is defined between the first member 1276 and the second member 1278. As described above, the carrier 1260 can be disposed in the medicament cavity 1241 such that the tabs 1277 and 1279 are disposed in the corresponding carrier lock apertures 1113 defined by the housing 1100. In some embodiments, the arrangement of the lock portion 1275 can be such that the tabs 1277 and 1279 engage a surface of the housing 1100 defining the carrier lock apertures 1113 (e.g., a proximal surface). In this manner, the lock portion 1275 limits a proximal movement of the carrier 1260 prior to actuating the medical injector 1000.

As shown in FIGS. 37 and 39, the needle 1240 includes the proximal end portion 1241 and a distal end portion 1242. In this embodiment, the proximal end portion 1241 and the distal end portion 1242 are each sharpened (or beveled). In other embodiments, the proximal end portion 1241 and/or the distal end portion 1242 need not be sharpened. The needle 1240 is coupled to the carrier 1260 such that the proximal end portion 1241 of the needle 1240 is at least partially disposed within the volume circumscribed by the second portion 1268 of the inner surface 1266. At least a portion of the needle 1240 is configured to be disposed within the needle sheath 1280 prior to actuating the medical injector 1000. The needle sheath 1280 includes a proximal end portion 1281, a distal end portion 1282, and a rib 1285. The needle sheath 1280 also defines a bore 1283 within which a needle plug 1284 is disposed at or near the distal end portion 1282 of the needle sheath 1280. As shown in FIG. 39, the needle sheath 1280 is at least temporarily disposed about a portion of the needle mount 1272 to define a friction fit, a snap fit, and/or the like. Thus, the needle sheath 1280 can be coupled to the carrier 1260 and about the needle 1240 until a force is exerted that is sufficient to remove the needle sheath 1280 from the carrier 1260. The needle plug 1824 can be any suitable material such as a cork material or any other suitable porous material (e.g., any suitable Porex™ material) to allow for exposure to ethylene oxide during a sterilization operation. As such, the needle sheath 1280 can be disposed about the needle 1240 prior to use of the medical injector 1000 to substantially maintain the sterility of the needle 1240 and to prevent inadvertent contact with the sharpened distal end 1241 thereof.

While the needle 1240 is shown and described above as being coupled to the carrier 1260, in other embodiments, the needle 1240 can be monolithically formed with the carrier 1260. Similarly, in some embodiments, the needle 1240 can be coupled to or monolithically formed with the medicament container 1210. Thus, during manufacturing and/or assembly the needle 1240 and the carrier 1260 and/or the medicament container 1210, as well as the needle sheath 1280 disposed about a portion of the needle 1280, can be maintained in an aseptic environment, which in some instances, can obviate a need for further sterilization such as, for example, ethylene oxide.

FIGS. 40-46 illustrate the electronic circuit system 1900 included in the medical injector 1000. The electronic circuit system 1900 includes a printed circuit board 1920, a battery assembly 1935, an audio output device 1930, three light emitting diodes (LEDs) 1940, a battery clip 1910 (see e.g., FIG. 50), a first switch 1925, and a second switch 1926. The electronic circuit system 1900 is disposed within the housing 1100 (see e.g., FIG. 50) and is configured to output an electronic output associated with the use of the medical injector 1000.

In some embodiments, the electronic circuit system 1900 can be coupled to the housing 1100 by any suitable means such as an adhesive, a clip, a label, and/or the like. For example, the electronic circuit system 1900 includes a batter clip 1910 coupled to the housing 1100. As described in more detail herein, the battery clip protrusion 1136 (see FIG. 50) of the housing 1100 is configured to hold the battery clip 1910 in place. Similarly stated, the battery clip protrusion 1136 of the housing 1100 is configured to exert a force on the battery clip 1910 to ensure that electrical contact between the battery assembly 1935 and the battery clip 1910 is maintained when the battery isolation protrusion 1185 of the cover 1180 is removed, as described in further detail herein.

As shown and described above with respect to FIG. 16, the housing 1100 defines the sounds apertures 1108, the LED aperture 1115, the system activation opening 1124, and the electronic activation opening 1125. The electronic circuit system 1900 is disposed in the housing 1100 such that a front face of the audio output device 1930 is disposed adjacent the sound apertures 1108. In this manner, the sound apertures 1108 are configured to allow sound produced by the audio output device 1930 to pass from the audio output device 1930 to a region outside of the housing 1100.

The printed circuit board 1920 of the electronic circuit system 1900 includes a substrate 1921, the first switch 1925, and the second switch 1926. In addition, the printed circuit board 1920 defines a notch 1922 (see e.g., FIGS. 40 and 41). Although not specifically shown herein, the substrate 1921 of the printed circuit board 1920 includes and/or is otherwise coupled to any suitable electrical components for the electronic circuit system 1900 to operate as desired. For example, the electrical components can be one or more resistors, capacitors, inductors, switches, accelerometers, microcontrollers, microprocessors and/or the like. The printed circuit board 1920 may also be constructed of materials other than a flexible substrate, such as a FR4 standard board (rigid circuit board).

As shown in FIGS. 43-46, the first switch 1925 is disposed on the substrate 1921 such that a portion of the first switch 1925 extends into the notch 1922 defined by the printed circuit board 1920. Similarly, the second switch 1926 is disposed on the substrate 1921 such that a portion of the second switch 1926 extends beyond a boundary (e.g., an edge or contour) of the printed circuit board 1920. In this manner, the first switch 1925 and the second switch 1926 can be actuated, activated, and/or otherwise engaged to transition between a first configuration, associated with a first electrical state, and a second configuration, associated with a second electrical state. In some embodiments, the first switch 1925 and the second switch 1926 can be a reversible electromechanical switch and/or a reversible optical switch. In other embodiments, the first switch 1925 and the second switch 1926 can be an engagement or frangible portion of an electrical circuit. In such embodiments, the first switch 1925 and the second switch 1926 can be, for example, an irreversible switch of the types shown and described in U.S. Pat. No. 7,731,686, entitled "Devices, Systems and Methods for Medicament Delivery," filed Jan. 9, 2007, which is incorporated herein by reference in its entirety. In this embodiment, the first switch 1925 and the second switch 1926 are reversible electromechanical switches that can be manipulated to open or close an electrical circuit. In other embodiments, a button, toggle, dial, switch, and/or other mechanism may be used to transition the electronic circuit system 1900 between an on or off state.

Figure 44:
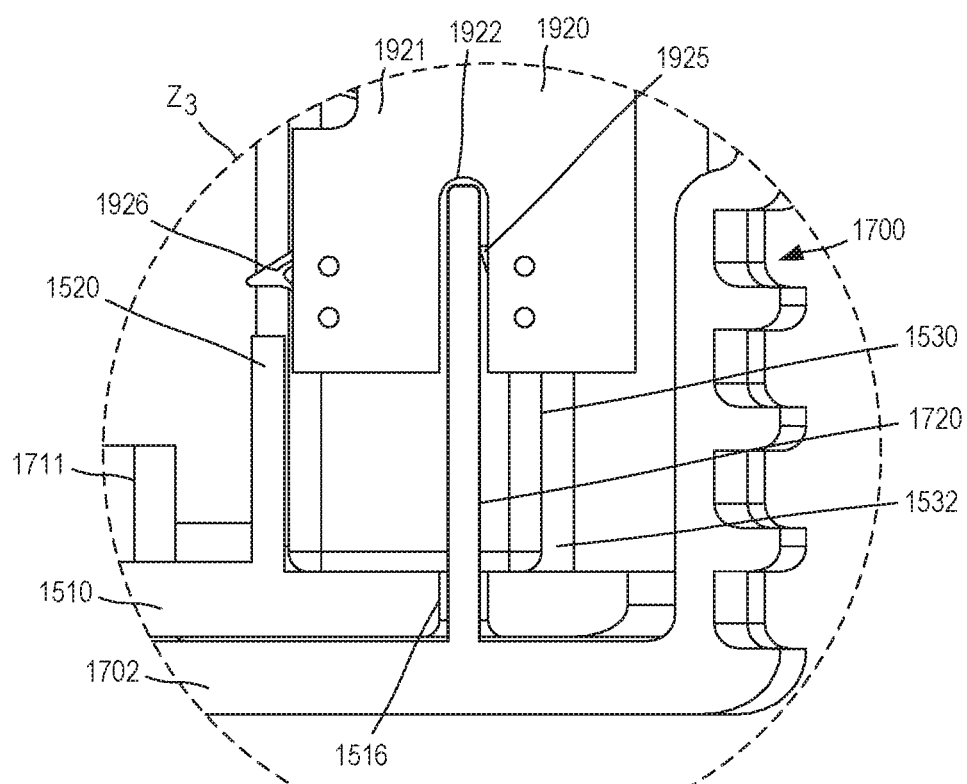
FIGS. 44-46 are enlarged views of a portion of the medicament delivery device of FIG. 11 identified by the region $Z_3$ in FIG. 43, in a second configuration, a third configuration (i.e., with the safety lock removed), and sixth configuration (i.e., after actuation of the injection event), respectively.
Figure 45:
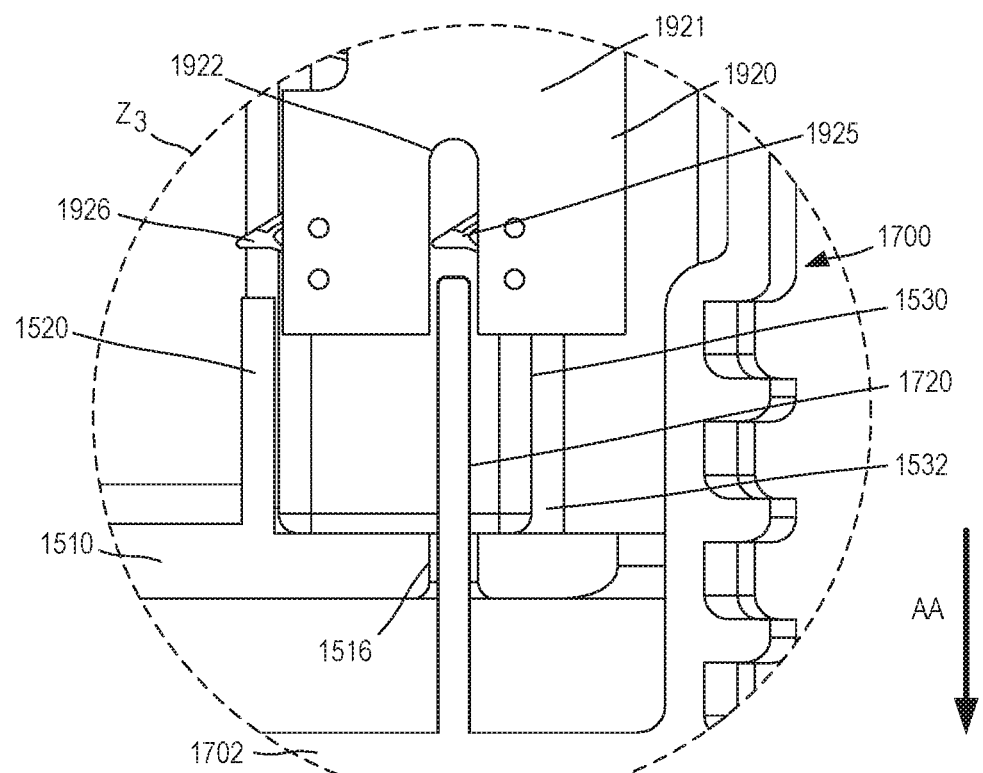

Specifically, as shown in FIG. 44, the safety lock (or mixing actuator) 1700 includes the electronic activation protrusion 1720 that is at least partially disposed in the notch 1922 defined by the printed circuit board 1920 when the safety lock 1700 is coupled to the housing 1100 (e.g., when the medical injector 1000 is in a storage configuration and/or prior to use). With the electronic activation protrusion 1720 disposed in the notch 1922, the first switch 1925 is in a first configuration. That is to say, the electronic activation protrusion 1720 can engage the portion of the first switch 1925 that is disposed in the notch 1922 (described above) to place and/or maintain the first switch 1925 in its first configuration. In use, the safety lock 1700 can be manipulated and removed from the housing 1100, thereby initiating the mixing operation and enabling actuation of the device 1000. Movement of the safety lock 1700 also moves the electronic activation protrusion 1720 relative to the electronic circuit system 1900. As indicated by the arrow AA in FIG. 45, the movement of the safety lock 1700 moves the electronic activation protrusion 1720 out of the notch 1922 defined by the printed circuit board 1920 and thus, out of engagement with the first switch 1925. Thus, with the electronic activation protrusion 1720 out of engagement with the first switch 1925, the first switch 1925 can transition to its second configuration, as shown in FIG. 45 (e.g., the first switch 1925 can be biased or the like to transition to its second configuration).

Figure 46:
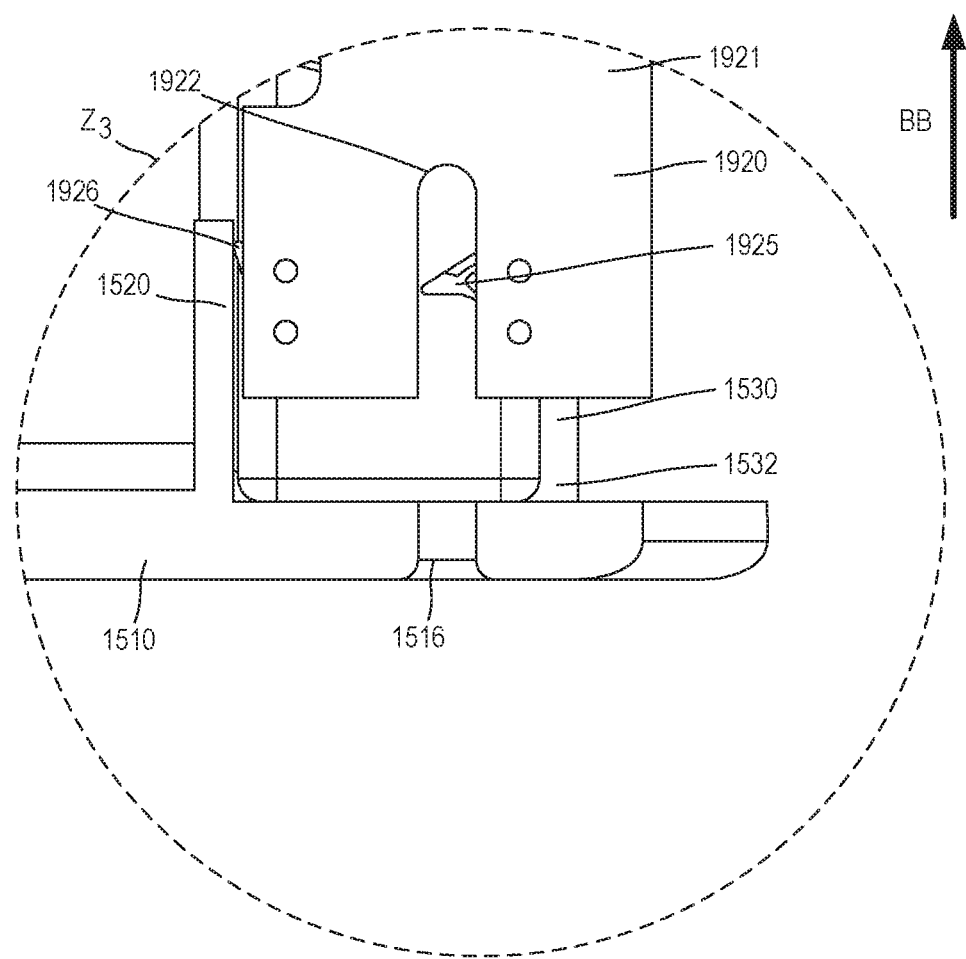
Figure 47:
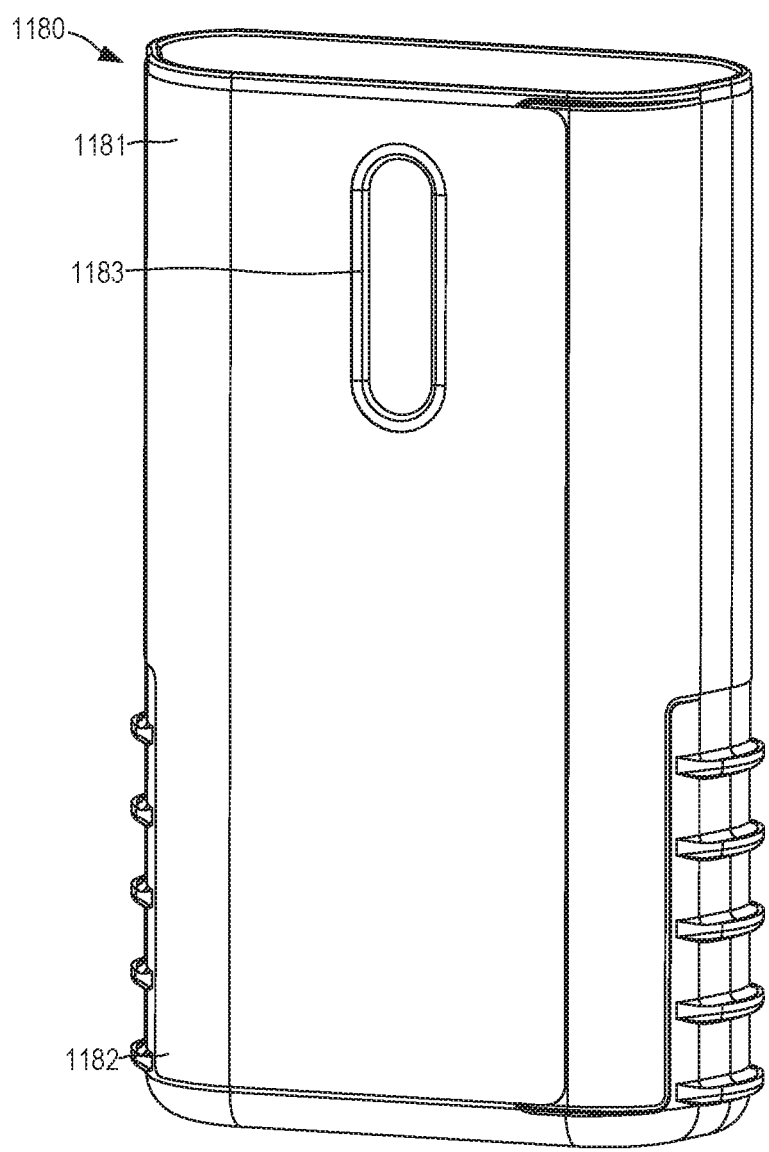
FIGS. 47 and 48 are a front perspective view and a top perspective view, respectively, of a case included in the medicament delivery device of FIG. 11.

In a similar manner, the second switch 1926 can be engaged by the electronic activation protrusion 1520 (see, e.g., FIG. 29) of the base 1510. For example, as shown in FIGS. 44 and 45, the base 1510 can be disposed in its first position relative to the housing 1100 (e.g., the retention members 1519 of the base 1510 are disposed in and/or otherwise in contact with the distal actuator retention notches 1112) such that the electronic activation protrusion 1520 of the base 1510 is disposed in a distal position relative to the second switch 1926. That is to say, the electronic activation protrusion 1520 is not in contact with and/or otherwise does not engage the second switch 1926 when the base 1510 is in its first position relative to the housing 1100. In use, once the safety lock 1700 has been removed from the housing 1100, the base 1510 can be moved toward its second position relative to the housing 1100, as indicated by the arrow BB in FIG. 46. As described below, movement of the base 1510 actuates the system actuator assembly 1500. The movement of the base 1510 also moves the electronic activation protrusion 1520 of the base 1510 in, for example, the proximal direction and into contact and/or engagement with the second switch 1926. Thus, the electronic activation protrusion 1520 of the base 1510 transitions the second switch 1926 from its first configuration to its second configuration, as shown in FIG. 46. Thus, the first switch 1925 and the second switch 1926 can be actuated and/or activated to transition between a first electric state and a second electric state, which in turn, can cause the electronic circuit system 1900 to perform one or more electronic operations, as described in further detail herein.

Figure 50:
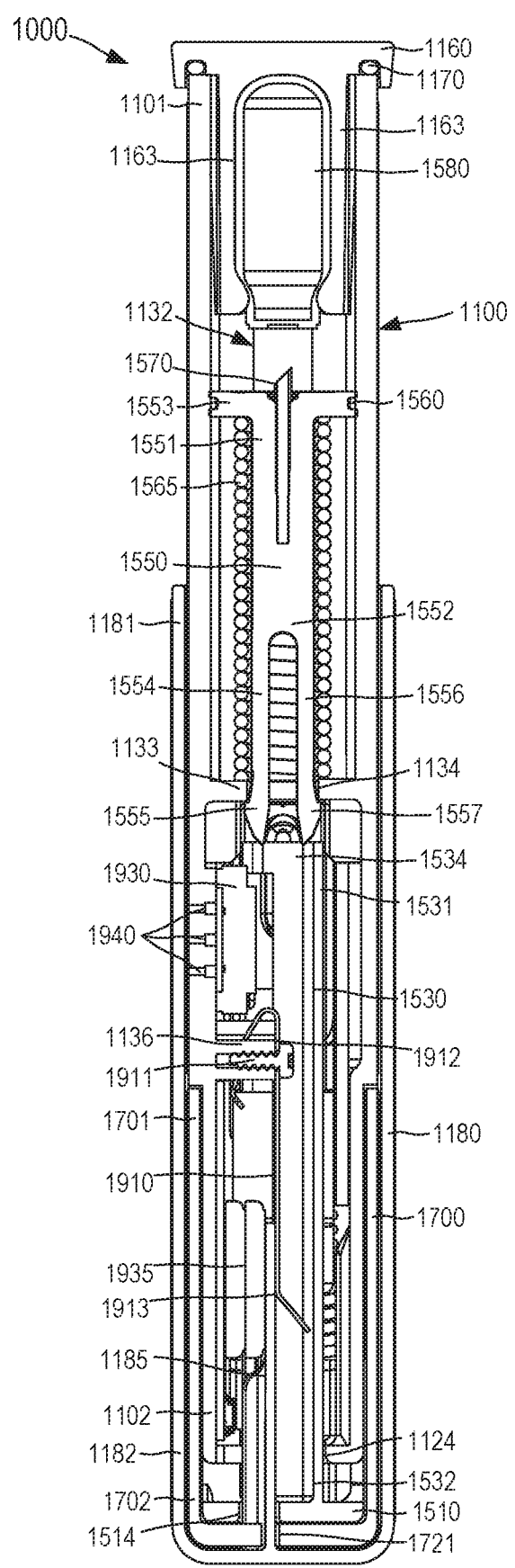
FIG. 50 is a cross-sectional view of the medicament delivery device of FIG. 11 in the first configuration, taken along the line $X_8$-$X_8$ in FIG. 49.

The battery clip 1910 (shown in FIG. 50) includes an attachment portion 1912 and a contact portion 1913. The attachment portion 1912 receives a screw 1911 to couple the battery clip 1910 to the battery clip protrusion 1136 of the housing 1100. In this manner, the battery clip protrusion 1136 maintains the position of the battery clip 1910 with respect to the printed circuit board 1920. The contact portion 1913 of the battery clip 1910 is configured to selectively contact a surface of the battery assembly 1935 when the cover 1180 is removed from the housing 1100, as described below. Note that FIG. 50 shows the injector 1000 in the first (or initial) configuration, in which the battery isolation protrusion 1185 is disposed between the contact portion 1913 of the battery clip 1910 and the second surface of the battery assembly 1935.

The battery assembly 1935 of the electronic circuit system 1900 includes two batteries stacked on top of one another. In other embodiments, the electronic circuit system can include any number of batteries and/or any suitable type of power source. In some embodiments, for example, the battery assembly can include Lithium batteries such as, for example, CR11616, CR12016s, type AAA or the like. The battery assembly 1935 has a first surface that can contact, for example, an electrical contact (not shown) disposed on the printed circuit board 1920, and a second surface that can selectively contact, for example, the contact portion 1913 of the battery clip 1910 (see e.g., FIG. 50). More particularly, when the cover 1180 is coupled to the housing 1100, a portion of the battery isolation protrusion 1185 is disposed between the contact portion 1913 of the battery clip 1910 and the second surface of the battery assembly 1935, thereby maintaining electric isolation therebetween. When the cover 1180 is removed from the housing 1100, the battery isolation protrusion 1185 is likewise removed from the housing 1100 and the contact portion 1913 of the battery clip 1910 is placed in contact with the second surface of the battery assembly 1935 (e.g., the battery clip 1910 is biased or the like to place the contact portion 1913 in contact with the battery assembly 1935). When both the electrical contact of the substrate 1921 and the contact portion 1913 of the battery clip 1910 contact the battery assembly 1935, the batteries of the battery assembly 1935 are placed in electrical communication with the electronic circuit system 1900. Said another way, when the electrical contact of the substrate 1921 and the contact portion 1913 of the battery clip 1910 contact the battery assembly 1935, the battery assembly 1935 is configured to supply power to the electronic circuit system 1900.

The audio output device 1930 of the electronic circuit system 1900 is configured to output audible sound to a user in response to use of the medical injector 1000. In some embodiments, the audible output device 1930 can be a speaker. In some embodiments, the audible sound can be, for example, associated with a recorded message and/or a recorded speech. In other embodiments, the audible instructions can be an audible beep, buzzer, a series of tones and/or or the like. Moreover, when the electrical contact on the printed circuit board 1920 and the contact portion 1913 of the battery clip 1910 are in contact with the battery assembly 1935, the battery assembly 1935 can supply electrical power to the electronic circuit system 1900, which is operable in causing the audio output device 1930 to output audible sound.

Although not shown, in some embodiments, the electronic circuit system 1900 can have a network interface device configured to operatively connect the electronic circuit system 1900 to a remote device (not shown) and/or a communications network (not shown). In this manner, the electronic circuit system 1900 can send information to and/or receive information from the remote device. The remote device can be, for example, a remote communications network, a computer, a compliance-monitoring device, a cell phone, a personal digital assistant (PDA), and/or the like. Such an arrangement can be used, for example, to download replacement processor-readable code from a central network to the electronic circuit system 1900. In some embodiments, for example, the electronic circuit system 1900 can download information associated with a medical injector 1000, such as an expiration date, a recall notice, updated use instructions or the like. Similarly, in some embodiments, the electronic circuit system 1900 can upload compliance information associated with the use of the medical injector 1000 via the network interface device.

Although not shown, in some embodiments, the electronic circuit system 1900 can include a radio (also referred to as a receiver, transmitter and/or transceiver) operable to send signals to, and/or receive radio signals, such as Bluetooth®, ZigBee, WiFi, cellular telephone signals, etc. For example, in some embodiments, the electronic circuit system 1900 includes components of and/or operates in accordance with the methods described in U.S. Patent Publication No. 2014/0243749, entitled "Devices, Systems and Methods for Locating and Interacting with Medicament Delivery Systems," filed Dec. 27, 2013, which is incorporated herein by reference in its entirety. For example, in some embodiments, the electronic circuit system can include a Bluetooth® processor having an integral radio. In other embodiments, the radio can include a processor distinct from the "primary" processor.

Although not shown, in some embodiments, the electronic circuit system 1900 can include an orientation sensor, an accelerometer, an optical sensor, and/or any other suitable "shake" sensor. Similarly stated, the electronic circuit system 1900 can include a sensor that can determine physical differences before and after user actions (e.g., such as shaking, rotating, or the like). In this manner, the electronic circuit system 1900 can produce one or more outputs associated with the orientation of the medical injector 1000 during use. For example, in some embodiments, the electronic circuit system 1900 can produce an alarm (beep or buzzer) or other output to indicate when the needle is outside of a predetermined "vertical" range. Specifically, during the mixing process, it is advantageous for the needle 1240 to be pointed upwards within a predetermined angular range of vertical. Similarly stated, it is advantageous for a longitudinal axis of the needle 1240 to be parallel and/or aligned with a vertical axis (or within a predetermined angular range of the vertical axis). In this manner, distal end portion 1242 of the needle 1240 will be pointed upwards during the mixing process to allow any air trapped within the medicament container 1210 to escape via the needle 1240 (e.g., a priming step). By producing an output via the electronic circuit system 1900, the medical injector 1000 can alert the user that the orientation of the device is not suitable for initiation of the mixing operation.

In some embodiments, the orientation sensor can sense if the medical injector 1000 has been placed in contact with a patient in a desired orientation, position and/or manner. In this arrangement, other sensors can be used along with the orientation sensor and/or accelerometer in order to determine relative position and/or orientation of the medical injector 1000. For example, in some embodiments, the medical injector 1000 can be configured to expose a relatively small portion of the needle 1240 during subcutaneous injection. Thus, the orientation sensor and/or any other sensor can be used to sense when the medical injector 1000 is substantially perpendicular to an injection surface (i.e., approximately 90 degrees to a tangent line of the injection surface) of the patient to allow for proper insertion of the exposed portion of the needle 1240. In addition to sensing the orientation and/or position of the medical injector 1000, the orientation sensor and/or any other sensor included in the electronic circuit system 1900 can be configured to send a signal, for example, to a processor, which in turn, can cause an audible output (e.g., via the audio device 1930), a visual output (e.g., via the LEDs 1940), and/or any other suitable electronic output (e.g., a haptic output and/or the like) to alert the user if the medical injector 1000 is not disposed in a proper position and/or orientation during a given phase of an injection event.

In other embodiments, the electronic circuit system 1900 can produce an indication associated with rapid movement or shaking of the injection device 1000. For example, in some embodiments, the electronic circuit system 1900 can produce an audible instruction for the user to shake the device for five seconds after removing the safety lock (or mixing actuator) 1700. The accelerometer can then sense the rapid motion or shaking of the injection device 1000, and produce a countdown timer starting when the shaking motion is first detected (i.e., exceeds a predetermined threshold), and continuing while the shaking motion continues. In some embodiments, the electronic circuit system 1900 can stop the countdown timer if the shaking motion stops or otherwise drops below a predetermined threshold. In this manner, the user is prompted to continue the shaking (rather than having the countdown timer being simply a "timed script").

In yet other embodiments, the electronic circuit system 1900 can include a sensor (e.g., an optical sensor) that can produce a signal associated with the status of mixing. For example, the sensor can detect solid particles (e.g., portions of the lyophilized medicament) indicating that the dry medicament has not yet been fully mixed. In response to the signal, the electronic circuit system can produce a light, an audible output, or the like, instructing the user to continue shaking the device.

FIGS. 47-50 show the cover 1180 of the medical injector 1000. The cover 1180 can be any suitable configuration and can include any suitable feature to house, contain and/or protect portions of the medical injector 1000. The cover 1180 includes a proximal end portion 1181 and a distal end portion 1182, and defines a cavity 1184 and a set of status windows 1183. The cavity 1184 of the cover 1180 is configured to receive at least a portion of the housing 1100. The status windows 1183 are disposed on opposite sides of the cover 1180 and are configured such that, when the portion of the housing 1100 is disposed within the cover 1180, the status windows 1183 of the cover 1180 are at least partially aligned with the corresponding status indicator aperture 1107 of the housing 1100. Thus, a user can visually inspect a portion of the medicament container assembly 1200 via the status windows 1183 of the cover 1180 and the status indicator apertures 1107 of the housing 1100. As described above, the electronic circuit system 1900 can be actuated only when the housing 1100 is at least partially removed from the cover 1180. Thus, the cover 1180 also functions as a safety lock to limit medicament delivery.

Figure 48:
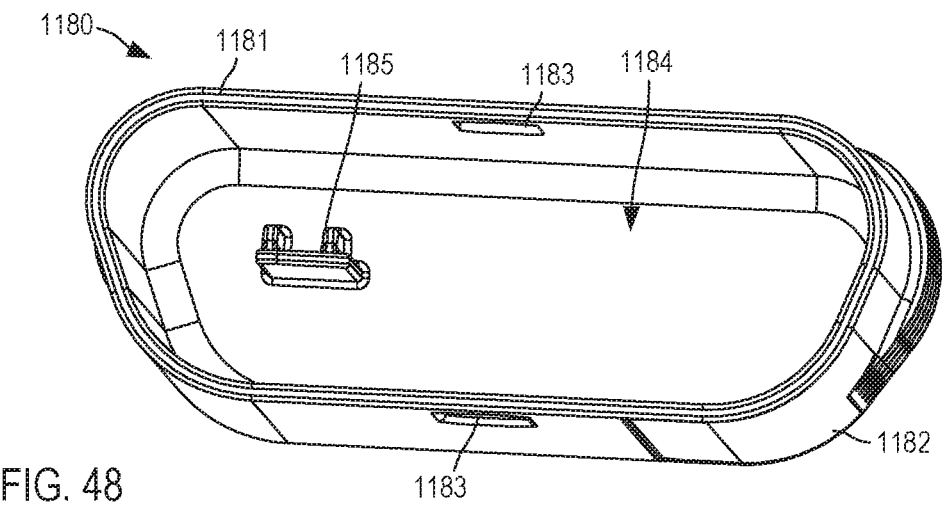
Figure 49:
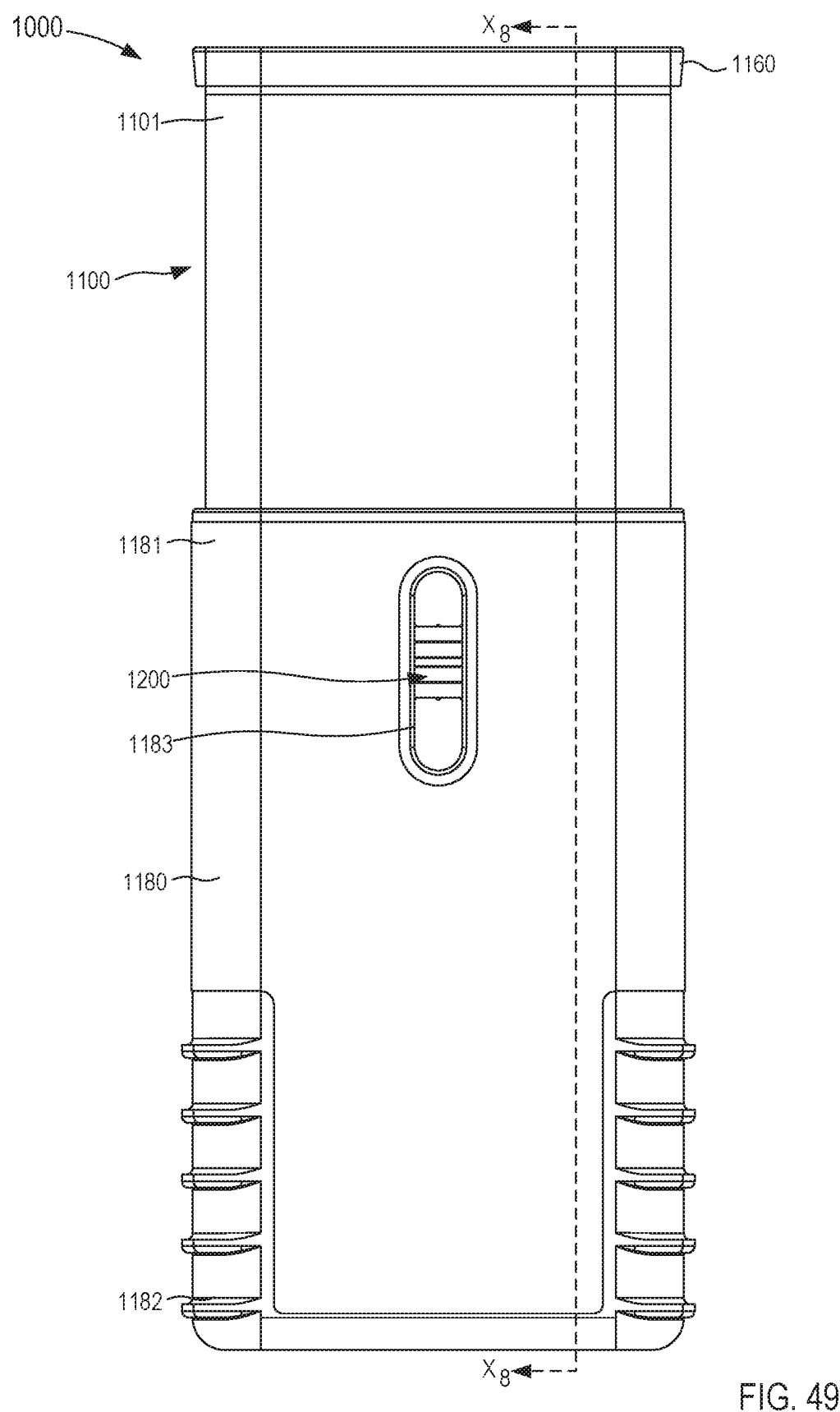
FIG. 49 is a front view of the medicament delivery device of FIG. 11 in the first configuration.

As shown in FIG. 48, the distal end portion 1182 of the cover 1180 includes the battery isolation protrusion 1185 disposed in the cavity 1184. As described above, the battery isolation protrusion 1185 is configured to be removably disposed between the second surface of the battery assembly 1935 and the contact portion 1913 of the battery clip 1910 (see e.g., FIG. 50).

FIGS. 51-54 show the safety lock (or mixing actuator) 1700 of the medical injector 1000. The safety lock 1700 of the medical injector 1000 includes a proximal end portion 1701, a distal end portion 1702, and an inner surface 1704 that defines an inner volume 1707. The safety lock 1700 defines a lock portion opening 1709, a needle sheath aperture 1725 and a battery isolation protrusion aperture 1721. The lock portion opening 1709 is configured to receive, at least in part, the lock portion 1150 of the housing 1100, as described in further detail herein. The needle sheath aperture 1725 is configured to receive a portion of the needle sheath 1280. The battery isolation protrusion aperture 1721 is configured to receive the battery isolation protrusion 1185 of the cover 1180. As such, the battery isolation protrusion 1185 can extend through the battery isolation protrusion aperture 1721 of the safety lock 1700, the battery isolation protrusion opening 1516 of the base 1510, and the system activation opening 1124 to be partially disposed within the housing 1100 and/or in engagement with the electronic circuit system 1900, as described above. Similarly stated, the battery isolation protrusion aperture 1721 of the safety lock 1700 is aligned with the system activation opening 1124 of the housing 1100, such that the battery isolation protrusion 1185 can be disposed within the housing 1100 when the cover 1180 is disposed about a portion of the housing 1100.

Figure 53:
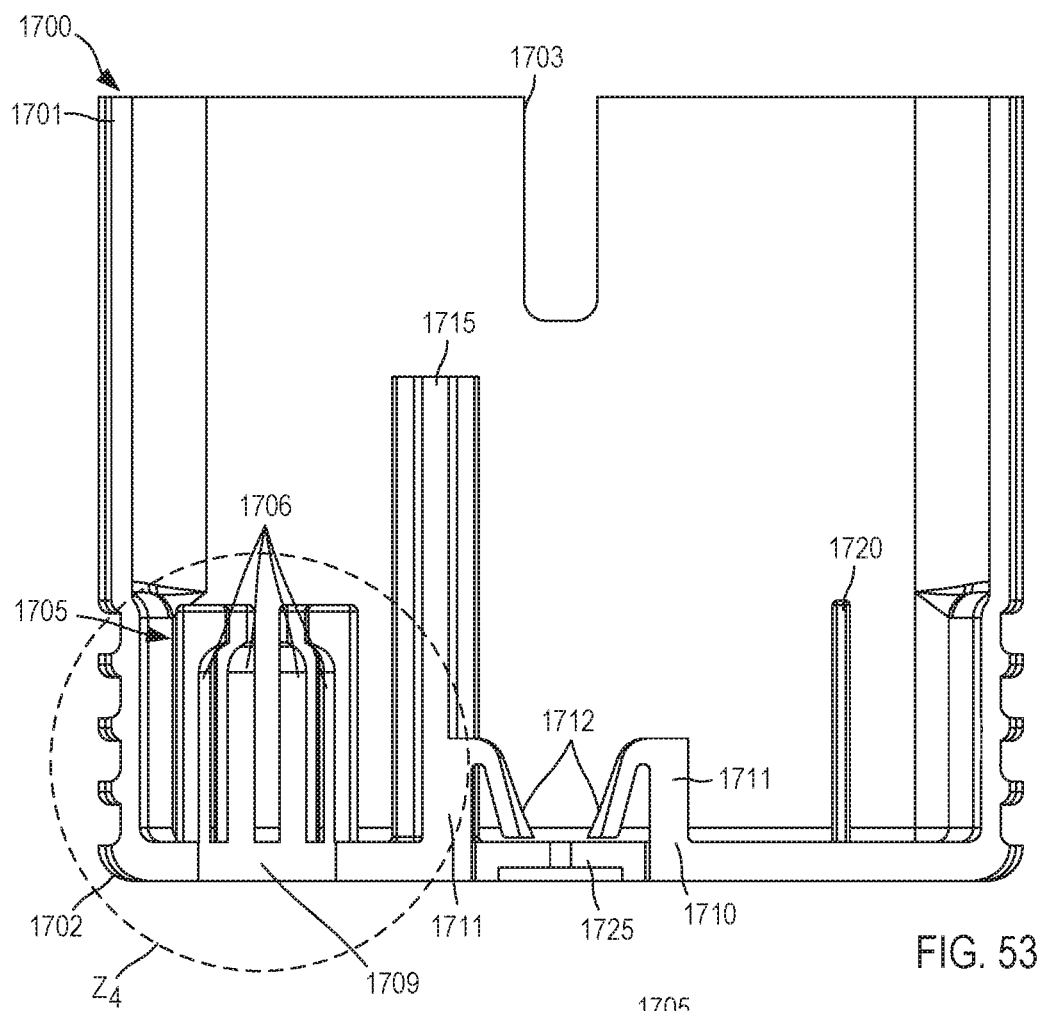
FIG. 53 is a cross-sectional view of the safety lock of FIG. 51 taken along the line $X_9$-$X_9$ in FIG. 52.
Figure 54:
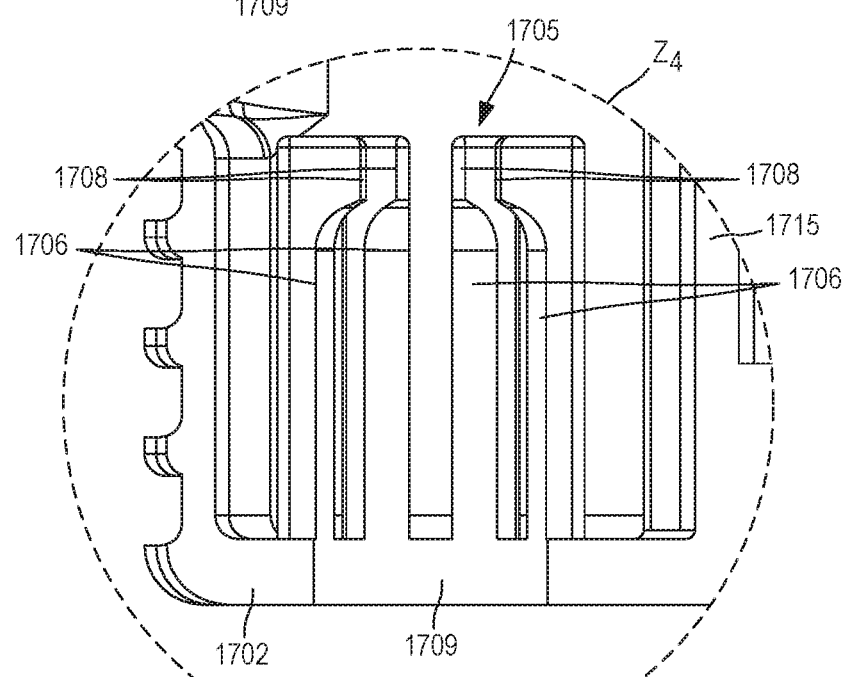
FIG. 54 is an enlarged view of a portion of the safety lock of FIG. 51 identified by the region $Z_4$ in FIG. 53.

The inner surface 1704 of the safety lock 1700 includes the lock portion 1705, the engagement portion 1710, the lock rod 1715, and the electronic activation protrusion 1720. The lock portion 1705 can be any suitable configuration. In this embodiment, the lock portion 1705 of the safety lock 1700 includes a set of lock arms 1706 each of which extend from the inner surface 1704 of the safety lock 1700. More specifically, the lock portion 1705 includes a set of eight lock arms 1706 that are each even spaced around a perimeter (in this embodiment, a circumference) of the lock portion opening 1709. In other words, the lock arms 1706 are in a symmetrically arrangement and collectively circumscribe the lock portion opening 1709. As shown in FIGS. 53 and 54, each lock arm 1706 includes a tab 1708 (e.g., a flange, protrusion, bend, curve, formation, etc.) disposed at a proximal end portion of the lock arm 1706.

Referring back to FIGS. 25 and 26, when the safety lock 1700 is coupled to the housing 1100 (e.g., in a first or locked position), the lock portion 1705 of the safety lock 1700 receives and/or otherwise engages the lock portion 1150 of the housing 1100. More particularly, the openings 1153 defined by the lock portion 1150 of the housing 1100 (see e.g., FIGS. 18-21) receive a corresponding lock arm 1706 included in the lock portion 1705 of the safety lock 1700. In this manner, the lock portion 1150 of the housing 1100, the distal end portion 1292 of the mixing actuator rod 1290, and the lock portion 1705 of the safety lock 1700 collectively define a interlocked arrangement, which can, for example, substantially enclose or surround a volume (see e.g., FIGS. 25, 26, and 56) configured to receive the lock member 1730. Specifically, in this embodiment, the lock member 1730 is a ball, bearing, or the like, and is disposed in the collectively formed volume. The arrangement of the lock portion 1150 of the housing 1100, the lock portion 1705 of the safety lock 1700, and at least the distal surface 1294 of the mixing actuator rod 1290 is such that the lock member 1730 selectively locks and/or maintains the safety lock 1700 in a fixed position relative to the housing 1100 when the medical injector 1000 is in a first orientation. Specifically, the position of the lock member 1730 maintains the safety lock 1700 in a fixed position relative to the housing 1100 when an angle formed between the distal end portion 1242 of the needle 1240 and the upward vertical axis (the "tilt angle") is greater than about ±25 degrees, about ±30 degrees, about ±35 degrees, about ±45 degrees, or about ±60 degrees. When the medical injector 1000 is in a first orientation, the lock member 1730 is disposed in the basket 1152 defined by the lock portion 1150 of the housing 1100 (e.g., in a first position). In this position, the lock member 1730 substantially prevents the tab 1708 of at least some of the lock arms 1706 from being moved from a proximal position relative to the lock member 1730. In other words, the lock member 1730 substantially prevents the safety lock 1700 from being removed from the housing 1100.

Conversely, when the medical injector 1000 is placed in a second orientation (e.g., oriented such that the tilt angle is less than about ±25 degrees, about ±30 degrees, about ±35 degrees, about ±45 degrees, or about ±60 degrees), the lock member 1730 can be disposed on or adjacent to the distal surface 1294 of the mixing actuator rod 1290 (e.g., in a second position). In this position, the lock member 1730 is aligned with an opening that is substantially circumscribed by the tabs 1708 of the lock arms 1706. In other words, the lock member 1730 is in a position that allows the tabs 1708 of the lock arms 1706 to be moved in the distal direction relative to the lock member 1730. Thus, when the lock member 1730 is in the second position (i.e., when the medical injector 1000 is in a second orientation), the safety lock 1700 can be removed from the housing 1100, as described in further detail herein.

The lock rod 1715 extends from the inner surface 1704 of the safety lock 1700 and is disposed in the safety lock rod portion 1515 of the needle opening 1514 defined by the base 1510 and the lock rod opening 1122 defined by the housing 1100 when the safety lock 1700 is coupled to the housing 1100. In this manner, a portion of the lock rod 1715 is disposed in the housing 1100 when the safety lock 1700 is coupled to the housing 1100. Moreover, as described above, a portion of the lock rod 1715 is in contact with the lock portion 1275 of the carrier 1260 and/or otherwise disposed between the first member 1276 and second member 1278 of the lock portion 1275 (see e.g., FIGS. 43 and 56). Accordingly, the lock rod 1715 is configured to maintain at least a portion of the tabs 1277 and 1279 of the first member 1276 and second member 1278, respectively, in the corresponding lock aperture 1113 defined by the housing 1100. Therefore, when the safety lock 1700 is coupled to the housing 1100, the lock rod 1715 can engage the carrier 1260 to limit and/or substantially prevent proximal movement of the carrier 1260 within the medicament cavity 1141 of the housing 1100. Accordingly, when the safety lock 1700 is coupled to the housing 1100, the mixing operation (which results from proximal movement of the carrier 1260) cannot be commenced.

The electronic activation protrusion 1720 extends from the inner surface 1704 of the safety lock 1700. As described above, the electronic activation protrusion 1720 is at least partially disposed in the battery isolation protrusion opening 1516 defined by the base 1510 and the system activation opening 1124 defined by the housing 1100 to engage a portion of the electronic circuit system 1900. Specifically, a portion of the electronic activation protrusion 1720 is disposed in the notch 1922 defined by the printed circuit board 1920 and in contact and/or engagement with the first switch 1925 when the safety lock is coupled to the housing 1100, as described above.

Figure 52:
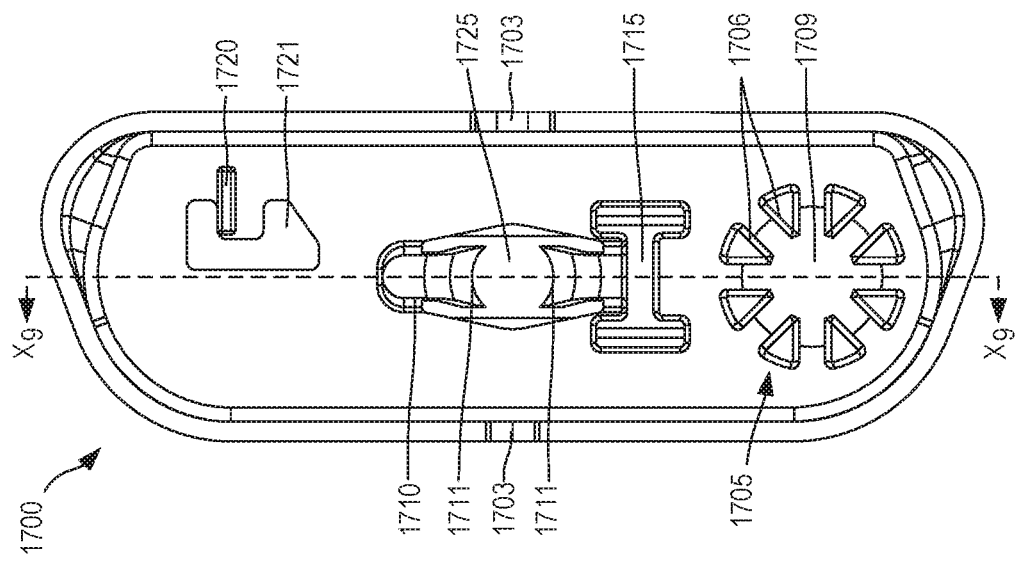
FIGS. 51 and 52 are a perspective view and a top view, respectively, of a safety lock included in the medicament delivery device of FIG. 11.
Figure 51:
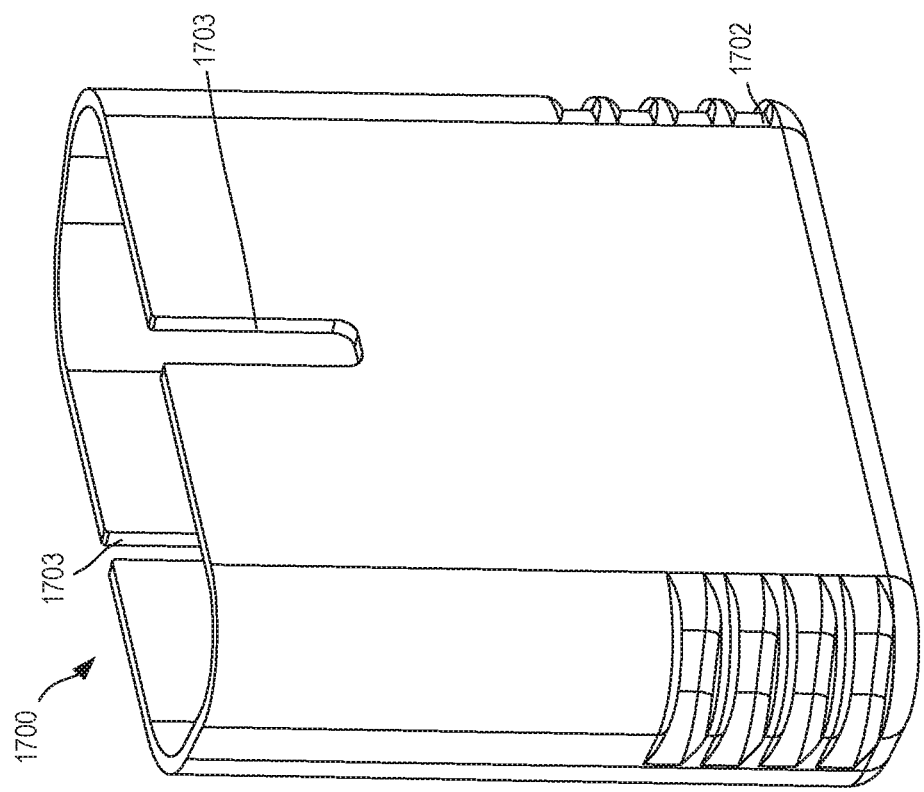

The engagement portion 1710 of the safety lock 1700 includes engagement members 1711. As shown in FIG. 52, in this embodiment, the engagement portion 1710 includes a pair of engagement members 1711 disposed on opposite sides of the needle sheath aperture 1725 and extending in a proximal direction from the inner surface 1704. The engagement members 1711 each have a tab 1712 that extends from a surface of the corresponding engagement member 1711. The tabs 1712 are configured to engage the rib 1285 disposed at a distal end portion 1282 of the needle sheath 1280 (see, e.g., FIG. 39, which shows the rib 1285). In this manner, distal movement of the safety tab 1700 results in a corresponding distal movement (e.g., removal of) the needle sheath 1280, as described in further detail herein.

Figure 55:
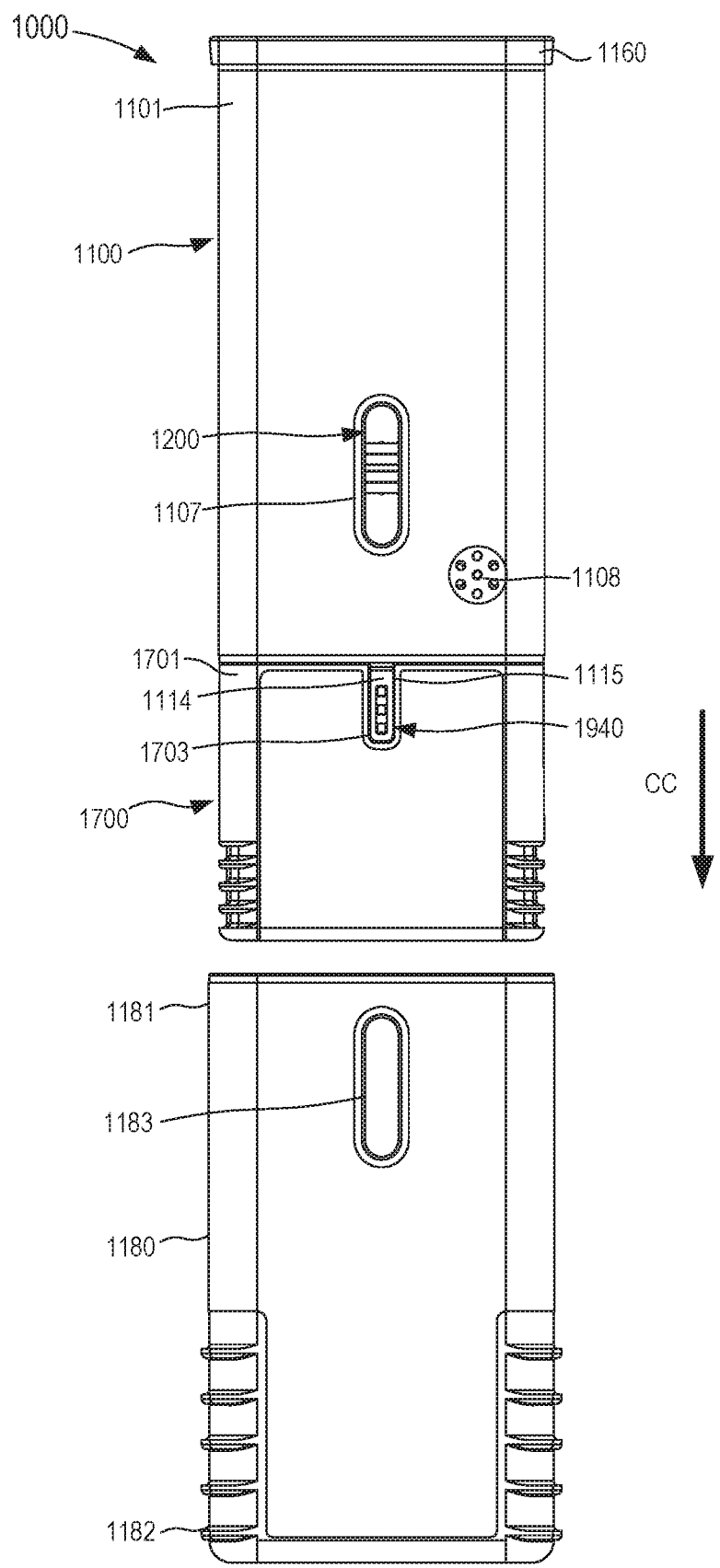
FIG. 55 is a front view of the medicament delivery device of FIG. 11 in the second configuration (i.e., with the case removed and the safety lock in the "locked" position).
Figure 56:
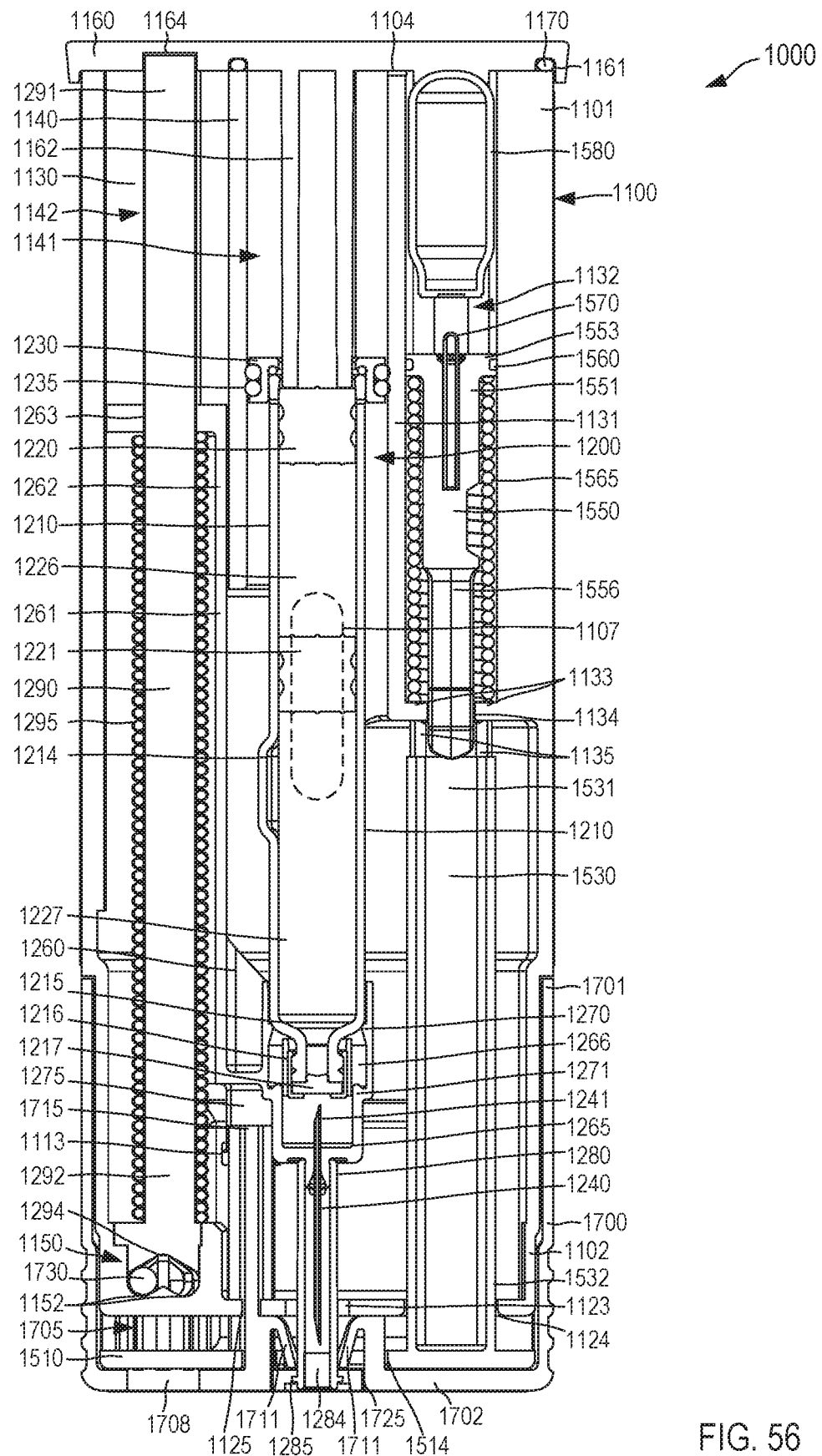
FIG. 56 is a cross-sectional view of the medicament delivery device of FIG. 11 in the second configuration, taken along the line $X_1$-$X_1$ in FIG. 15.

FIGS. 55-65 illustrate the medical injector 1000 in use. As shown in FIGS. 55 and 56, the medical injector 1000 is first enabled by removing the cover 1180 from the housing 1100, thereby transitioning the medical injector 1000 from the first (or initial) configuration to the second configuration, as indicated by the arrow CC in FIG. 55. When the cover 1180 is moved in the distal direction (e.g., in the direction of the arrow CC) with respect to the housing 1100, the battery isolation protrusion 1185 is removed from the area between contact portion 1913 of the battery clip 1910 and the second surface of the battery assembly 1935. In this manner, the battery assembly 1935 is operatively coupled to the electronic circuit system 1900 when the cover 1180 is removed, thereby providing power to the electronic circuit system 1900. Similarly stated, the electronic circuit system 1900 is actuated when the cover 1180 is removed.

When power is provided, as described above, the electronic circuit system 1900 can output one or more predetermined electronic outputs. For example, in some embodiments, the electronic circuit system 1900 can output an electronic signal associated with recorded speech to the audio output device 1930. Such an electronic signal can be, for example, associated with a .WAV file that contains a recorded instruction, instructing the user in the operation of the medical injector 1000. Such an instruction can state, for example, "Remove the safety tab near the base of the auto-injector to initiate mixing." The electronic circuit system 1900 can simultaneously output an electronic signal to one or more of the LEDs 1940, thereby causing one or more of the LEDs 1940 to flash a particular color. In this manner, the electronic circuit system 1900 can provide both audible and visual instructions to assist the user in the initial operation of the medical injector 1000.

In other embodiments, the electronic circuit system 1900 can output an electronic output associated with a description and/or status of the medical injector 1000 and/or the medicament contained therein. For example, in some embodiments, the electronic circuit system 1900 can output an audible message indicating the symptoms for which the medicament should be administered, the expiration date of the medicament, the dosage of the medicament or the like.

In yet other embodiments, the electronic circuit system 1900 can output a wireless signal to a cell phone, computer, compliance tracking device, emergency dispatch system, and/or the like. For example, in some embodiments, the electronic circuit system 1900 can output an wireless signal to a compliance tracking device, which receives the signal and monitors the activity (e.g., the arming of, the use of or the like) of the medical injector 1000.

In some embodiments, the medical injector 1000 can be repeatedly moved between the first configuration and the second configuration when the cover 1180 is moved repeatedly between the first position and the second position, respectively. Said another way, in some embodiments, the cover 1180 can be removed and replaced about the housing 1100 any number of times. When the cover 1180 is moved from the second position to the first position, the battery isolation protrusion 1185 is reinserted between the contact portion 1913 of the battery clip 1910 and the second surface of the battery assembly 1935, deactivating the electronic circuit system 1900. When the cover 1180 is moved from the first position to the second position a second time, the electronic circuit system 1900 is once again activated. In other embodiments, the cover 1180 is configured to be removed from the housing 1100 only one time and the electronic circuit system 1900 is therefore configured output a single electronic output in response thereto. In some such embodiments, the cover 1180 can be configured to remove the needle sheath 1280 and the electronic circuit system 1900 can warn the user about the compromised sterility of the needle 1240.

After the cover 1180 is removed from the housing 1100, the medical injector 1000 is in the second configuration. As shown in FIG. 56, the medical injector 1000 is in a locked or pre-actuated position while in the second configuration. Thus, the lock rod 1715 of the safety lock 1700 is disposed between the first member 1276 and the second member 1278 of the lock portion 1275 of the carrier 1260. As such, the tab 1277 of the first member 1276 and the tab 1279 of the second member 1278 are each maintained in a corresponding carrier lock aperture 1113 defined by the housing 1100. With the safety lock 1700 coupled to the housing 1100 and/or the base 1510, the carrier 1260 is maintained, for example, in a distal position within the medicament cavity 1241. More specifically, the lock rod 1715 exerts a lateral force on the first member 1276 and the second member 1278, thereby maintaining at least a portion of the tabs 1277 and 1279 within the corresponding carrier lock aperture 1113. In this manner, the tabs 1277 and 1279 can contact a surface of the housing 1100 defining a proximal portion of the corresponding carrier lock aperture 1113, which in turn, can exert a reaction force sufficient to maintain the bias member 1295 in its first configuration (e.g., a compressed or high potential energy configuration). Therefore, the medicament container assembly 1200 remains in a first configuration (e.g., a pre-mixed configuration). In this configuration, the diluent volume 1226 is separated and/or fluidically isolated from the dry medicament volume 1227. The proximal end portion 1241 of the needle 1240 is disposed distal to the seal member 1217 of the medicament container 1210 and is therefore substantially isolated from the medicament. Furthermore, the distal end portion 1242 of the needle 1240 is disposed within the needle sheath 1280 such that a user is protected from a sharp point defined by the distal end 1242 of the needle 1240, and the sterility of the needle 1240 is maintained.

Figure 57:
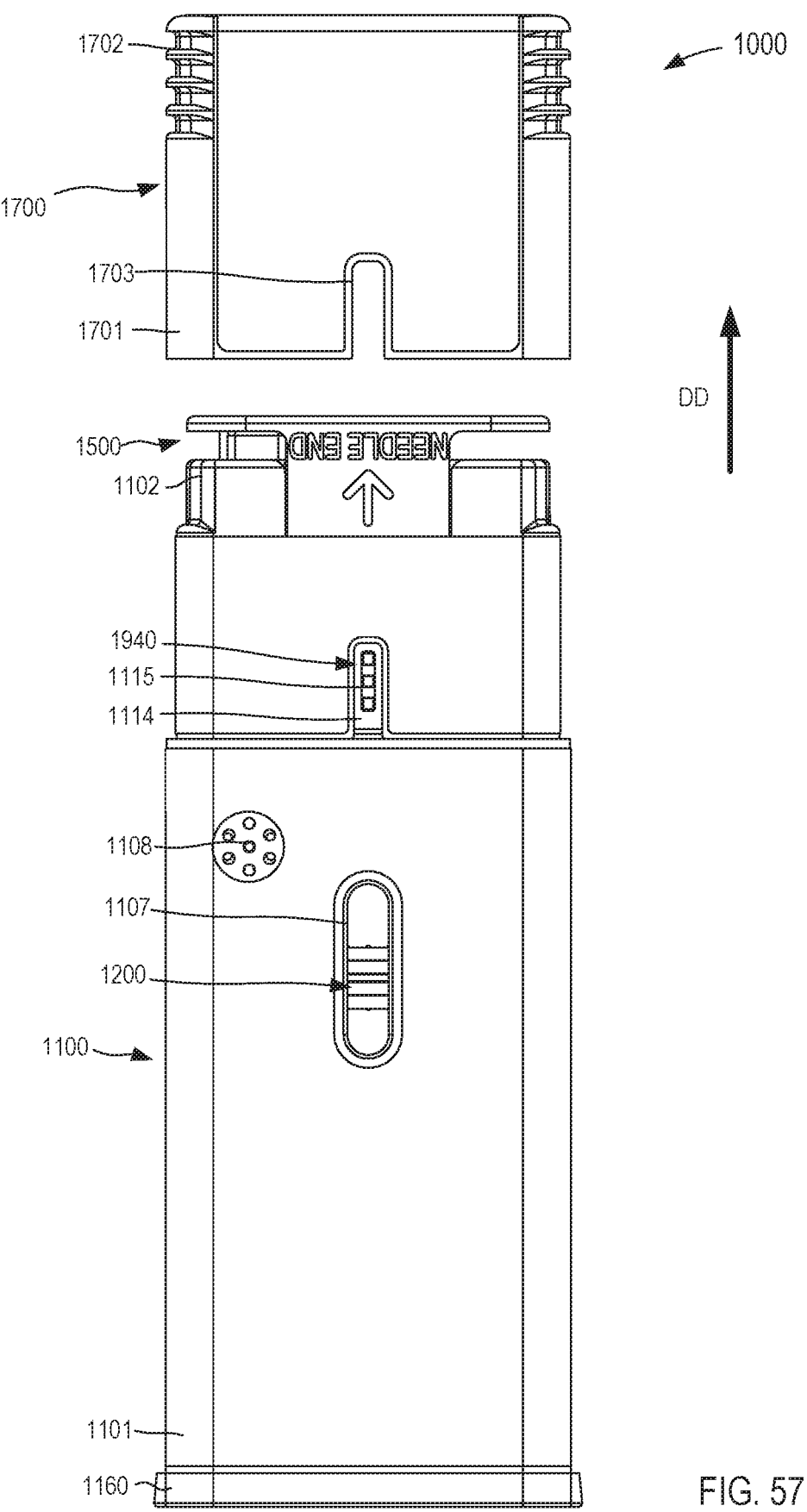
FIG. 57 is a front view of the medicament delivery device of FIG. 11 in the third configuration (i.e., with the safety lock removed to initiate mixing).
Figure 58:
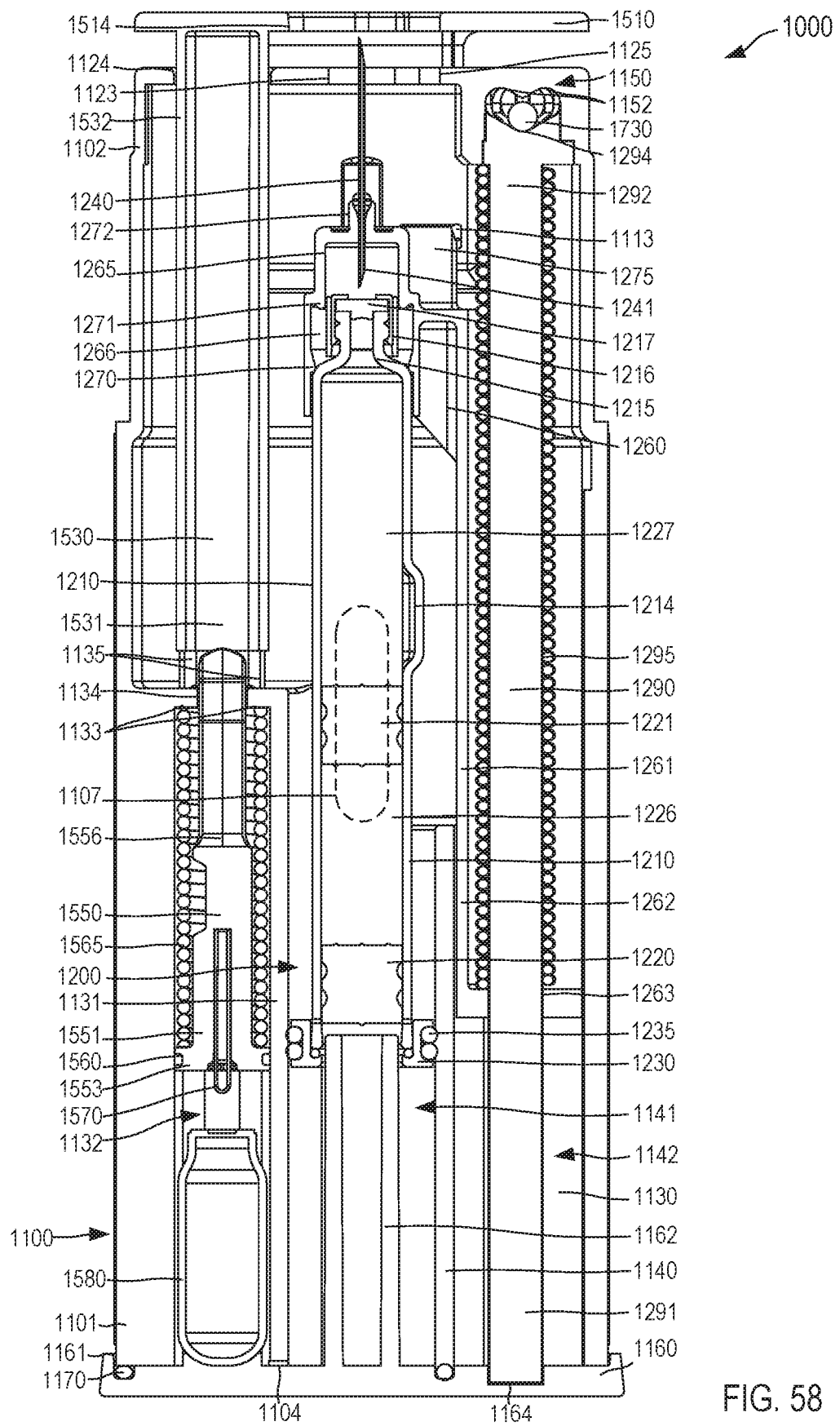
FIG. 58 is a cross-sectional view of the medicament delivery device of FIG. 1 in the third configuration, taken along the line $X_1$-$X_1$ in FIG. 15.

Moreover, as shown in FIG. 56, the medical injector 1000 is oriented such that the longitudinal axis of the needle 1240 is aligned with and/or parallel to a vertical axis, but with the distal end portion 1242 pointed downward. Thus, a tilt angle formed between the distal end portion 1242 of the needle 1240 and the upward vertical axis is 180 degrees. The arrangement of the lock portion 1150 of the housing 1100 and the lock portion 1705 of the safety lock 1700 causes the lock member 1730 to move within the basket 1152 and into engagement with the lock arms 1706 (see FIGS. 2 and 56). In this manner, when the medical injector 1000 is in the second configuration, the safety lock (or mixing actuator) 1700 cannot be moved relative to the housing 1100. Although the medical injector 1000 is shown and described as being in the second configuration when the tilt angle is 180 degrees, in other embodiments, the medical injector 1000 can be maintained in the second configuration when the tilt angle is between about 90 degrees and about 270 degrees (i.e., is greater than about ±90 degrees), between about 75 degrees and about 285 degrees (i.e., is greater than about ±75 degrees), between about 60 degrees and about 300 degrees (i.e., is greater than about ±60 degrees), between about 45 degrees and about 315 degrees (i.e., is greater than about ±45 degrees), between about 35 degrees and about 325 degrees (i.e., is greater than about ±35 degrees), between about 30 degrees and about 330 degrees (i.e., is greater than about ±30 degrees), and between about 25 degrees and about 335 degrees (i.e., is greater than about ±25 degrees), between about 20 degrees and about 340 degrees (i.e., is greater than about ±20 degrees), between about 15 degrees and about 345 degrees (i.e., is greater than about ±15 degrees), between about 10 degrees and about 350 degrees (i.e., is greater than about ±10 degrees), and between about 5 degrees and about 355 degrees (i.e., is greater than about ±5 degrees). The medical injector 1000 can be moved from the second configuration to a third configuration by reorienting the medical injector 1000 from the first orientation, in which the base 1510 is substantially distal to the housing 1100 (e.g., FIGS. 45 and 46, or otherwise oriented such that the tilt angle is greater than a predetermined value) to a second orientation, in which the base 1510 is substantially proximal to the housing 1100 (e.g., with the needle pointed "upwards" as shown in FIGS. 57 and 58, or otherwise oriented such that the tilt angle is less than a predetermined value). Similarly stated, the medical injector 1000 can be moved from the second configuration to a third configuration by first reorienting the medical injector 1000 to a second orientation in which the tilt angle is within (or less than) any of the ranges set forth herein, such as, for example, less than about 30 degrees from the upward vertical orientation (i.e., between about 330 and 30 degrees, or said another way, within about 30 degrees of the vertical axis in an upward direction).

With the medical injector 1000 in the second orientation, the medical injector 1000 can be manipulated by removing the safety lock 1700 from the housing 1100, as indicated by the arrow DD in FIG. 57. More specifically, as described above, prior to actuation of the medical injector 1000 and when the medical injector 1000 is in the first orientation, the lock member 1730 is disposed in the basket 1152 defined by the lock portion 1150 of the housing 1100. Thus, the lock member 1730 substantially prevents the removal of the safety lock 1700. As shown in FIG. 58, when the medical injector 1000 is moved to its second orientation, the lock member 1730 moves (e.g., under the force of gravity) to a position adjacent to and/or otherwise in contact with the tapered distal surface 1294 of the mixing actuator rod 1290. Thus, as described in detail above, the safety lock 1700 can be moved in the direction of the arrow DD in FIG. 57 to move the lock arms 1706 of the lock portion 1705 of the safety lock 1700 past the lock member 1730 (e.g., the movement of the safety lock 1700 passes the lock member 1730 through an opening (not shown) substantially circumscribed by the tabs 1708 of the lock arms 1706. As such, the safety lock 1700 can be removed from the housing 1100.

When the safety lock 1700 is moved from its first position to its second position (i.e., removed from the housing 1100), the electronic activation protrusion 1720 is likewise moved relative to the housing 1100. More specifically, the safety lock 1700 removes the electronic activation protrusion 1720 from the notch 1922 defined by the printed circuit board 1920 and out of contact and/or engagement with the first switch 1925 when moved to its second position. As such, the first switch 1925 can transition from a first state to a second state (e.g., closes an electric circuit or the like). The transition of the first switch 1925 to its second state can, for example, result in the electronic circuit system 1900 outputting one or more predetermined electronic outputs. For example, a processor (not shown) can output an electronic signal associated with recorded speech to the audio output device 1930. Such an electronic signal can be, for example, associated with a recorded message notifying the user of the status of the medical injector 1000. Such a status message can state, for example, "The needle guard has been removed and the mixing operation is in process," or "mixing complete." The electronic circuit system 1900 can also simultaneously output an electronic signal to one or more of the LEDs 1940, thereby causing one or more LEDs 1940 to start flashing, stop flashing, change color, and/or the like. In some embodiments, the housing can include a display such as a liquid crystal display (LCD), a light emitting diode (LED) display, and/or similar display that can graphically represent a visual status of the medical injector 1000 and/or the medicament prior to, during, and/or after mixing.

In some embodiments, the first switch 1925 and the electronic activation protrusion 1720 can be configured such that the electronic activation protrusion 1720 moves a predetermined distance before the electronic activation protrusion 1720 is removed from engagement with the first switch 1925. For example, in some embodiments, the electronic activation protrusion 1720 can move approximately 0.62 inches before the electronic activation protrusion 1720 disengages the first switch 1925. In this manner, the safety lock 1700 can be moved slightly without transitioning the first switch 1925 of the electronic circuit system 1900 to the second state. Accordingly, this arrangement will permit the user to inadvertently and/or accidentally move the safety lock 1700 without actuating the electronic circuit system 1900.

In some embodiments, as described above, the electronic circuit system 1900 can produce a recorded speech output instructing the user to "shake the device for at least five seconds." When the electronic circuit system 1900 detects changes in acceleration due to rapid or "shaking" motion, the electronic circuit system 1900 can initiate a countdown timer. Moreover, when the electronic circuit system detects that shaking has stopped prior to the completion of the timer period, the voice prompt can pause or stop the countdown timer, and only resume when the shaking has resumed.

In some embodiments, the electronic circuit system 1900 can be configured to output the status message for a predetermined time, such as, for example, five seconds. After the predetermined time has elapsed, the electronic circuit system 1900 can output an audible message further instructing the user in the operation of the medical injector 1000. Such an instruction can state, for example, "The mixing operation is now complete. Place the base of the auto-injector against the patient's thigh. To complete the injection, press the base firmly against the patient's thigh." In some embodiments, the electronic circuit system 1900 can simultaneously output an electronic signal to one or more of the LEDs 1940, thereby causing one or more of the LEDs 1940 to flash a particular color. In this manner, the electronic circuit system 1900 can provide both audible and/or visual instructions to assist the user in the placement and actuation of the medical injector 1000. In some embodiments, the electronic circuit system 1900 can be configured to repeat the instructions after a predetermined time has elapsed. In other embodiments, the output associated with the completion of the mixing operation (or any other operations described herein) need not be based on an elapsed time. For example, as described above, some such embodiments, the electronic circuit system 1900 can produce an output when the mixing event has ended based at least in part upon the location of a plunger within the medicament container.

In some embodiments, the medical injector 1000 can have a network interface device (not shown) configured to operatively connect the electronic circuit system 1900 to a remote device (not shown) and/or a communications network (not shown), as described above. In this manner, the electronic circuit system 1900 can send a wireless signal notifying a remote device that the safety lock 1700 of the medical injector 1000 has been removed and that the medical injector 1000 has been armed. In other embodiments, the electronic circuit system 1900 can send a wireless signal (e.g., a wireless 911 call) notifying an emergency responder that the medical injector 1000 has been armed. In yet other embodiments, the wireless signal can be sent after medicament delivery is detected by an audible signal, a mechanical switch, and/or other electronic sensor that provides status indication and subsequent signal detection during medicament delivery.

In addition to activating the electronic circuit system 1900, removal of the safety lock 1700 also initiates the mixing operation. Specifically, the movement of the safety lock 1700 from the first position to the second position moves the lock rod 1715 relative to the housing 1100. More specifically, the movement of the safety lock 1700 removes the lock rod 1715 from contact with the lock portion 1275 of the carrier 1260, thereby enabling movement of the medicament container assembly 1200. As described above, when the safety lock 1700 is coupled to the housing 1100, a portion of the lock rod 1715 is disposed in a space defined between the first member 1276 and the second member 1278 of the lock portion 1275 of the carrier 1260. Thus, the lock rod 1715 maintains the tab 1277 of the first member 1276 and the tab 1279 of the second member 1278 in its corresponding carrier lock aperture 1113 defined by the housing 1100. With the safety lock 1700 removed from the housing 1100, however, the lateral force exerted by the lock rod 1715 that maintains the carrier 1260 in its first position is removed. As such, the force exerted by the bias member 1295 is sufficient to overcome a friction force between the tabs 1277 and 1279 and their corresponding surface of the housing 1100 (as described above) and/or is otherwise sufficient to deform the lock portion 1275 such that the tabs 1277 and 1279 are removed from the carrier lock apertures 1113. As a result, the force exerted by the bias member 1295 on the flange 1262 of the mixing portion 1261 of the carrier 1260, moves the carrier 1260 in the direction of the arrow EE in FIG. 5.

Figure 59:
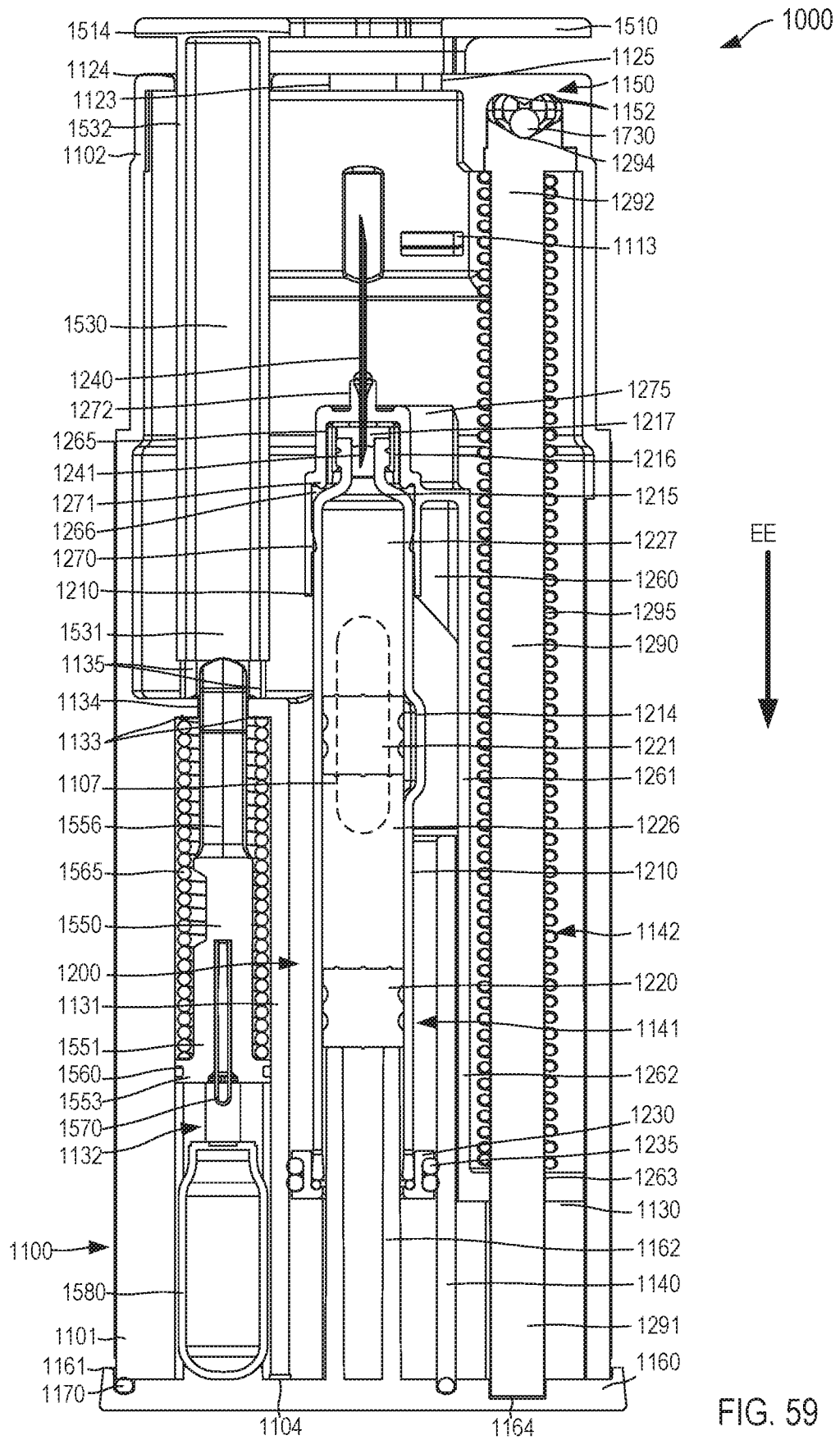
FIG. 59 is a cross-sectional view of the medicament delivery device of FIG. 11 in the fourth configuration (i.e., at the beginning of the mixing operation, with the needle in fluid communication with the medicament container), taken along the line $X_1$-$X_1$ in FIG. 15.
Figure 60:
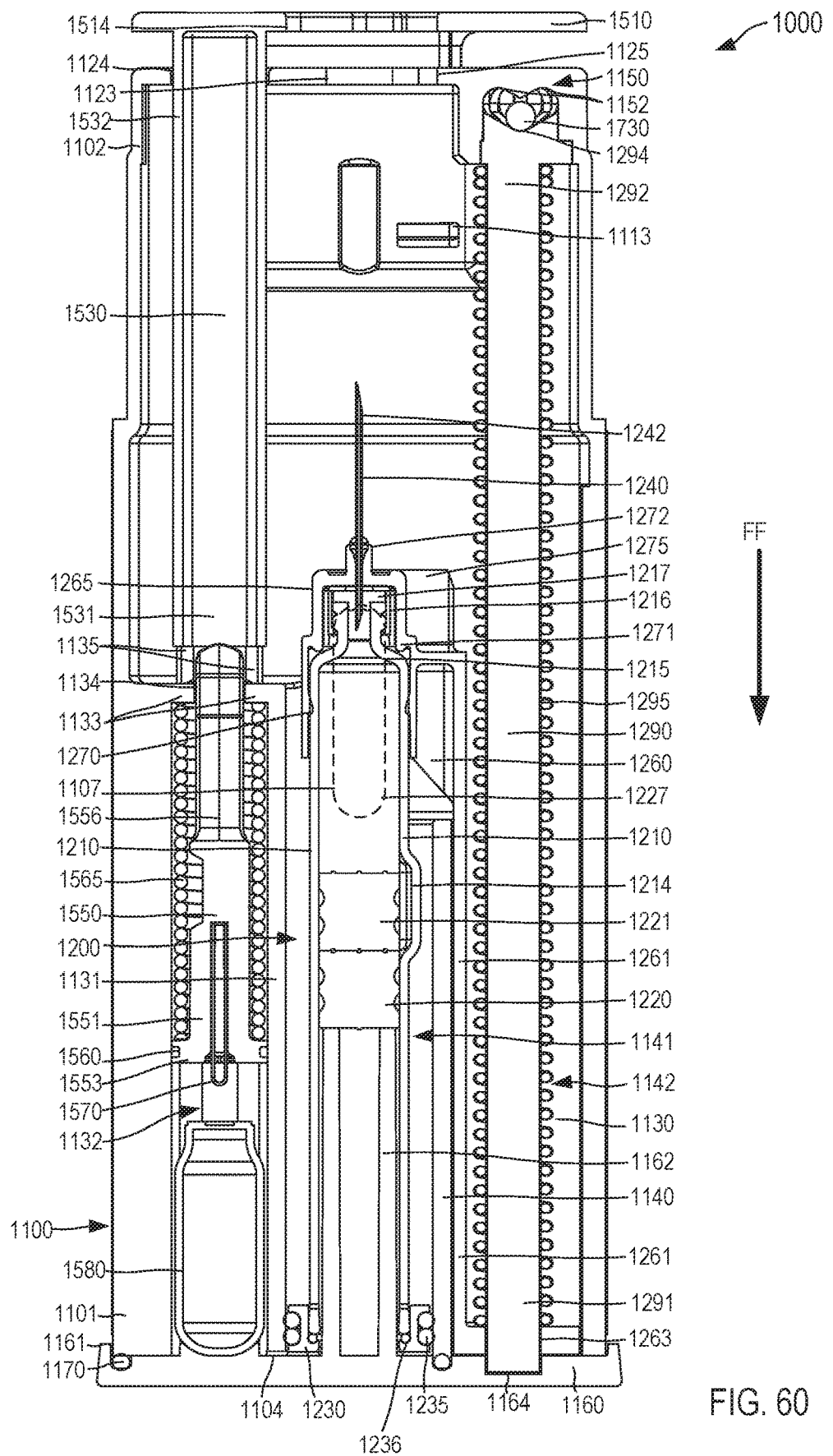
FIG. 60 is a cross-sectional view of the medicament delivery device of FIG. 11 in the fifth configuration (i.e., at completion of the mixing operation), taken along the line $X_1$-$X_1$ in FIG. 15.

As shown in FIGS. 58-60, the bias member 1925 moves the carrier 1260 in the proximal direction as indicated by the arrow EE in FIG. 59 and the arrow FF in FIG. 60. The proximal movement of the carrier 1260 similarly moves the medicament container 1210 in the proximal direction. More specifically, as shown in FIGS. 56 and 58, the medicament container 1210 is disposed within the housing 1100 such that the mixing protrusion 1162 of the proximal cap 1160 is adjacent to or in contact with the proximal or first elastomeric member 1220. Prior to the bias member 1295 being "released" (i.e., by disengagement of the tab 1277 and the tab 1279 from the housing 1100) to move the carrier 1260 in the proximal direction, the distal end portion 1212 of the medicament container 1210 is in contact with and/or otherwise engages the first shoulder 1270 of the container mounting portion 1265 of the carrier 1260. This is shown in FIG. 58, which shows the medical injector in its third configuration (i.e., just after removal of the safety lock 1700, but with the needle 1240 not yet in fluid communication with the medicament container 1210).

When carrier 1260 and/or the bias member 1295 is released, the force exerted by the bias member 1295 begins to move the carrier 1260 in the proximal direction. The arrangement of the medicament container 1210 is such that the carrier 1260 moves in the proximal direction relative to the medicament container 1210. Specifically, with the mixing protrusion 1162 of the proximal cap 1160 in contact with the first elastomeric member 1220, a force to move the carrier 1260 relative to the medicament container 1210 (e.g., a force to retract the first shoulder 1270 along a length of the medicament container 1210) eventually becomes less than a force needed to continue movement the first elastomeric member 1220 relative to the medicament container 1210. In other words, at this juncture in the mixing operation, the medicament container 1210 is temporarily maintained in a fixed position relative to the housing 1100 while the carrier 1260 moves in the proximal direction. Thus, as described below, during the initial stage of the mixing event, the medicament container 1210 moves relative to the carrier 1260 to place the needle 1240 in fluid communication with the medicament container 1210 (i.e., placing the medical injector 1000 into its fourth configuration, also referred to as the "priming" or "venting" configuration).

Specifically, after the carrier 1260 has moved a predetermined distance in the proximal direction and relative to the medicament container 1210 and after the elastomeric members 1220 and 1221 have moved within the medicament container 1210 (see e.g., FIG. 59), a portion of the medicament container 1210 is moved into contact with the second shoulder 1271 of the carrier 1260. Thus, as shown in FIG. 59, the distal cap 1216 of the medicament container 1210 is disposed in the volume defined by the second portion 1268 of the inner surface 1266 of the container mounting portion 1265. In addition, the proximal movement of the carrier 1260 relative to the medicament container 1210 concurrently moves the needle 1240 relative to the medicament container 1210 such that the proximal end portion 1241 of the needle 1240 pierces the seal member 1217 of the medicament container 1210 and thus, is placed in communication with the dry medicament volume 1227. With the needle 1240 in communication with the dry medicament volume 1227 of the medicament container 1210 (i.e., with the medicament container 1210 being disposed in a second position relative to the carrier 1260), trapped gas within the medicament container 1210 can be vented. Thus, after the safety lock 1700 is removed, the medical injector 1000 is moved from its third configuration (FIG. 58) to its fourth configuration (FIG. 59, i.e., at the beginning of mixing with the needle 1240 in fluid communication with the medicament container 1210 to facilitate venting or priming).

Expanding further, the constituents in the diluent volume 1226 can be, for example, an incompressible fluid or the like while the constituents of the dry medicament volume 1227 can include a substantially incompressible solid (which can include some amount of a compressible gas). As such, the diluent volume 1226 can at least temporarily remain constant in size during the mixing operation and thus, the medicament container 1210 can similarly move relative to the second elastomeric member 1221. Similarly stated, as shown in FIGS. 58 and 59, the first elastomeric member 1220 and the second elastomeric member 1221 can initially move together as the injector 1000 moves from its third configuration to its fourth configuration. The movement of the first elastomeric member 1220 and the second elastomeric member 1221 (see FIGS. 58 and 59) can compress and/or otherwise decrease the size of the dry medicament volume 1227 without expelling the dry and/or lyophilized medicament contained therein. When the medical injector 1000 reaches the fourth (or venting) configuration, a portion of a gas within the dry medicament volume 1227 is expelled or vented therefrom via the needle 1240.

As the medical injector 1000 moves from the third configuration (FIG. 58) to the fourth configuration (FIG. 59), the medicament container 1210 and the carrier 1260 can move in the proximal direction to an extent that substantially aligns the bypass 1214 with the second elastomeric member 1221, as shown in FIGS. 59 and 60. In this embodiment, the bypass 1214 can extend along a length of the medicament container 1210 that is greater that a length along which each elastomeric member 1220 and 1221 extends. Thus, when the medicament container 1210 is moved in the proximal direction and the bypass 1214 is substantially aligned with the second elastomeric member 1221, the increased pressure within the diluent volume 1227 urges a flow of the fluid diluent through the bypass 1214 and around the second elastomeric member 1221 to be transferred into the dry medicament volume 1227. In this manner, the fluid diluent can mix with the lyophilized medicament disposed within the dry medicament volume 1227 to reconstitute the medicament for injection.

Further proximal movement of the carrier 1260 moves the medicament container 1210 in the proximal direction, as indicated by the arrow EE in FIG. 59 and the arrow FF in FIG. 60, thereby moving the medical injector 1000 from its fourth (or venting) configuration (FIG. 59) to its fifth configuration (FIG. 60, with mixing completed). More particularly, as shown in FIG. 60, when the medicament container 1210 is the second position relative to the carrier 1260, the carrier 1260 and the medicament container 1210 move concurrently relative to the housing 1100. With the mixing protrusion 1162 of the proximal cap 1160 being disposed in contact with the first elastomeric member 1220, the proximal movement of the carrier 1260 and medicament container 1210 is, for example, relative to the mixing protrusion 1162 and at least the first elastomeric member 1220. Thus, the proximal movement of the medicament container 1210 with the carrier 1260 completes the mixing event, as shown in FIGS. 59 and 60. The arrangement of the elastomeric members 1220 and 1221 within the medicament container 1210 is such that as the medicament container 1210 is moved in the proximal direction relative to the housing 1100, the elastomeric members 1220 and 1221 move within the medicament container 1210 (as shown in FIGS. 59 and 60).

Referring to FIG. 60, the medicament container 1210, the carrier 1260, and the second elastomeric member 1221 can collectively move in the proximal direction relative to the first elastomeric member 1220 until substantially all of the fluid diluent previously disposed in the diluent volume 1226 is transferred to the dry medicament volume 1227 (which now becomes a reconstituted medicament volume), thereby placing the medical injector 1000 in the fifth configuration (completion of mixing). Although the medical injector 1000 is shown and described as being configured to purge at least a portion of gas contained in the dry medicament volume 1227 via the needle 1240, in other instances, the mixing event can purge all or substantially all of the gas contained in the dry medicament volume 1227 and, once purged, can similarly purge a relatively small volume of the reconstituted medicament.

In addition to facilitating venting and mixing, the proximal movement of the medicament container 1210 and the carrier 1260 is such that a portion of the medicament container assembly 1200 visible via the status indicator apertures 1107 defined by the housing 1100 is changed. For example, as shown in FIGS. 56, 58, and 59, the second elastomeric member 1221 is viewable via the status indicator apertures 1107 when the medical injector 1000 is in the first, second, and third configuration. As shown in FIG. 60, however, the proximal movement of the medicament container 1210, the second elastomeric member 1221, and the carrier 1260 is such that the distal end portion 1212 of the medicament container 1210 is viewable via the status indicator aperture 1107 and the elastomeric members 1220 and 1221 are obstructed by the housing 1100 and/or otherwise not aligned with the status indicator apertures 1107. Thus, a user can visually inspect the medicament container assembly 1200 to determine if the diluent volume 1226 was properly mixed with the dry medicament volume 1227. Thus, the user is guided not only by the output from the electronic circuit system 1900, but also by the mechanical visual indicators.

Figure 61:
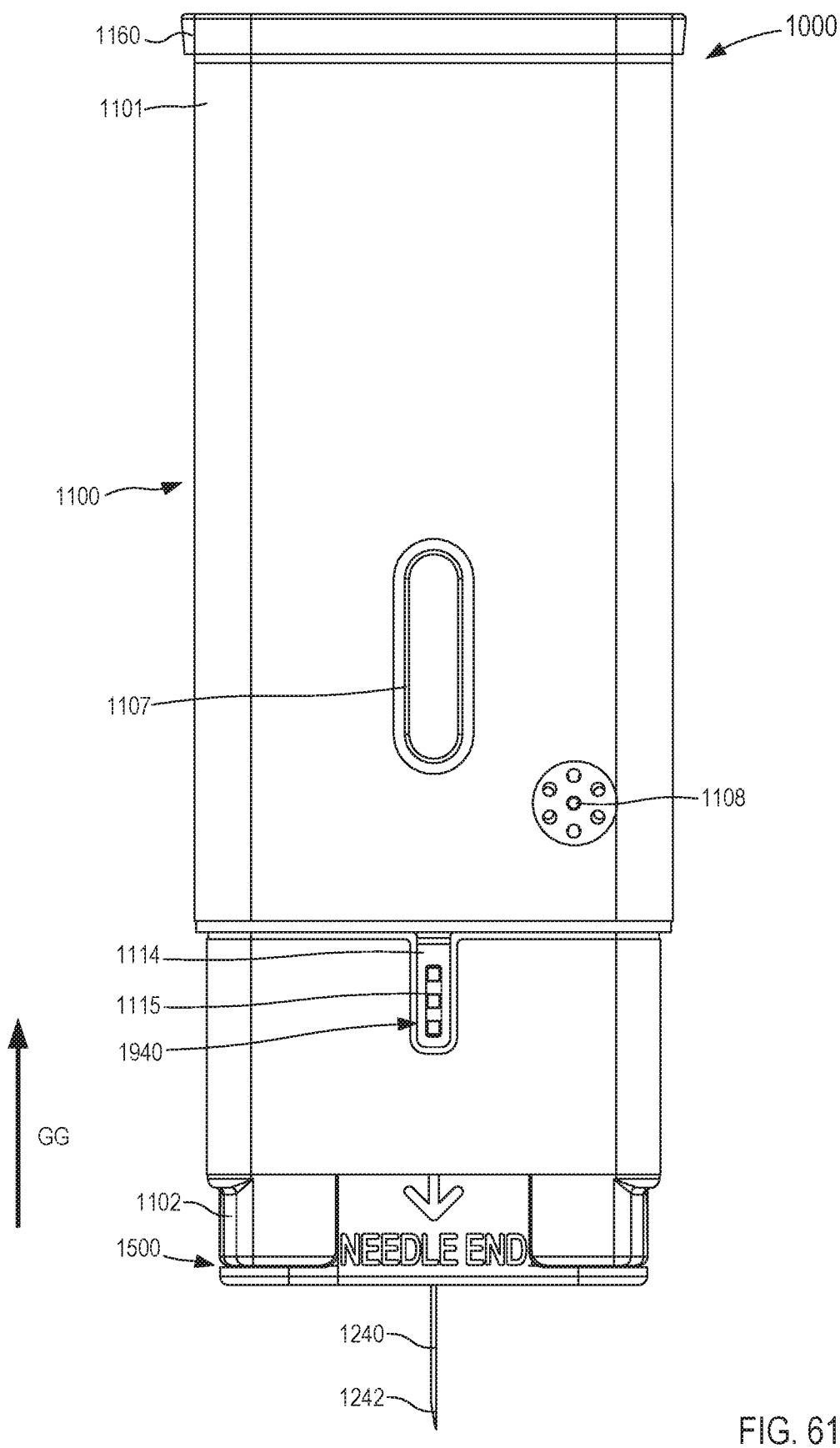
FIG. 61 is a front view of the medicament delivery device of FIG. 11 in the sixth configuration (i.e., after actuation of the base, with the needle insertion completed).
Figure 62:
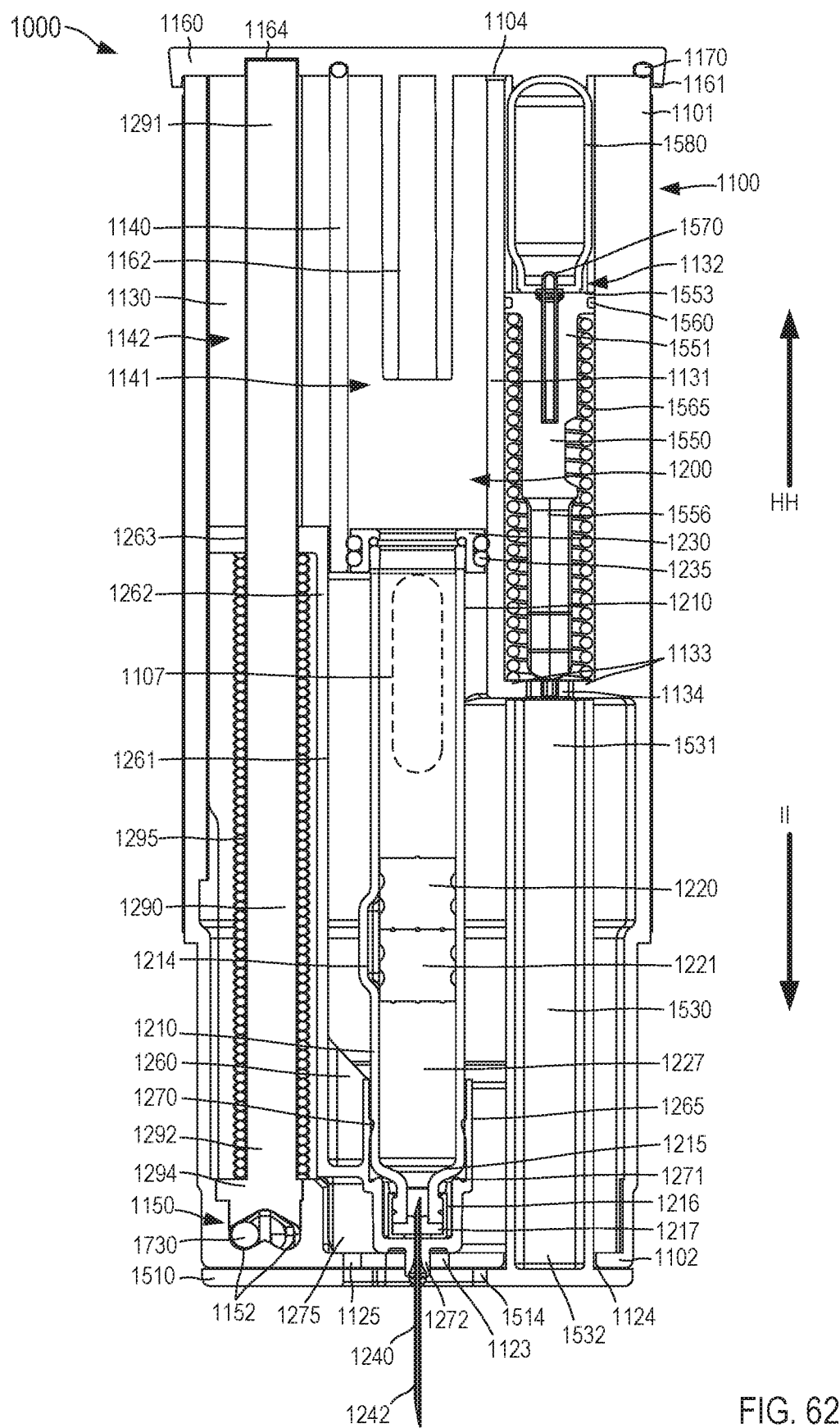
FIG. 62 is a cross-sectional view of the medicament delivery device of FIG. 11 in the sixth configuration, taken along the line $X_1$-$X_1$ in FIG. 15.

After the mixing event, the medical injector 1000 can be moved from the fifth configuration (FIG. 60) to a sixth configuration (i.e., the beginning of the injection event with the needle insertion operation complete, as shown in FIGS. 61 and 62). For example, as shown in FIG. 61, once the mixing event is complete, the medical injector 1000 can be manipulated to be placed in the first orientation (i.e., with the distal end 1242 of the needle 1240 pointed downward), as shown in FIG. 61. In some instances, the electronic circuit system 1900 can be configured to notify the user when the mixing event is completed. Moreover, in some embodiments, the orientation sensor and/or accelerometer can produce a signal associated with the orientation of the medical injector 1000 after completion of the mixing event. Thus, in some embodiments, the electronic circuit system 1900 can produce an output notifying the user of the orientation of the device (e.g. "To inject, turn the device upside down") and can repeat this output until the medical injector 1000 is placed in a correct orientation. In some embodiments, the mixing event can purge a small volume of reconstituted medicament, which can in turn, visually indicate that the mixing event is complete. In still other embodiments, the rate at which the mixing event occurs can be sufficiently fast to an extent that the mixing event is complete by the time the medical injector 1000 is placed in the fifth configuration.

As shown in FIGS. 61 and 62, once the medical injector 1000 is reoriented, the base 1510 is moved from a first position to a second position to place the medical injector 1000 in the fifth configuration. Similarly stated, the medical injector 1000 can be actuated by the system actuator assembly 1500 by moving the base 1510 proximally relative to the housing 1100. The base 1510 is moved from its first position to its second position by placing the medical injector 1000 against a target surface (e.g., the body of the patient) and moving the base 1510 with respect to the housing 1100 in the proximal direction, as indicated by the arrow GG in FIG. 61.

When the base 1510 is moved from the first position to the second position, the system actuator assembly 1500 actuates and/or otherwise releases the release member 1550 (as described below) and also moves the electronic activation protrusion 1520 relative to the housing 1100. More particularly, the electronic activation protrusion 1520 is moved in a proximal direction and into contact and/or engagement with the second switch 1926 of the electronic circuit system 1900. As such, the second switch 1926 can be transitioned from its first electric state to its second electric state. In some instances, the transition of the second switch 1926 to the second electric state can be operable in causing the electronic circuit system 1900 to perform one or more tasks such as outputting an audio output via the audio output device 1930 and/or a visual output via the one or more LEDs 1940, as described in detail above.

In addition to activating the second switch 1926, the proximal movement of the base 1510 from its first position to its second position actuates and/or otherwise releases the release member 1550. As such, the spring 1565 is allowed to transition from a first configuration (e.g., a compressed configuration) to a second configuration (e.g., a non-compressed configuration), thereby moving the release member 1550 within the gas cavity 1132. More specifically, the proximal movement of the base 1510 moves the release rod 1530 in the proximal direction within the housing 1100, thereby placing the engagement surface 1534 of the proximal end portion 1531 of the release rod 1530 in contact with the first extension 1554 and the second extension 1556 disposed at or near the distal end portion 1552 of the release member 1550. As such, the engagement surface 1534 engages the extensions 1554 and 1556 and as a result reduces a distance therebetween (e.g., reduces the opening 1558). More specifically, the engagement surface 1534 engages the first extension 1554 and the second extension 1556 to disengage and/or otherwise remove the projections 1555 and 1557, respectively, from the distal wall 1133 of the gas cavity 1132. With the projections 1555 and 1557 disengaged from the distal wall 1133, the force exerted by the spring 1565 can move the release member 1550 in the proximal direction such that the projections 1555 and 1557 pass through the opening 1134 defined by the distal wall 1133, as shown in FIG. 62. Similarly stated, when the base 1510 is moved in the proximal direction, the engagement surface 1534 disengages the release member 1550, thereby allowing the spring 1565 to transition from its first configuration to its second configuration, as indicated by the arrow HH in FIG. 62.

With the base 1510 placed in its second position and with the release member 1550 disengaged from the distal wall 1133, the spring 1565 moves the release member 1550 in the proximal direction to cause the puncturer 1570 to puncture and/or pierce a portion of the gas container 1580 (e.g., a frangible seal or the like). After the gas container 1580 has been punctured, an actuating portion of a compressed gas flows from the gas container 1580 and into the gas cavity 1132. Moreover, with the seal 1560 of the release member 1550 forming a substantially fluid tight seal with the inner surface 1130 defining the gas cavity 1132, the actuating portion of the compressed gas fills the gas cavity 1132 and is forced through the gas passageway 1104 defined by the housing 1100 and into the medicament cavity 1141.

Figure 63:
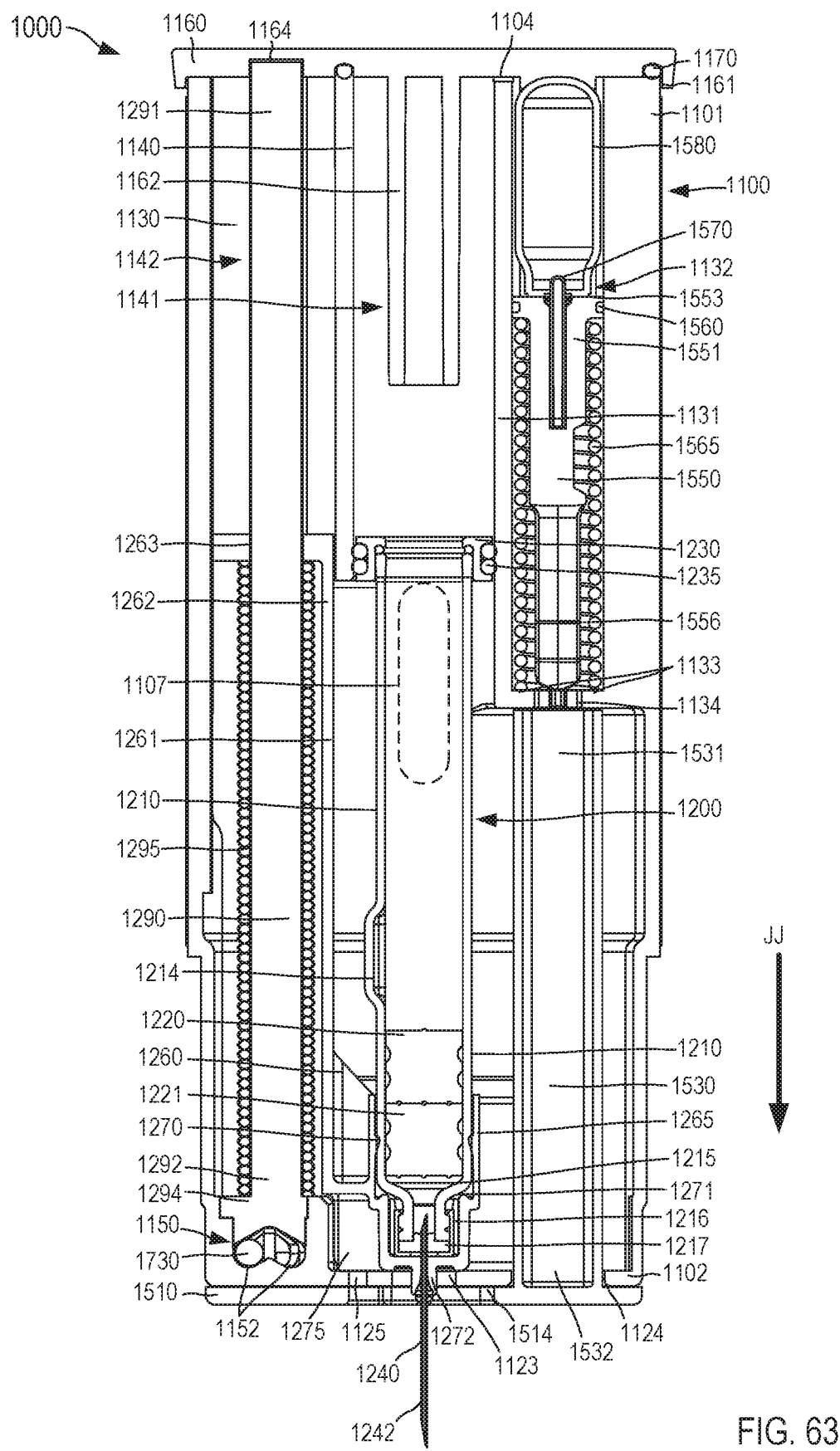
FIG. 63 is a cross-sectional view of the medicament delivery device of FIG. 11 in the seventh configuration (i.e., after completion of the injection operation), taken along the line $X_1$-$X_1$ in FIG. 15.

As the gas flows into the medicament cavity 1141, the gas applies gas pressure to the flange 1230 of the medicament container 1210 and the first elastomeric member 1220 within the medicament container 1210. More specifically, the seal member 1235 disposed about the flange 1230 coupled to the proximal end portion 1211 of the medicament container 1210 forms a substantially fluid tight seal with a portion of the inner surface 1130 defining the medicament cavity 1141. The seal member 1236 (i.e., the inner seal) forms a substantially fluid tight seal with an inner portion of the flange 1230 that defines at least a portion of the medicament cavity 1141. Thus, the pressure within the medicament cavity 1141 increases as a volume of the gas disposed in the medicament cavity 1141 increases. Once the pressure within the medicament cavity 1141 reaches an amount that provides enough force to overcome the static friction, that force on the flange 1230 moves the medicament container 1210 and the carrier 1260 in the distal direction, as indicated by the arrow II in FIG. 62. More particularly, the force exerted to move the medicament container 1210 (the insertion force) is a function of the pressure within the medicament cavity 1141 and the surface area of the flange 1230. The force exerted to produce injection (the injection force, which moves the elastomeric members within the medicament container 1210) is a function of the pressure within the medicament cavity 1141 and the surface area of the first elastomeric member 1220. Thus, the relative sizes of the flange 1230 and the first elastomeric member 1220 are selected such that the insertion force is sufficient to produce needle insertion (FIGS. 61 and 62) before the injection force reaches a threshold sufficient to produce delivery of the medicament (FIG. 63).

In some instances, the gas pressure within the medicament cavity 1141 can exert an insertion force sufficient to overcome a reaction force exerted by the bias member 1295 of the medicament container assembly 1200. In response to the insertion force, the medicament container 1210, the carrier 1240 and the needle 1240 contemporaneously move within the housing 1100 in the distal direction. The movement of the needle 1240 in a distal direction causes the distal end portion 1242 of the needle 1240 to exit the housing 1100 and enter the body of a patient prior to administering the medicament, thereby placing the medical injector 1000 in the sixth configuration. The insertion force associated with the gas pressure causes the carrier 1260 and the medicament container 1210 to move within the medicament cavity 1141 a predetermined distance (to facilitate needle insertion). In some embodiments, the predetermined distance can be associated with a position at which the carrier 1260 is in contact with the housing 1100, thereby completing the needle insertion operation. As such, further distal movement of the carrier 1260, the medicament container 1210 and/or the needle 1240 is substantially prevented.

With the medicament container 1210 in a distal position (the needle fully inserted), the gas within the medicament cavity 1141 continues to apply gas pressure to the medicament container 1210 including a proximal surface of the first elastomeric member 1220. Thus, when the gas pressure within the medicament cavity 1141 exceeds a given threshold, the gas pressure exerts an injection force on the first elastomeric member 1220 sufficient to move the first elastomeric member 1220 in the distal direction within the medicament container 1210. As shown in FIG. 62, the first elastomeric member 1220 can be in contact with the second elastomeric member 1221 such that the gas pressure exerts a force sufficient to move both the elastomeric members 1220 and 1221 in the distal direction. The distal movement of the elastomeric members 1220 and 1221 generates a pressure upon the medicament contained within the medicament container 1210, thereby allowing at least a portion of the medicament to flow out of the medicament container 1210 via the needle 1240, as indicated by the arrow JJ in FIG. 63. Furthermore, when the elastomeric members 1220 and 1221 are disposed in a distal position within the medicament container 1210, the medical injector 1000 has delivered a dose of the reconstituted medicament. As such, the medical injector 1000 is placed in the seventh configuration (FIG. 63). As shown, the injection (or delivery) operation is completed solely via the gas pressure exerting a force against the elastomeric members 1220 and 1221, without a physical piston or rod contacting the elastomeric members 1220 and 1221.

As shown in FIGS. 64 and 65, after the medical injector 1000 delivers the reconstituted medicament, the gas pressure within the medicament cavity 1141, the gas cavity 1132, and/or the gas container 1580 can substantially equalize or be reduced to facilitate needle retraction. Similarly stated, after medicament injection, the medical injector 1000 can be moved from the seventh configuration (FIG. 63) to an eighth configuration (needle retraction). In some embodiments, the distal movement of the medicament container assembly 1200 can be such that a volume of at least the medicament cavity 1141 is increased to an extent that the gas pressure therein is decreased below a predetermined threshold. After the gas pressure within the medicament cavity 1141 and/or gas cavity 1132 is equalized and/or otherwise falls below a predetermined threshold, the reaction force exerted by the bias member 1295 in response, for example, to being compressed under the gas pressure is sufficient to overcome a remaining force associated with the decreased gas pressure, thereby allowing the bias member 1295 to transition toward its biased (e.g., non-compressed) configuration. In this manner, the bias member 1295 exerts a force on the flange 1262 of the carrier 1260 to cause the carrier 1260 to move proximally within the housing 1100 (i.e., to retract). Thus, after the injection event, the distal end portion 1242 of the needle 1240 can be automatically retracted in the housing 1100, thereby placing the medical injector 1000 in the eighth configuration, as indicated by the arrow KK in FIG. 65. Moreover, it is noted that the bias member 1295 functions to produce a force at a first time to move the carrier 1260 proximally to produce mixing and produce a force at a second time to move the carrier 1260 proximally to retract the needle.

In some embodiments, the medical injector 1000 can include a gas release valve and/or the like configured to vent or release a portion of gas after the medical injector 1000 is placed in the seventh configuration. In some such embodiments, the gas release valve can be an "active" valve that is actuated only after the injection is completed (after the medical injector 1000 is placed in the seventh configuration). For example, in some embodiments, the medicament container 1210 can include valve or other structure (e.g., a vent that is gas permeable, but liquid impermeable) that is actuated or otherwise exposed when one of the first elastomeric member 1220 or the second elastomeric member 1221 moves beyond a particular position within the medicament container 1210 (e.g., the movement as shown in FIGS. 62 and 63). In other embodiments, the gas release valve can be a passive mechanism that is always opened. For example, in some embodiments, the flange 1230 includes a passageway or orifice (not shown) that permits a continuous "bleed" of air pressure from the medicament cavity 1141. In such embodiments, the passageway can be sized such that the release of gas pressure is at a low enough rate to ensure sufficient gas pressure to produce the desired insertion and injection force, while being at a high enough rate to facilitate retraction after completion of the injection. Although the passageway or orifice is described as being defined by the flange 1230, in other embodiments, a suitable portion of the medical injector 1000 can define such a passageway (e.g., the housing 1100, the proximal cap 1160, the release member 1550, and/or the like).

The retraction of the carrier 1260 results in a change in a portion of the medicament container assembly 1200 that is viewable via the status indicator apertures 1107. Thus, the user can visually inspect the medicament container assembly 1200 to determine if the injection event is complete. In addition, as described above, the protrusion 1520 of the base 1510 actuates the second switch 1925 of the electronic circuit system 1900 when the base 1510 is moved in the proximal direction. In some embodiments, the electronic circuit system 1900 can be configured to trigger a predetermined output or sequence of outputs when the medicament container assembly 1200 is moved its retracted position. For example, the electronic circuit system 1900 can output an audio message after a predetermined time following the activation of the second switch 1926. Such an audio message can state, for example, "The injection is now complete. Please seek further medical attention from a doctor." In other embodiments, a record speech output can include a "countdown" timer instruct the user on how long the user should maintain the injection device 1000 in contact with the target location. The electronic circuit system 1900 can also simultaneously output an electronic signal to one or more LEDs 1940, thereby causing one or more LEDs 1940 stop flashing, change color, and/or the like to provide a visual indication that the injection is complete. In other embodiments, the electronic circuit system 1900 can send a wireless signal notifying a remote device that the injection is complete. In this manner, a patient's compliance and/or adherence with the use of the system can be monitored.

Once the needle 1240 is retracted into the housing 1100 and the electronic circuit system 1900 has output a corresponding audio and/or visual output, the medical injector 1000 or at least a portion thereof can be disposed of. For example, in some embodiments, the medical injector 1000 is a single use device, which can be safely disposed of in its entirety after use. In other embodiments, only a portion of the medical injector 1000 is disposable. For example, after use, the medical injector 1000 can be manipulated to remove, for example, the medicament container 1210, the carrier 1260, and the substantially empty gas container 1580, which can then be replaced with an unused and sterilized medicament container and carrier including an unused needle sheath, and an unused gas container. In addition, the release member 1550 and the base 1510 of the system actuator assembly 1500 and the bias member 1295 of the medicament container assembly 1200 can be reset (e.g., placed in a pre-actuated configuration in which the bias member 1295 and the spring 1565 have a relatively high potential energy and/or are otherwise compressed or "loaded"). Once completed, the medical injector 1000 can be manipulated to replace and/or reposition the safety lock 1700 and the cover 1180. The arrangement of the electronic circuit system 1900 can be such that when, for example, the system actuator assembly 1500 is reset and the safety lock 1700 and case 1180 are replaced, the electronic circuit system 1900 is similarly reset. Specifically, since the first switch 1925 and the second switch 1926 are reversible switches, the resetting of the medical injector 1000 as described above, places both the first switch 1925 and the second switch 1926 in its respective first state. Thus, at least a portion of the medical injector 1000 can be reusable.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

For example, although the safety member 2700 is shown and described as having a lock protrusion 2706 and the safety member 3700 is shown and described as having a first portion 3715 that actuates an energy storage member, in some embodiments, a safety member can include a lock protrusion similar to the lock protrusion 2706 and an actuation portion similar to the first portion 3715. In some embodiments, any of the safety members described herein can include an electronics actuation portion similar to the electronic activation protrusion 1720 of the safety lock 1700. In some embodiments, any of the safety members described herein can include a needle sheath engagement portion similar to the needle sheath aperture 1725 and related structure of the safety lock 1700.

Although the electronic circuit system 1900 is shown and described as including one or more switches having two states, in other embodiments, and electronic circuit system can include any suitable switch having any suitable number of states. Similarly stated, in some embodiments, any of the switches described herein can be any electronic component (e.g., resistor) that senses a change in conditions (e.g., a pressure exerted, a break in the circuit, or the like) and produces a signal.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above. For example, although the medical injector 1000 is shown and described as completing the mixing operation in two distinct phases (i.e., as moving to the fourth and fifth configurations), in some embodiments, the venting (or priming) operation and the mixing of the diluent and the solid medicament can be included in a single operation. Similarly stated, in some embodiments, the mixing of diluent can begin before the needle is placed in fluid communication with the medicament container and/or before the gas is purged.

Although the medicament delivery devices described herein are configured to initiate a mixing and/or venting operation when being placed in the device is placed is a predetermined orientation, in other embodiments, a medicament delivery device need not be disposed in a predetermined orientation to allow and/or initiate mixing and/or venting. For example, while the safety lock 1700 is shown and described herein as being maintained in a substantially fixed position relative to the housing 1100 until the medicament delivery device 1000 is placed in a predetermined orientation (e.g., pointing upward), in other embodiments, the safety lock 1700 can selectively engage the housing 1100 in any suitable manner such that removal of the safety lock 1700 from the housing 1100 actuates and/or initiates a mixing operation.

Although the medicament delivery devices are shown and described herein as being medical injectors having a medicament container divided into two portions (see e.g., the medical injector 1000), in other embodiments, any of the components, methods and/or formulations described herein can be used in any suitable medicament delivery device, such as, for example, an auto-injector, a pen injector, an inhaler, patch-pump, a nasal delivery system or the like. In some embodiments, the medicament delivery device can include a medicament container having any number of plungers and/or defining any number of volumes therein.

Although the medicament container 1210 is shown as being initially spaced apart from and/or fluidically isolated from the needle 1240, in other embodiments, a medical injector 1000 can include a medicament container that has a staked needle. For example, in some embodiments, a medical injector 1000 includes a prefilled syringe in which the needle is in fluid communication with the medicament container. In such embodiments, the mixing operation need not, therefore, place the container in fluid communication with the needle.

Although the components and methods described herein are shown and described as being included in devices that include a medicament, in other embodiments, any of the components and/or methods described herein can be used in either an actual medicament delivery device or a simulated medicament delivery device. A simulated medicament delivery device, for example, can correspond to an actual medicament delivery device and can facilitate the training of a user in the operation of the corresponding actual medicament delivery device. A simulated medicament delivery device or trainer can be similar to the simulated medicament delivery devices or trainers described in U.S. Patent Publication Number 2008/0059133, entitled "Medical Injector Simulation Device," filed Feb. 27, 2007, which is incorporated herein by reference in its entirety.

In such embodiments, the simulated medicament delivery device can simulate the actual medicament delivery device in any number of ways. For example, in some embodiments, the simulated medicament delivery device can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device can include components that correspond to the components of the actual medicament delivery device. In this manner, the simulated medicament delivery device can simulate the look, feel, forces, and sounds of the actual medicament delivery device. For example, in some embodiments, the simulated medicament delivery device can include external components (e.g., a housing, a needle guard, a sterile cover, a safety lock or the like) that correspond to external components of the actual medicament delivery device. In some embodiments, the simulated medicament delivery device can include internal components (e.g., an actuation mechanism, a compressed gas source, a medicament container or the like) that correspond to internal components of the actual medicament delivery device.

In some embodiments, however, the simulated medicament delivery device can be devoid of a medicament and/or those components that cause the medicament to be delivered (e.g., a needle, a nozzle or the like). In this manner, the simulated medicament delivery device can be used to train a user in the use of the actual medicament delivery device without exposing the user to a needle and/or a medicament. Moreover, the simulated medicament delivery device can have features to identify it as a training device to prevent a user from mistakenly believing that the simulated medicament delivery device can be used to deliver a medicament. For example, in some embodiments, the simulated medicament delivery device can be of a different color than a corresponding actual medicament delivery device. Similarly, in some embodiments, the simulated medicament delivery device can include a label and/or other indicia clearly identifying it as a training device.

Although the electronic circuit system 1900 is shown and described above as having two reversible switches (e.g., switch 1925 and switch 1926), in other embodiments, an electronic circuit system can have any number of switches. Such switches can be either reversible or irreversible. Although the electronic circuit system 1900 is shown and described above as producing an electronic output in response to the actuation of the two switches 1925 and 1926, in other embodiments, an electronic circuit system can produce an electronic output in response to any suitable input, command or prompt. Suitable input for prompting an output can include, for example, an audible input by the user (e.g., the user's response to a voice prompt produced by the electronic circuit system), an input from a "start button" depressed by the user, an input from a sensor (e.g., a proximity sensor, a temperature sensor or the like), movement of (e.g., shaking) of the medicament delivery device, or the like. In some embodiments, an electronic circuit system can include a microphone and/or a voice recognition module to detect a user's vocal input, an electronically produced input, or other sound to process and cause a subsequent action. In some embodiments, the electronic circuit system 1900 can include a "configuration switch" (similar to any of the switches shown and described above, such as the switch 1925) that, when actuated during the assembly of the delivery device, can select an electronic output corresponding to a dose contained within the medicament container (e.g., 0.4 mg, 0.8 mg, 1.0 mg, 1.6 mg, 2.0 mg, or more).

Although the electronic circuit system 1900 includes three LEDs 1940 and the audio output device 1930, in other embodiments a medical device can have any number of LEDs and/or audio output devices. Additionally, other types of output devices, such as haptic output devices, can be used. In some embodiments, outputs from an electronic circuit system can include, for example, an audible or visual output related to the composition of the medicament (e.g., an indication of the expiration date, the symptoms requiring treatment with the medicament or the like), the use of the medicament delivery device, and/or post-administration procedures (e.g., a prompt to call 911, instructions for the disposal of the device or the like).

In some embodiments, the audible sound produced by any of the devices shown and described herein can be produced in conjunction with one or more visual outputs. For example, in some embodiments, a medicament delivery device can include a video screen (e.g., an LCD screen) upon which messages, videos and/or other instructions can be shown during use of the device. In some embodiments, the device can include a touch screen such that, in addition to the feedback from the movement of various components of the device (e.g., the carrier) as described herein, the electronic circuit system can receive input directly from the user.

Although the electronic circuit system 1900 is shown and described above as being actuated by the removal of the cover 1180 and/or the movement of the system actuator assembly 1500, in other embodiments, an electronic circuit system can be actuated by any suitable mechanism. In some embodiments, for example, a medicament delivery device can include a movable battery clip, an on/off switch or the like that can be manipulated by the user to actuate the electronic circuit system. In some embodiments, for example, a medical injector need not have a cover similar to the cover 1180; rather, the medical injector can be manually actuated by a "start" button depressed by the user. In some embodiments, the electronic circuit system 1900 of the types shown and described herein can be used in either an actual medicament delivery device or a simulated medicament delivery device.

Although the carrier 1260 is shown and described above as receiving a portion of the medicament container 1210, in other embodiments, a carrier can substantially surround the medicament container 1210. For example, in some embodiments, a carrier can include a first portion and a second portion coupled by a hinge, such that the carrier can be configured between a first (opened) configuration and a second (closed) configuration. In this manner, the carrier 1260 can be configured to receive at least a portion of the medicament container 1210 when in the open configuration and can be moved to the closed configuration to substantially surround the medicament container 1210.

Although the carrier 1260 is shown and described as being coupled to the needle 1240, in other embodiments, a device can include a carrier and/or medicament container that is devoid of a needle. For example, in some embodiments, a medicament delivery device such as the medicament delivery device 1000 can be a needleless injector, which includes a carrier and/or medicament container that defines a pathway and/or otherwise coupled to a delivery member through which the medicament is conveyed upon actuation.

Although the mixing of the diluent volume 1226 and the dry medicament volume 1227 is shown and described above as being actuated and/or initiated by the removal of the safety lock 1700 from the housing 1100, in other embodiments, a mixing operation can be actuated and/or initiated by any suitable mechanism. For example, in some embodiments, a mixing operation can be initiated by an actuator such as the system actuator assembly 1500 being moved from a first position to a second position.

Any of the medicament containers described herein can be any container suitable for storing the compositions disclosed herein. In some embodiments, the medicament container can be a pre-filled syringe, a pre-filled cartridge, a vial, an ampule or the like. In some embodiments, for example, any of the devices shown and described herein can include components and/or mechanisms to accommodate a pre-filled syringe, similar to the embodiments shown and described in U.S. Patent Publication No. 2013/0023825 entitled, "Medicament Delivery Devices for Administration of Medicament within a Prefilled Syringe," filed Jan. 25, 2012 the disclosure of which is incorporated herein by reference in its entirety. In other embodiments, the medicament containers described here can be a container having a flexible wall, such as, for example, a bladder.

Any of the devices and/or medicament containers shown and described herein can be included in a kit (not shown), which can include fungible components and reusable components. For example, in some embodiments, at least a housing of a medical injector can be reusable without the need for sterilization, as described in detail above. In some embodiments, such as with the medical injector 1000, the proximal cap 1160 can be removed from the housing 1100 to allow access to and removal of the used components disposed within the housing 1100. In addition, the removal of the proximal cap 1160 from the housing 1100 can allow for any suitable portion of the medical injector 1000 to be reset to, for example, a pre-activated or pre-actuated configuration, as described above.

Although the housing 1100 is shown and described above as being monolithically constructed and subsequently coupled to the proximal cap 1160, in other embodiments, a medical injector can include a housing having multiple portions, which can allow for replacement of used components. For example, such a housing can include a first portion or side matingly coupled to a second portion or side. In such embodiments, the housing can include one or more seal members or the like that can be disposed between mating surfaces of the first portion and second portion. Thus, the coupled portions of such a housing can collectively define a gas cavity, a medicament cavity, and a mixing actuator cavity similar to the gas cavity 1132, the medicament cavity 1141, and the mixing actuator cavity 1142, respectively, of the housing 1100. Thus, such a housing can allow access to an inner volume of collectively defined by the portions of the housing to allow a user to replace used components with unused components and to reset actuated and/or activated portions of such a device to un-actuated and/or un-activated configurations.

Moreover, in some embodiments, such a medical injector can be packaged with and/or otherwise included in a kit, which contains, for example, the reusable portions of that medical injector (e.g., a housing, a system actuator, and electronic circuit system, a safety lock, a case, and/or the like) and fungible portions of that medical injector (e.g., a medicament container, a carrier, a gas container, and/or the like). In some embodiments, the kit can include one reusable portion of that medical injector and any number of fungible portions of that medical injector included one fungible portion pre-assembled and stored in the reusable portion (e.g., the housing).

Any of the devices and/or medicament containers shown and described herein can be constructed from any suitable material. Such materials include glass, plastic (including thermoplastics such as cyclic olefin copolymers), or any other material used in the manufacture of prefilled syringes containing medications.

Although the medical injector 1000 is shown and described above as including portions of the medicament container assembly 1200 as being actuated by the expansion of a compressed gas, in other embodiments, such portions of a medicament container and/or any other portion of a medical injector can be actuated by a spring and/or any other suitable member configured to exert a force. For example, in some embodiments, a medical injector can include a medicament container and a carrier configured to move in a distal direction in response to a force exerted by a spring. Conversely, while the medical injector 1000 is shown and described above as including portions of the medicament container assembly 1200 and/or the system actuator assembly 1500 as being actuated by a spring, in other embodiments such portions of a system actuator assembly and/or a medicament container assembly can be actuated by an expansion of a compressed gas and/or the like. For example, while the mixing of the diluent volume 1226 and the dry medicament volume 1227 is shown and described above as being activated and/or initiated by the bias member 1295, in other embodiments, an expansion of gas released from the gas container 1580 can activate and/or initiate a mixing event. In still other embodiments, a mixing portion of medical injector can include a gas container distinct from, for example, the gas container 1580.

Any of the devices and/or medicament containers shown and described herein can include any suitable medicament or therapeutic agent. For example, although the medical injectors described above are shown and described is including a multi-chamber medicament container (e.g., medicament container 1210) that includes a substantially dry medicament (e.g., contained within the dry medicament volume 1227) and a diluent (e.g., contained within the diluent volume 1226), in other embodiments, any of the medicament delivery devices disclosed herein can include a multi-chamber container that is filled with any suitable substances. For example, in some embodiments, any of the medicament delivery devices disclosed herein can include a medicament container (e.g., a cartridge) that separately stores and mixes, upon actuation, two liquid substances. For example in some embodiments, any of the devices shown and described herein can include a medicament container filled with (in separate chambers) epinephrine and at least one antihistamine (e.g., epinephrine and diphenhydramine, epinephrine and hydroxyzine, epinephrine and cetirizine); an antipsychotic medicament and a benzodiazepine (e.g. haloperidol and diazepam, haloperidol and midazolam, haloperidol and lorazepam); insulin and a GLP-1 analog or incretin mimetic (e.g. insulin and exenatide, insulin and lixisenatide); an NSAID and an opiode (e.g., ketorolac and buprenorphine). Other suitable compositions that can be included in any of the medicament containers and/or devices described herein include pralidoxime chloride and atropine; obidoxime chloride and atropine; epinephrine and atropine; methotrexate and etanercept; methotrexate and adalimumab; and methotrexate and certolizumab.

Glucagon Formulation

In some embodiments, a composition can include glucagon and/or any pharmaceutically acceptable constituents for use in the medicament delivery devices disclosed herein. In some embodiments, the glucagon formulation can be prepared and/or filled according to any suitable method such as, for example, those described in U.S. Patent Publication No. 2013/0023822 incorporated by reference hereinabove. A composition according to an embodiment can be formulated such that the target concentration of glucagon in the solution, either before lyophilization and/or after being reconstituted upon actuation of the device, is approximately 1 mg/mL. In other embodiments, the target concentration of glucagon in the solution, either before lyophilization and/or after being reconstituted, can be approximately 2 mg/mL, approximately 1.5 mg/mL, approximately 0.5 mg/mL (e.g., a pediatric dose) or approximately 0.25 mg/mL. In other embodiments, a composition can be formulated such that the target concentration of glucagon in the solution, either before lyophilization and/or after being reconstituted upon actuation of the device, is between approximately 0.25 mg/mL and 2 mg/mL, between approximately 0.5 mg/mL and 1 mg/mL, or between approximately 0.8 mg/mL and 1.2 mg/mL.

In certain embodiments, the concentration (either before lyophilization or upon reconstitution) of glucagon in a glucagon formulation is about 1 mg/mL and the total solute concentration is about 50 mg/mL. For example, in some embodiments, a composition can include glucagon and any suitable bulking agents to increase the total solute concentration in the glucagon formulation. In this manner, the glucagon formulation can be more effectively lyophilized and/or reconstituted. For example, in some embodiments, as described below, certain bulking agents can be used to improve the stability, solubility and/or efficacy of the composition when reconstituted in any of the devices shown and described herein. In some embodiments, certain bulking agents can be used to produce a visual indicia when the composition is reconstituted (e.g., such agents can allow the reconstituted medicament to be more easily detected by the user).

In some embodiments, a composition can include a peptide, such as, for example, glucagon and a carbohydrate. In this manner, the stability of the peptide (e.g., glucagon) can be increased during lyophilization and subsequent storage. In particular, the stability of peptides, such as glucagon, can be increased in an amorphous (i.e. non-crystalline) environment. It is believed that carbohydrates undergoing dehydration create a solid-state environment that is amorphous and exhibits high viscosity when maintained below the glass transition temperature. In addition, carbohydrates contain multiple hydroxyl groups that may form hydrogen bonds with polar groups on a protein or peptide surface in an amorphous solid-state environment. Without being bound by any particular mechanism, when water is removed during lyophilization, such carbohydrates may maintain the hydrogen bonds and preserve the native-like solid state of the polypeptide structure. In certain embodiments, therefore, the glucagon formulations include other excipients, such as, but not limited to carbohydrates. Suitable carbohydrates include, but are not limited to, lactose, trehalose, mannitol, and combinations thereof.

Additionally, the solubility of glucagon increases below a pH of 4. In certain embodiments, the glucagon formulations, prior to lyophilization and/or after reconstitution, have a pH of less than about pH 5.0, including less than about pH 4.5, less than about pH 4.0, less than about pH 3.5, less than about pH 3.0, less than about pH 2.5, less than about pH 2.0. In other embodiments of the invention, the glucagon formulations, prior to lyophilization and/or after reconstitution, have a pH range of about pH 1.5 to about pH 5.0, inclusive of all ranges and subranges therebetween, e.g., about pH 2.0 to about pH 4.5, about pH 2.0 to about pH 4.0, about pH 2.0 to about pH 3.5, about pH 2.0 to about pH 3.0, about pH 2.0 to about pH 2.5, about pH 2.5 to about pH 4.5, about pH 2.5 to about pH 4.0, about pH 2.5 to about pH 3.5, about pH 2.5 to about pH 3.0, about pH 3.0 to about pH 4.5, about pH 3.0 to about pH 4.0, about pH 3.0 to about pH 3.5, about pH 3.5 to about pH 4.5, and about pH 3.5 to about pH 4.0. In certain embodiments, the pH of the glucagon formulation is adjusted prior to lyophilization by the addition of a suitable acid, such as hydrochloric acid or citric acid.

The lyophilized formulations of the present invention may be reconstituted by any suitable diluent or combination of diluent, including, but not limited to, water, sterile water, glycerin, or hydrochloric acid.

As described above, in some embodiments, a glucagon formulation can include any suitable bulking agents and/or excipients. Table 1 lists the formulations investigated for lyophilization. The formulations set for the below include a concentration of glucagon in the solution, either before lyophilization and/or after being reconstituted, of approximately 1 mg/mL.

TABLE 1

| Formulation | Excipients and Concentration | Medicament |
|---|---|---|
| 1 | Lactose - 49 mg/mL | 1 mg/mL glucagon |
| 2 | Trehalose - 40 mg/mL<br>Mannitol - 20 mg/mL | 1 mg/mL glucagon |
| 3 | Trehalose - 40 mg/mL<br>Mannitol - 20 mg/mL<br>Citric acid - 1.8 mg/mL<br>Sodium citrate - 0.35 mg/mL | 1 mg/mL glucagon |
| 4 | Glycine - 20 mg/mL | 1 mg/mL glucagon |
| 5 | Mannitol - 40 mg/mL<br>Ascorbic acid - 5 mg/mL | 1 mg/mL glucagon |

Formulation 1 included lactose, which is a known animal-derived excipient. Lactose, which is used in the commercially available glucagon formulations, is a reducing sugar that may destabilize glucagon. Accordingly, Formulations 2 through 5 are lactose-free formulations. Formulation 2 utilized trehalose and mannitol as carbohydrate bulking agents. Formulation 3 included a buffer system of citric acid and sodium citrate, in addition to the carbohydrate bulking agents. Formulation 4 was carbohydrate free, containing only glycine as the bulking agent. Formulation 5 utilized only mannitol as a bulking agent and included ascorbic acid. All formulations except Formulation 3 employed hydrochloric acid to reduce the solution pH to approximately 3 before lyophilization.

Trehalose, however, is a non-reducing sugar, and without being bound by any particular mechanism, may potentially increase the stability of glucagon, prior to lyophilization, during lyophilization, in storage, and/or after reconstitution. In addition to the improved properties of Formulation 3, the absence of any animal-based excipients, such as lactose, make it particularly appealing from a regulatory standpoint, as the FDA has strict guidelines regarding animal-based excipients.

All five formulations listed in Table 1 were successfully reconstituted with water and resulted in solutions suitable for use in the multi-chambered container closure system of the present invention.

In some embodiments, the medicament contained within any of the medicament containers shown herein can be a vaccine, such as, for example, an influenza A vaccine, an influenza B vaccine, an influenza A (H1N1) vaccine, a hepatitis A vaccine, a hepatitis B vaccine, a *haemophilus influenza* Type B (HiB) vaccine, a measles vaccine, a mumps vaccine, a rubella vaccine, a polio vaccine, a human papilloma virus (HPV) vaccine, a tetanus vaccine, a diphtheria vaccine, a pertussis vaccine, a bubonic plague vaccine, a yellow fever vaccine, a cholera vaccine, a malaria vaccine, a smallpox vaccine, a pneumococcal vaccine, a rotavirus vaccine, a varicella vaccine and/or a meningococcus vaccine. In other embodiments, the medicament contained within any of the medicament containers shown herein can be epinephrine. In other embodiments, the medicament contained within any of the medicament containers shown herein can be naloxone, including any of the naloxone formulations described in U.S. patent application Ser. No. 13/036,720, entitled "Medicament Delivery Device for Administration of Opioid Antagonists Including Formulation for Naloxone," filed on Feb. 28, 2011, the disclosure of which is incorporated herein by reference in its entirety.

In other embodiments, the medicament contained within any of the medicament containers shown herein can include insulin, glucagon, human growth hormone (HGH), erythropoiesis-stimulating agents (ESA), DeMab, Interferon and other chronic therapies, or the like. Such formulations can be produced using a general lyophilization process with glucagon (of recombinant origin) using bulking agents, stabilizers, buffers, acidifying agents or other excipients comprising of, but not limited to, one or more of the following combinations: lactose, hydrochloric acid; glucose, histidine, hydrochloric acid; trehalose, mannitol, citrate; trehalose, mannitol, hydrochloric acid; trehalose, glycine, hydrochloric acid; Mannitol, ascorbic acid; and Glycine, hydrochloric acid.

In other embodiments any of the injectors described herein can be filled with and/or used to inject medicament formulations, including lyophilized biologics and/or biopharmaceuticals, such as, for example, canakinumab, certolizumab, golimumab, and/or interleukins, for the treatment of crypyrin associated periodic syndromes, hereditary andioedema, and other auto-immune diseases. In yet other embodiments any of the injectors described herein can be filled with and/or used to inject intranasal biologics, such as glucagon or human growth hormone, formulated for use in an auto injector, for the treatment of musculoskeletal diseases, growth disorders, diabetes & treatment related disorders.

In other embodiments, any of the injectors described herein can be filled with and/or used to inject an anti-thrombotics, such as LMWH, ULMWH, Xa Inhibitors, biotinylated idraparinux, etc., for either the acute management and/or surgical prophylaxis of deep vein thrombosis and/or pulmonary embolism or for the management of other conditions which may require anticoagulation to prevent thromboembolism, such as its use in cardiovascular diseases including atrial fibrillation and ischemic stroke. In another example, in some embodiments an injector according to an embodiment can be filled with and/or used to inject formulations for the treatment of asthma and/or chronic obstructive pulmonary disease.

In other embodiments, any of the injectors described herein can be filled with and/or used to inject recombinant hyaluronidase.

In other embodiments, any of the injectors described herein can be filled with and/or used to inject depot medroxyprogesterone acetate for the treatment of infertility.

In other embodiments, any of the injectors described herein can be filled with and/or used to inject environmental, food, and household allergen formulations for the treatment of allergic disease, specifically for use in immunotherapy.

In still other embodiments, the medicament contained within any of the medicament containers shown herein can be a placebo substance (i.e., a substance with no active ingredients), such as water.

The medicament containers and/or medicament delivery devices disclosed herein can contain any suitable amount of any medicament. For example, in some embodiments, a medicament delivery device as shown herein can be a single-dose device containing an amount medicament to be delivered of approximately 0.4 mg, 0.8 mg, 1 mg, 1.6 mg or 2 mg. As described above, the fill volume can be such that the ratio of the delivery volume to the fill volume is any suitable value (e.g., 0.4, 0.6 or the like).

In some embodiments, a method includes moving a first elastomeric member within a medicament container such that a medicament within a first chamber is compressed. The medicament can be, for example, a substantially solid medicament, such as a lyophilized medicament that that contains air therein. In other embodiments, the medicament within the first chamber can include a liquid component, and the first chamber can include air. In this manner, a portion of the air within the first chamber can be conveyed (or purged) from the first chamber. As described herein, in some embodiments, the air from the first chamber can be conveyed into a second chamber of the medicament container. In some embodiments, the method includes puncturing a second elastomeric member or seal member, which defines a boundary of the second chamber such that a portion of the air within the second chamber is conveyed via the needle to volume outside of the medicament container. In other embodiments, the air from the first chamber can be conveyed to a volume outside of the medicament container.

Although the medicament containers and methods of air venting and/or purging have been described herein as being associated with an auto-injector, in other embodiments, any of the medicament containers and methods of air venting and/or purging described herein can be used in any suitable medicament delivery device. For example, in some embodiments, a medicament container similar to the medicament container 1210 described above can be included in a pen injector, an inhaler, an infusion device, patch-pump, or a transdermal delivery device.

In some embodiments, a method includes actuating an energy storage member configured to produce a force on a portion of a medicament container. The portion can be, for example, a plunger (or elastomeric member) that is movable within the medicament container. In other embodiments, the force can be exerted on a portion of the medicament container such that the portion deforms to reduce a volume within which a medicament is stored. The application of the force is such that the volume is reduced, thereby compressing and/or conveying air from the volume to a volume outside of the medicament container. In this manner, any residual air within the medicament volume can be purged without the need for the user to manually apply a purge force. Moreover, although the venting and/or purging operation is described above as being initiated by the device being placed in a predetermined orientation, in some embodiments, the venting and/or purging can be independent from the orientation of the device.

What is claimed is:

1. An apparatus, comprising:
a housing configured to contain at least a portion of a medicament container, the housing including a housing surface defining a lock chamber;
a safety member coupled to the housing and configured to be moved relative to the housing between a first position and a second position, the safety member configured to limit delivery of a contents of the medicament container when the safety member is in the first position, an outer surface of the safety member disposed outside of the housing, a lock protrusion of the safety member disposed within the lock chamber of the housing when the safety member is in the first position, the lock protrusion disposed outside of the lock chamber when the safety member is in the second position; and
a lock member disposed within the lock chamber of the housing and configured to move along the housing surface when an orientation of a longitudinal axis of the medicament container changes, the lock member positioned in contact with the lock protrusion of the safety member to limit movement of the safety member from the first position to the second position when the longitudinal axis of the medicament container is in a first orientation, the lock member spaced apart from the lock protrusion when the longitudinal axis of the medicament container is in a second orientation,
wherein the safety member is removed from the housing when the safety member is in the second position.

2. The apparatus of claim 1, the lock protrusion of the safety member defines a recessed portion configured to receive the lock member when the longitudinal axis of the medicament container is in the first orientation.

3. The apparatus of claim 1, wherein:
the lock protrusion of the safety member is one of a plurality of lock protrusions; and
the housing defines a plurality of openings, each lock protrusion from the plurality of lock protrusions configured to be disposed through a corresponding opening from the plurality of openings and within the lock chamber of the housing when the lock member is in the first position.

4. The apparatus of claim 1, wherein:
the housing surface defining the lock chamber is angularly offset from a longitudinal axis of the medicament container,
the housing surface is a first housing surface;
the housing includes a second housing surface that forms a nonzero angle with the first housing surface; and
the lock member is configured to move along one of the first housing surface or the second housing surface when the orientation of the longitudinal axis of the medicament container changes.

5. The apparatus of claim 1, wherein the outer surface of the safety member is configured to be manipulated to move the safety member from the first position to the second position when the longitudinal axis of the medicament container is in the second orientation.

6. The apparatus of claim 1, wherein the lock member has a spherical shape and is configured to roll along the housing surface.

7. The apparatus of claim 1, wherein:
the housing surface is a conical surface; and
the lock member has a spherical shape and is configured to roll along the conical surface of the lock chamber.

8. The apparatus of claim 1, wherein:
the housing surface is a first conical surface;
the housing includes a second conical surface opposite the first conical surface that forms a nonzero angle with the first conical surface; and
the lock member is configured to roll between the first conical surface and the second conical surface when the orientation of the longitudinal axis of the medicament container changes.

9. The apparatus of claim 1, further comprising:
a movable member coupled to the medicament container, the movable member configured to move within housing to deliver the contents from the medicament container, the movable member including a retention portion engaged with the safety member to limit movement of the movable member when the safety member is in the first position.

10. The apparatus of claim 1, wherein the safety member defines a volume within which a portion of the housing is contained when the safety member is in the first position.

11. The apparatus of claim 1, wherein: the medicament container is coupled to a delivery member through which the contents are delivered, the delivery member being aligned with the longitudinal axis; and the longitudinal axis and an upward vertical axis form an angle of between about 25 degrees and −25 degrees.

12. An apparatus, comprising:
a medicament container, the medicament container including a first elastomeric member and a second elastomeric member, the first elastomeric member disposed within a proximal end portion of the medicament container and defining, at least in part, a first volume containing a first substance, the second elastomeric member disposed distally from the first elastomeric member, the second elastomeric member, the first elastomeric member, and a portion of the medicament container collectively defining a second volume containing a second substance;
a housing configured to contain at least a portion of the medicament container;
an energy storage member disposed within the housing, the energy storage member configured to produce a force to convey a contents of the medicament container when the energy storage member is actuated to release a potential energy stored therein, the contents of the medicament container including a gas from the second volume; and
a safety member coupled to the housing, a first portion of the safety member configured to actuate the energy storage member when the safety member is moved relative to the housing between a first position and a second position, a second portion of the safety member configured to engage a lock member within the housing to limit movement of the safety member from the first position to the second position when a longitudinal axis of the medicament container is in a first orientation, the second portion of the safety member spaced apart from the lock member when the longitudinal axis of the medicament container is in a second orientation.

13. The apparatus of claim 12, further comprising:
the lock member configured to move within the housing when an orientation of a longitudinal axis of the medicament container changes.

14. The apparatus of claim 12, wherein the first substance is a liquid diluent and the second substance is a lyophilized medicament.

15. The apparatus of claim 14, wherein the lyophilized medicament includes glucagon.

16. The apparatus of claim 12, wherein the energy storage member is a first energy storage member, the first energy storage member being any of a gas container, a chemical energy storage member, a spring, or an electrical energy storage member,
the force is a first force, the potential energy is a first potential energy, the contents are a first contents, the apparatus further comprising:
a second energy storage member configured to produce a second force to convey a second contents of the medicament container when the second energy storage member is actuated to release a second potential energy stored therein; and
an actuator configured to actuate the second energy storage member when the actuator is moved relative to the housing, the safety member configured to limit movement of the actuator when the safety member is in the first position.

17. The apparatus of claim 12, further comprising:
a mixing protrusion disposed within the housing, at least a portion of the force produced by the energy storage member exerted by the mixing protrusion onto the first elastomeric member to convey the contents of the medicament container.

18. The apparatus of claim 12, wherein the housing includes a housing surface defining at least a portion of a lock chamber, the housing surface being angularly offset from a longitudinal axis of the medicament container, the apparatus further comprising:

the lock member disposed within the lock chamber of the housing and configured to move along the housing surface when the orientation of the longitudinal axis of the medicament container changes, the lock member positioned in contact with a lock protrusion of the safety member to limit movement of the safety member from the first position to the second position when the longitudinal axis of the medicament container is in the first orientation, the lock member spaced apart from the lock protrusion when the longitudinal axis of the medicament container is in the second orientation, and the lock protrusion of the safety member defines a recessed portion configured to receive the lock member when the longitudinal axis of the medicament container is in the first orientation.

19. An apparatus, comprising: a safety member configured to be coupled to a housing of a medicament delivery device, the safety member configured to be moved relative to the housing between a first position and a second position, a lock portion of the safety member configured to be disposed within a lock chamber defined by the housing when the safety member is in the first position, the lock portion configured to engage a lock member within the lock chamber to limit movement of the safety member from the first position to the second position when a longitudinal axis of the housing is in a first orientation, the lock portion spaced apart from the lock member when the longitudinal axis of the housing is in a second orientation, an actuation portion of the safety member configured to actuate an energy storage member of the medicament delivery device when the safety member is moved from the first position to the second position, the energy storage member configured to produce a force to convey a contents from a medicament container of the medicament delivery device when the energy storage member is actuated, wherein the lock portion includes a plurality of lock protrusions, each lock protrusion from the plurality of lock protrusions configured to be disposed through a corresponding opening from a plurality of openings defined by the housing and within the lock chamber of the housing when the safety member is in the first position; and the plurality of lock protrusions collectively define a volume within which the lock member is disposed when the safety member is in the first position and when the longitudinal axis of the medicament container is in the first orientation.

20. The apparatus of claim 19, wherein:
the safety member is removed from the housing when the safety member is in the second position; and
the lock portion of the safety member includes a curved surface configured to receive the lock member when the longitudinal axis of the medicament container is in the first orientation.

21. The apparatus of claim 19, wherein:
the medicament delivery device is a medical injector having a needle through which the contents from the medicament container is conveyed; and
a needle sheath engagement portion of the safety member configured to be coupled to a needle sheath covering the needle when the needle sheath engagement portion is in the first position, the needle sheath engagement portion configured to remove the needle sheath from about the needle when the safety member is moved from the first position to the second position.

22. The apparatus of claim 19, wherein the safety member includes a side wall defining an internal volume, the side wall surrounding an end portion of the housing of the medicament delivery device when the safety member is in the first position.

23. The apparatus of claim 19, wherein the medicament delivery device is any one of a single-use auto-injector, a reusable auto-injector, a pen injector, or an inhaler.

* * * * *